(12) United States Patent
Eustache et al.

(10) Patent No.: US 6,803,382 B2
(45) Date of Patent: Oct. 12, 2004

(54) ANGIOGENESIS INHIBITORS AND PHARMACEUTICAL AND COSMETIC USE THEREOF

(75) Inventors: Jacques Eustache, Mulhouse (FR); Jean-Guy Boiteau, Saint-Aunes (FR); Céline Tarnus, Illzach (FR); Vincent Rodeschini, Mulhouse (FR); Pierre Van De Weghe, Baldersheim (FR)

(73) Assignee: Galderma Research & Development, S.N.C., Valbonne (FR)

( * ) Notice: Subject to any disclaimer, the term of this patent is extended or adjusted under 35 U.S.C. 154(b) by 0 days.

(21) Appl. No.: 10/290,388

(22) Filed: Nov. 8, 2002

(65) Prior Publication Data
US 2003/0134896 A1 Jul. 17, 2003

Related U.S. Application Data
(60) Provisional application No. 60/351,426, filed on Jan. 28, 2002.

(30) Foreign Application Priority Data
Nov. 9, 2001 (FR) .............................................. 0114542

(51) Int. Cl.⁷ .................... A61K 31/336; C07D 303/06
(52) U.S. Cl. ........................ 514/475; 549/332; 424/401
(58) Field of Search ........................ 514/475; 549/332; 424/401

(56) References Cited

U.S. PATENT DOCUMENTS 6,017,954 A    1/2000   Folkman et al.

FOREIGN PATENT DOCUMENTS

| EP | 0 357 061 A1 | 3/1990 |
|---|---|---|
| EP | 0 359 036 A1 | 3/1990 |
| EP | 0 387 650 A1 | 9/1990 |
| WO | WO 96/26712 A2 | 9/1996 |
| WO | WO 98/56372 A1 | 12/1998 |
| WO | WO 99/61432 A1 | 12/1999 |

OTHER PUBLICATIONS

Griffith et al., "Mathionine aminopeptidase (type 2) is the common target for angiogenesis inhibitor AGM–1470 and ovalicin", XP–008006407, Chemistry & Biology, Jun. 1997, ppg 461–471, vol. 4, No. 6, Current Biology, London, GB.

*Primary Examiner*—Taofiq Solola
(74) *Attorney, Agent, or Firm*—Burns, Doane, Swecker & Mathis, L.L.P.

(57) ABSTRACT

The invention relates to novel 1-oxaspiro[2,5]octan-6-ol derivatives of general formula (I):

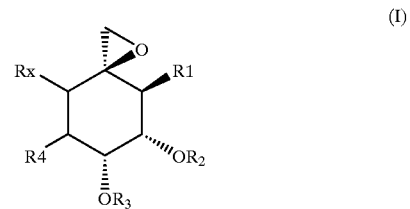

and also to a method for preparing them, and to their use in pharmaceutical compositions for use in human or veterinary medicine, or in cosmetic compositions.

17 Claims, 2 Drawing Sheets

ANGIOGENESIS INHIBITORS AND PHARMACEUTICAL AND COSMETIC USE THEREOF

CROSS-REFERENCE TO RELATED APPLICATIONS

This application claims priority under 35 U.S.C. §§ 119 and/or 365 to FR 01/14542 filed in France on Nov. 9, 2001; the entire content of which is hereby incorporated by reference.

This application claims priority under 35 U.S.C. § 119 to U.S. Provisional Application No. 60/351,426 entitled NOUVEAUX INHIBITEURS DE L'ANGIOGENESE ET LEUR UTILISATION PHARMACEUTIQUE ET COSMETIQUE and filed on Jan. 28, 2002, the entire content of which is hereby incorporated by reference.

BACKGROUND OF THE INVENTION

1. Field of the Invention

The invention relates, as novel and useful industrial products, to novel 1-oxaspiro[2,5]octan-6-ol derivatives. The invention also relates to a process for preparing them and to their use in pharmaceutical compositions for use in human or veterinary medicine, or in cosmetic compositions.

2. Description of Related Art

It is known that angiogenesis is the formation of new blood capillaries from already-existing blood vessels. Angiogenesis plays an important role in the development of embryonic tissue, but hardly ever features in healthy adult tissue.

The development of new blood vessels may be observed under non-physiological conditions. This development may play a beneficial role, such as, for example, in the case of cicatrization. However, its action is usually deleterious: the development of tumours, accompaniment to chronic inflammatory diseases.

The role of angiogenesis is most frequently manifested in the case of tumours: it has been demonstrated that, during the growth phase, tumours have absolute need of the development of new blood vessels.

Although the link between the development of a tumour and angiogenesis was proposed by Folkman more than 30 years ago (Folkman, J., *New. Engl. J. Med.* 1971, 285, 1182), it has only been in the last ten years that the possibility of antitumoural therapies based on controlling angiogenesis has been widely accepted. Currently, many anti-angiogenic molecules are in the course of clinical study (Norrby, K., *APMIS*, 1997, 105, 417–437; Arbiser, J. L., *J. Am. Acad. Dermatol.* 1996, 34(3), 486–497; Fan, T-P. D., *TIPS*, 1995, 16, 57–66). As has recently been shown (Boehm, T., Folkman, J. et al. *Nature*, 1997, 390, 404–407), an antitumoural therapy based on controlling angiogenesis is less likely to give rise to resistance phenomena.

Angiogenesis is also associated with the pathological process of various inflammatory diseases. In this respect, angiogenesis inhibition may have an implication in the treatment and prevention of these diseases. Abnormal angiogenesis is thus involved in various diseases of inflammatory nature, for instance rheumatoid arthritis, or others, for instance atherosclerosis and retinopathy of diabetic origin.

Many research groups have attempted to discover novel molecules capable of inhibiting angiogenesis, such as, for example, Taylor by application of Protamine (Taylor, S. et al., *Nature*, 1982, 297, 307), or the use of heparin in the presence of cortisone, by Folkman (Folkman, J. et al., *Science*, 1983, 221, 719).

In dermatology, it is very widely accepted that a deregulation of angiogenesis control is associated with a multitude of disorders: tumours, psoriasis, haemangiomas (exaggerated angiogenesis) (Creamer, D. et al., *Br. J. Dermatol*, 1997, 136 (6), 859–865; Jackson, J. R. et al. *FASEB.J*, 1997, 11(6), 457–465), ulcers (deficient angiogenesis).

To date, steroids have been used for the treatment of haemangiomas, the efficacy of which is probably due to their anti-angiogenic activity.

It is also clear that increased attention is being given to angiogenesis as a target for a therapeutic intervention in other dermatological complaints. This is manifested, for example, clinically by the design of studies focused on angiogenesis (Gradishar, W. J. *Invest New Drugs*, 1997, 15(1), 49–59) and by the increasing number of reports, articles and publications relating to angiogenesis (*Ann. Rep. Med. Chem.* 1997, 32, 161–170; *Ann. Rep. Med. Chem.* 1992, 27, 139–148).

Finally, it should be noted that various classes of dermatologically active molecules (retinoids, vitamin 1,25-di-OH-D-3) are now being examined for their potential role on angiogenesis (*Eur J. Pharmacol.* 1993, 249 (1), 113–116; *Cancer Lett.* 1995, 89 (1) 117–124).

In the field of angiogenesis, fumagillin and its derivatives are of particular importance: TNP-470 (AGM 1470) described in patent EP 357 061 and its successor, FR-118 847 described in patent EP 386 667, are active in many angiogenesis models and have recognized antitumoural activity (Logothetis, C. J., *Clin Cancer Res* 2001 May; 7(5):1198–1203).

These compounds are described as having activity in angiogenesis inhibition, the suppression of cell proliferation, and immunosuppression.

These compounds are synthesized by standard semi-synthetic processes as described in patents EP 357 061 and EP 386 667 cited above.

Other fumagillin derivatives, such as the 6-epifumagillols described in patent EP 387 650, also have applications in angiogenesis inhibition, the suppression of cell proliferation and immunosuppression. In this case also, they are synthesized via a semi-synthetic process.

The mode of action of these compounds remained unexplained until 1997 when a biological target, a methionine aminopeptidase: MetAP-2, was identified (Griffith, E. C. et al., *Chem Biol*, 1997, 4(6), 461–471). The inhibitory activity of various fumagillin derivatives with respect to this enzyme shows good correlation with the anti-angiogenic effect.

The discovery of this enzyme has enabled better targeting of the desired activity and the synthesis of novel fumagillin analogues with better biological activity, while at the same time reducing their side effects. In particular, the mode of action proposed by Griffith, Liu and Clardy (a; Liu, S. et al. *Science*, 1998, 282, 1324–1327. b; Griffith, E. C. et al. *Proc. Natl. Acad. Sci. USA*, 1998, 95, 15183–15188) for fumagillin and its analogues involves a crucial interaction between the exocyclic epoxide of these molecules and a cobalt atom located at the active site of MetAP-2 followed by opening of this epoxide by a histidine of the active ring, this sequence leading to an irreversible inhibition of MetAP-2. This model suggests that substituents introduced into the positions of the fumagillin ring system that are still free (positions 7 and 8 of the 1-oxaspiro[2,5]octane ring system) would be capable of interfering with the enzyme close to the active ring, thus disrupting the activity of the inhibitors. The Applicant has used this enzyme in order to identify novel fumagillin derivatives and to exploit better anti-angiogenic candidates for the topical and systemic treatment of complaints that may involve a proliferative, inflammatory and/or immunosuppressant component, especially in the field of dermatology.

BRIEF SUMMARY OF THE INVENTION

The Applicant has thus invented novel derivatives by developing a novel process of total synthesis. This total synthesis gives access to analogues that are very difficult or even impossible to prepare by semi-synthesis. In particular, it allows the functionalization of positions 7 and 8 of the 1-oxaspiro[2,5]octane ring system and the introduction of a wide variety of side chains, and also allows the synthesis of optically active products. This process of total synthesis also offers the advantage of allowing better control and a production that is more economical than the previous semi-synthetic processes.

The Applicant has moreover discovered that a key area in the formation of the active molecule-biological target complex concerns the substituents in positions 7 and 8 of the 1-oxaspiro[2,5]octane ring system, and that it could be advantageous to be able to benefit from novel fumagillin derivatives bearing substitution in positions 7 and 8 of the 1-oxaspiro[2,5]octane ring system and/or a modified side chain and not comprising an epoxide function, so as to be able to identify better anti-angiogenic candidates for the topical and systemic treatment of complaints that may involve a proliferative, inflammatory and/or immunosuppressant component, especially in the field of dermatology.

Such derivatives may also be obtained according to the present invention.

DETAILED DESCRIPTION OF THE INVENTION

Figure 1:
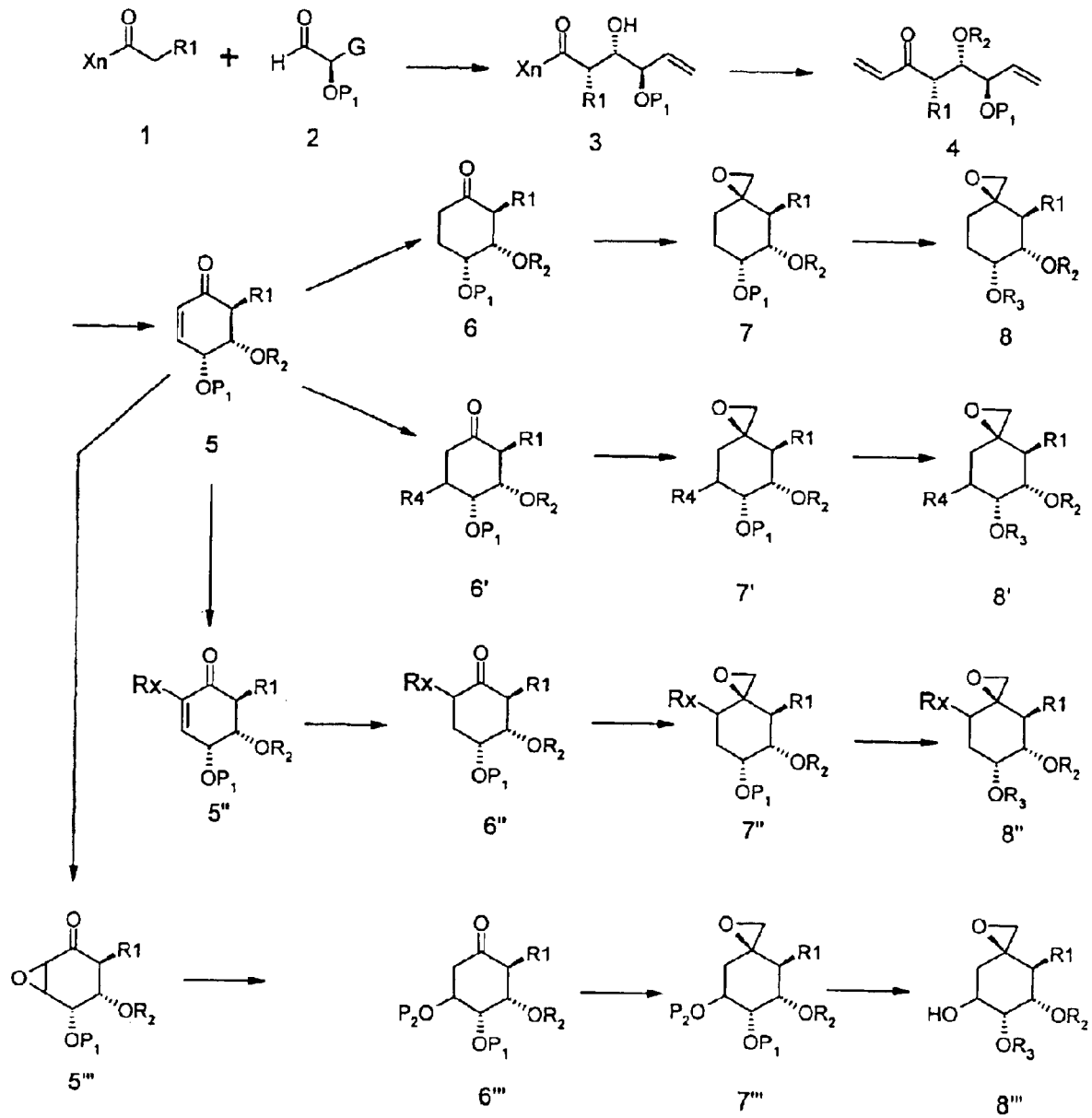
FIG. 1 shows a process for preparing compounds of formula (I) of the present invention.

Thus, the present invention relates to compounds of general formula (I) below:

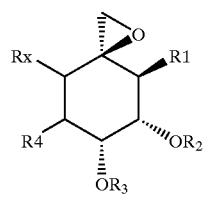

(I)

in which:
Rx represents H, a linear or branched alkyl radical of 1 to 5 carbon atoms or a linear or branched 1-hydroxyalkyl radical 1 to 5 carbon atoms;
$R_1$ represents a linear or branched alkyl radical of 1 to 5 carbon atoms, or an alkenyl radical having the structure (a) or the corresponding epoxide represented by structure (b),

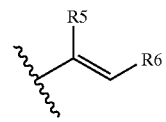

(a)

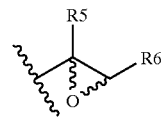

(b)

$R_5$ and $R_6$ having the meanings given below,
$R_2$ is H or a linear alkyl radical of 1 to 5 carbon atoms,
$R_3$ is H or a radical represented by formula (c) or (d),

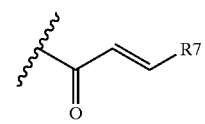

(c)

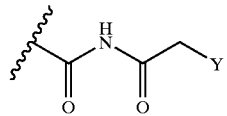

(d)

$R_7$ and Y having the meanings given below,
$R_4$ is H, a linear or branched alkyl radical of 1 to 5 carbon atoms, or a radical $XR_{11}$, $R_4$ is preferably a methyl or ethyl radical,
X and $R_{11}$ having the meanings given below,
$R_5$ is H or a methyl radical,
$R_6$ is H or a linear or branched alkyl radical of 1 to 5 carbon atoms, the radicals $R_5$ and $R_6$, taken together, can form a saturated or unsaturated carbocycle of 3 to 10 carbon atoms such as, for example, a cyclohexene,
$R_7$ is a polyunsaturated chain containing from 5 to 7 carbon atoms and a terminal carboxyl function or an aromatic nucleus corresponding to the general formula (e),

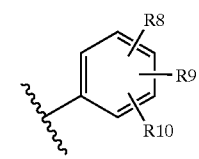

(e)

$R_8$, $R_9$ and $R_{10}$ are, independently, H or $OCH_3$,
$R_{11}$ is H, an alkyl radical of 1 to 5 carbon atoms or an aromatic nucleus,
X represents O or S,
Y represents a halogen atom chosen from chlorine, bromine, iodine and fluorine, given that,
when $R_2$ represents an alkyl of 1 to 5 carbon atoms and $R_4$ represents H, then $R_1$ represents an alkyl of 1 to 5 carbon atoms or an alkenyl having the structure (a) and
when $R_1$ represents the radical (b), then Rx and $R_4$ cannot simultaneously represent H.

The invention is also directed towards the optical and geometrical isomers, the salts and mixtures of the said compounds of formula (I).

Specifically, the compounds of the present invention may be in the form of pharmaceutically or cosmetically acceptable salts, especially in the form of salts of a base, obtained by addition of a base, in particular the sodium salts, the potassium or ammonium salts, or the salts derived from lysine or ethanolamine.

According to the present invention, the expression "alkyl radical of 1 to 5 carbon atoms" means a linear or branched radical containing from 1 to 5 carbon atoms, and preferably methyl, ethyl, isopropyl, tert-butyl and isopentyl radicals.

The term "aromatic nucleus" preferably means the thiophene, pyrrole, naphthalene, benzene or furan radical.

The expression "carbocyclic radicals" means, for example, a saturated or unsaturated ring containing from 3 to 10 carbon atoms, such as, more particularly, a cyclohexene radical.

According to the present invention, the compounds of formula (I) that are more particularly preferred are those for which at least one, and preferably all, of the conditions below are satisfied:

$R_1$ represents the radicals of formula (a) or (b), $R_2$ represents a methyl radical, $R_3$ represents the radical of formula (c), and $R_7$ represents an aromatic nucleus of formula (e).

Among the compounds of formula (I) that fall within the present invention, mention may be made especially of the following:

(3R,4S,5S,6R)-5-methoxy-4-methyl-1-oxaspiro[2,5]oct-6-yl 4-methoxycinnamate;

(3R,4S,5S,6R)-5-methoxy-4-[(E)-1,5-dimethylhexyl]-1-oxaspiro[2,5]oct-6-yl 4-methoxycinnamate;

(3R,4S,5S,6R,7R)-6-hydroxy-5-methoxy-7-methyl-4-[(E)-1,5-dimethylhexyl]-1-oxaspiro[2,5]octane;

(3R,4S,5S,6R,7R)-6-hydroxy-5-methoxy-7-methyl-4-[(1R, 2R)-1,2-epoxy-1,5-dimethylhexyl]-1-oxaspiro[2,5] octane;

(3R,4S,5S,6R,7R)-5-methoxy-7-methyl-4-[(1R,2R)-1,2-epoxy-1,5-dimethylhexyl]-1-oxaspiro[2,5]oct-6-yl 4-methoxycinnamate;

(3R,4S,5S,6R,7R)-7-ethyl-6-hydroxy-5-methoxy-4-[(1R, 2R)-1,2-epoxy-1,5-dimethylhexyl]-1-oxaspiro[2,5] octane;

(3R,4S,5S,6R,7R)-7-ethyl-5-methoxy-4-[(1S,2S)-1,2-epoxy-1,5-dimethylhexyl]-1-oxaspiro[2,5]oct-6-yl 4-methoxycinnamate;

(3R,4S,5S,6R)-4-(cyclohex-1-enyl)-5-methoxy-1-oxaspiro [2,5]oct-6-yl 4-methoxycinnamate;

(3R,4S,5S,6R,7S)-(1,5-dimethylhex-1-enyl)-5-methoxy-7-methyl-1-oxaspiro[2,5]oct-6-yl 4-methoxycinnamate;

(3R,4S,5S,6R,7S)-4-(1,5-dimethylhex-1-enyl)-7-hydroxy-5-methoxy-1-oxaspiro[2,5]oct-6-yl 4-methoxycinnamate;

(3R,4S,5S,6R,8R)-4-(1,5-dimethylhex-1-enyl)-5-methoxy-8-methyl-1-oxaspiro[2,5]oct-6-yl 4-methoxycinnamate;

(3R,4S,5S,6R,7R)-5-methoxy-4-[(1R,2R)-1,2-epoxy-1,5-dimethylhexyl]-7-pentyl-1-oxaspiro[2,5]oct-6-yl 4-methoxycinnamate;

(3R,4S,5S,6R)-5-methoxy-4-methyl-1-oxaspiro[2,5]oct-6-yl 3,4,5-methoxycinnamate;

(3R,4S,5S,6R,7R)-5-methoxy-7-methyl-4-[(1R,2R)-1,2-epoxy-1,5-dimethylhexyl]-1-oxaspiro[2,5]oct-6-yl 3,4,5-methoxycinnamate;

(3R,4S,5S,6R,7R)-7-ethyl-5-methoxy-4-[(1R,2R)-1,2-epoxy-1,5-dimethylhexyl]-1-oxaspiro[2,5]oct-6-yl 3,4,5-methoxycinnamate;

(3R,4S,5S,6R,7R)-5-methoxy-4-[(1R,2R)-1,2-epoxy-1,5-dimethylhexyl]-7-pentyl-1-oxaspiro[2,5]oct-6-yl 3,4,5-methoxycinnamate;

(3R,4S,5S,6R)-4-(cyclohex-1-enyl)-1-oxaspiro[2,5]oct-6-yl 3,4,5-methoxycinnamate;

deca-2,4,6,8-tetraenedioic acid mono{(3R,4S,5S,6R)-5-methoxy-4-methyl-1-oxaspiro[2,5]oct-6-yl} ester;

deca-2,4,6,8-tetraenedioic acid mono{(3R,4S,5S,6R,7R)-5-methoxy-7-methyl-4-[(1R,2R)-1,2-epoxy-1,5-dimethylhexyl]-1-oxaspiro[2,5]oct-6-yl} ester;

deca-2,4,6,8-tetraenedioic acid mono{(3R,4S,5S,6R,7R)-7-ethyl-5-methoxy-4-[(1R,2R)-1,2-epoxy-1,5-dimethylhexyl]-1-oxaspiro[2,5]oct-6-yl} ester;

deca-2,4,6,8-tetraenedioic acid mono{(3R,4S,5S,6R,7R)-5-methoxy-4-[(1R,2R)-1,2-epoxy-1,5-dimethylhexyl]-7-pentyl-1-oxaspiro[2,5]oct-6-yl} ester;

deca-2,4,6,8-tetraenedioic acid mono{(3R,4S,5S,6R)-4-(cyclohex-1-enyl-1-oxaspiro[2,5]oct-6-yl} ester;

chloroacetylcarbamic acid mono{(3R,4S,5S,6R)-5-methoxy-4-methyl-1-oxaspiro[2,5]oct-6-yl} ester;

chloroacetylcarbamic acid mono{(3R,4S,5S,6R)-5-methoxy-4-[(1S,2S)-1,2-epoxy-1,5-dimethylhexyl]-1-oxaspiro[2,5]oct-6-yl} ester;

chloroacetylcarbamic acid mono{(3R,4S,5S,6R,7R)-5-methoxy-7-methyl-4-[(1R, 2R)-1,2-epoxy-1,5-dimethylhexyl]-1-oxaspiro[2,5]oct-6-yl} ester;

chloroacetylcarbamic acid mono{(3R,4S,5S,6R,7R)-7-ethyl-5-methoxy-4-[(1R, 2R)-1,2-epoxy-1,5-dimethylhexyl]-1-oxaspiro[2,5]oct-6-yl} ester;

chloroacetylcarbamic acid mono{(3R,4S,5S,6R,7R)-5-methoxy-4-[(1R,2R)-1,2-epoxy-1,5-dimethylhexyl]-7-pentyl-1-oxaspiro[2,5]oct-6-yl} ester;

acetylcarbamic acid mono{(3R,4S,5S,6R)-4-(cyclohex-1-enyl)-1-oxaspiro[2,5]oct-6-yl} ester.

A subject of the present invention is also processes for preparing the compounds of formula (I), in particular according to the reaction schemes given in FIG. 1.

This figure shows a synthesis first involving an asymmetric aldolization reaction between a chiral derivative of a carboxylic acid bearing a "chiral couple" (1) and an aldehyde (2) that are suitably selected. The aldol (3) thus obtained can then be converted, by standard methods, into a diene derivative (4) which is subjected to a cyclizing metathesis reaction. The cyclic compound obtained (5) may be converted into the cyclohexanone derivative (6). Epoxidation of the ketone (6) to (7) and then, optionally, of the side chain $R_1$, followed by cleavage of the protecting group $P_1$ and esterification of the alcohol thus obtained gives access to the products of general formula (8).

Starting from (5), it is possible to introduce the substituent $R_4$ or Rx by conjugate addition onto the α,β-unsaturated ketone system. The rest of the synthesis is similar to that used to obtain the products (8), and gives in this case the products (8') or (8").

In this figure, the groups $R_1$–$R_4$ and Rx have the values defined above, insofar as they are compatible with the reaction conditions used. In the contrary case, a precursor of the desired group, which will be converted into the said group at the end of the synthesis, may be used. For example, if it is desired for $R_1$ to contain an epoxide, the synthetic steps will be performed using the corresponding olefin, which may be converted at the end of the synthesis into an epoxide by standard methods for oxidizing olefinic double bonds. For example, if, in the final product, the group $R_1$ is the 1,2-epoxy-1,5-dimethylhexyl group, the precursor $R_1$=1, 5-dimethylhex-1-enyl will be used in the synthesis, this latter group being epoxidized at the end of the synthesis.

Thus, the present invention relates to a method for the total synthesis of fumagillin derivatives, comprising the following steps:

(a) asymmetric aldolization between a chiral ester or amide of general formula (1)

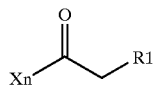
(1)

and an aldehyde of general formula (2)

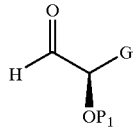
(2)

to obtain the aldol (3);

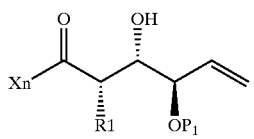
(3)

in which $X_n$ represents a chiral auxiliary;

Non-limiting examples of such auxiliaries that may be mentioned include the Evans chiral oxazolidinones and the Oppolzer chiral sultones.

Non-limiting examples of starting compounds (1) that may be mentioned include:

(4R)-4-benzyl-3-propionyloxazolidin-2-one;
(4R)-4-benzyl-3-(3,7-dimethyloct-3-enoyl)oxazolidin-2-one;
(4R)-4-benzyl-3-(2-cyclohex-1-enylacetyl)oxazolidin-2-one.

$P_1$ represents a protecting group that is compatible with the reaction conditions and that may be removed without affecting the other functions present in the intermediate compounds, so as to allow the introduction of the groups $R_3$ and $R_4$.

Many protecting groups satisfy this definition, for example methoxyethyl-, 2,4-dimethoxybenzyl-, trimethylsilylethyl- and tert-butyldimethylsilyl groups. For example, the p-methoxybenzyl (PMB) group may advantageously be used for $P_1$.

G represents an olefinic double bond or a precursor that can readily be converted into this double bond.

Examples of such precursors that may be mentioned are 2-phenylselenylethyl or 2-phenylsulphenylethyl groups.

Examples of aldehydes (2) that have these characteristics are given below:

2-(R)-4-phenylselenyl-2-p-methoxybenzyloxybutanal;
2-(R)-4-phenylsulphenyl-2-p-methoxybenzyloxybutanal;
2-(R)-4-methoxybenzyloxybut-3-enal.

2-(R)-4-Phenylselenyl-2-p-methoxybenzyloxybutanal will advantageously be used as the starting aldehyde (2).

(b) conversion of the aldol (3) into the diene derivative (4) by standard methods such as a cleavage of the chiral auxiliary with N,O-dimethylhydroxylamine, followed by a reaction with vinylmagnesium bromide, and addition of $R_2$;

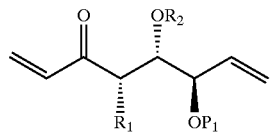
(4)

(c) conversion of the diene derivative (4) by a cyclizing metathesis reaction into the cyclic compound (5);

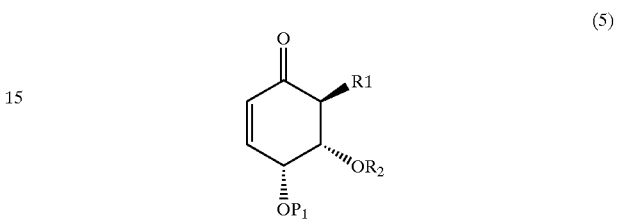
(5)

(d) conversion of the cyclic compound (5) into the cyclohexanone derivative (6) by reduction of the double bond conjugated with the carbonyl group;

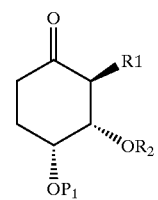
(6)

(e) epoxidation of the cyclohexanone derivative (6) to give the compound of general formula (7);

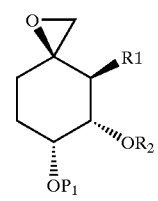
(7)

(f) cleavage of the protecting group $P_1$ and esterification of the alcohol obtained to give (8).

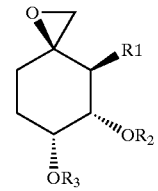
(8)

This method can also include variants for introducing substituents into position 7 or 8 starting with the cyclic compound (5).

For example, this method can include an additional step of conjugate addition of a substituent $R_4$ onto the α,β ketone system of the cyclic compound (5) after step (d).

Such an addition may be performed using various organometallic reagents such as, for example, organolithium reagents, organomagnesium reagents, organocuprates or trialkylaluminiums, optionally in the presence of copper salts and Lewis acids.

The synthetic method may include an additional step after step (c), of introducing a 1-hydroxyalkyl group, precursors of alkyl groups, into position 8 (Rx) of the 1-oxaspiro[2,5] octane ring system via a Baylis-Hillman reaction (see FIG. 1, compound (5")).

The synthetic method may also include an additional step after step (c), of epoxidizing the conjugated double bond located between positions 7 and 8 of the 1-oxaspiro[2,5] octane ring system, followed by its regioselective opening, allowing the introduction of a hydroxyl group into position 7 (see FIG. 1, compound (5'")).

More generally, the well-known reactivity of $\alpha,\beta$-unsaturated ketone systems allows the introduction of a wide variety of substituents into positions 7 and 8 of the 1-oxaspiro[2,5]octane ring system.

Figure 2:
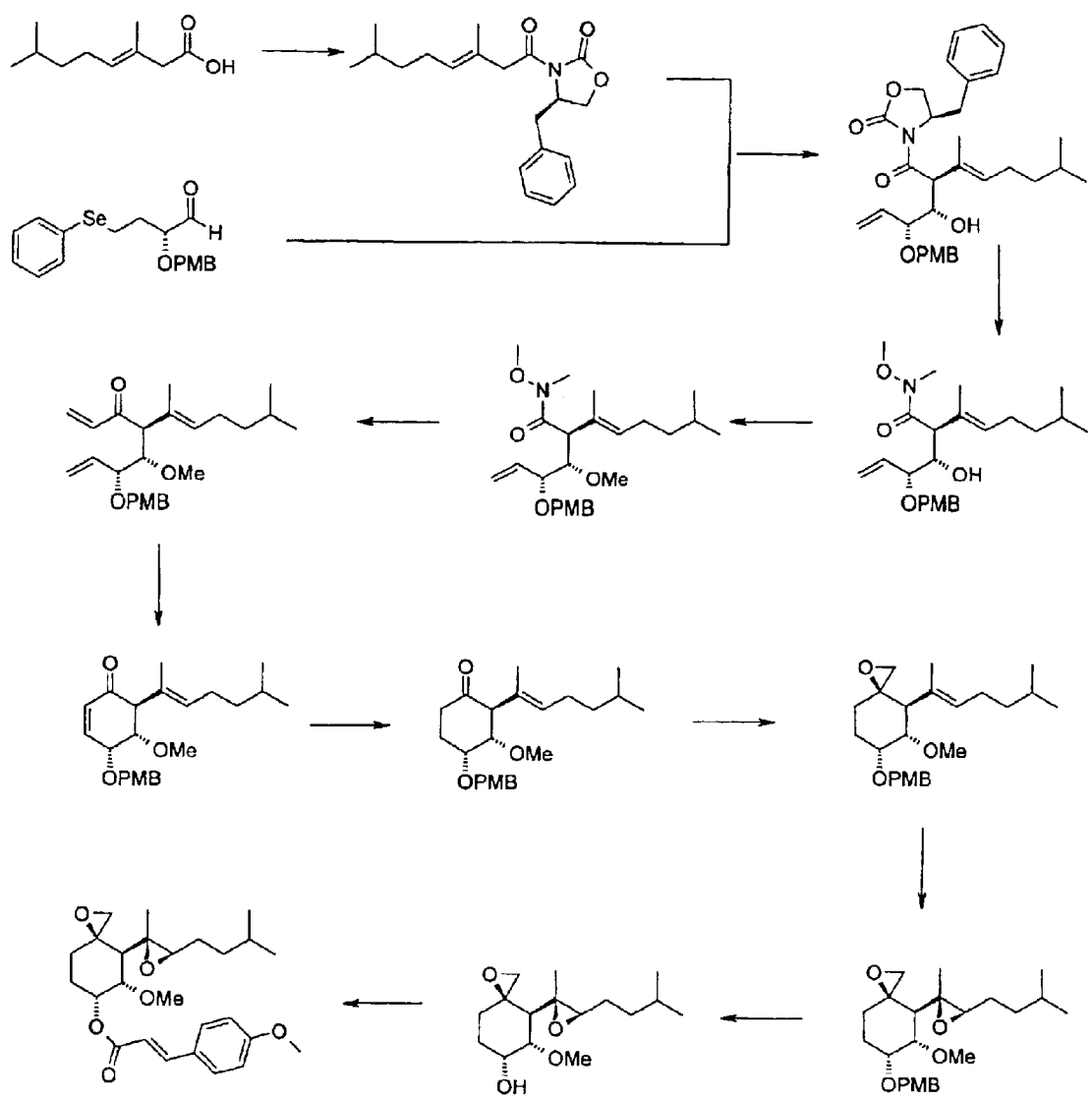
FIG. 2 shows the synthesis of (3R,4S,5S,6R)-5-methoxy-4-[(1R,2R)-1,2-epoxy-1,5-dimethylhexyl]-1-oxaspiro[2,5]oct-6-yl-4-methoxycinnamate.

By way of example, the synthesis of (3R,4S,5S,6R)-5-methoxy-4-[(1R,2R)-1,2-epoxy-1,5-dimethylhexyl]-1-oxaspiro[2,5]oct-6-yl 4-methoxycinnamate is shown in FIG. 2.

The compounds according to the invention have activity in the fields of angiogenesis, cell proliferation and inflammation, and more particularly find applications in the topical and systemic treatment of complaints associated with an angiogenesis or keratinization disorder, complaints with an inflammatory and/or immunoallergic component and hyperproliferation of tissues of ectodermal origin (especially skin and epithelium), whether benign or malignant, and also find an application in fields unrelated to dermatology.

These compounds may also be used to combat ageing of the skin, whether light-induced or chronological ageing, and to treat cicatrization disorders.

The compounds of general formula (I) have biological, anti-angiogenic, antiproliferative and anti-inflammatory properties. This activity may be demonstrated "in vitro" by a method using a biological target, a methionine aminopeptidase (MetAP-2) identified by Griffith et al. (Griffith, E. C. et al. *Chem. Biol.*, 1997, 4(6), 461–471). The inhibitory activity of various fumagillin derivatives on this enzyme shows good correlation with the anti-angiogenic effect.

By way of example, the biological activity of the compounds is evaluated by measuring their inhibitory activity on methionine aminopeptidase MetAP-2 (Li, X., Chang, Y-H. *Biochem. Biophys. Res. Comm.* 1996, 227, 152).

The biological activity is characterized in this system by determining the concentration of compound required to inhibit 50% of the enzymatic activity ($IC_{50}$). The test protocol used is described in Example 13 of the present patent application.

The anti-angiogenic activity of the compounds according to the invention may also be measured by means of their capacity to inhibit the proliferation of endothelial cells. This activity is determined in Example 13 of the present patent application.

A subject of the present invention is also a pharmaceutical composition comprising at least one compound of formula (I) as defined above, in a pharmaceutically acceptable support.

A subject of the present invention is thus also such a pharmaceutical composition as a medicinal product intended especially for treating the abovementioned complaints.

The compositions according to the invention may be administered via the oral, parenteral, topical or ocular route.

Via the oral route, the pharmaceutical compositions may be in the form of tablets, gel capsules, coated tablets, syrups, suspensions, solutions, powders, granules, emulsions, or suspensions of lipid or polymer microspheres or nanospheres or vesicles allowing a controlled release.

Via the parenteral route, the compositions may be in the form of solutions or suspensions for infusion or for injection.

The compounds according to the invention are generally administered at a daily dose of from about 0.001 mg/kg to 500 mg/kg and preferably from about 0.01 mg/kg to 50 mg/kg of body weight, in 1 to 3 dosage intakes.

Via the topical route, the pharmaceutical compositions based on compounds according to the invention are intended for treating the skin and mucous membranes and are in the form of ointments, creams, milks, salves, powders, impregnated pads, solutions, gels, sprays, lotions or suspensions. They may also be in the form of suspensions of lipid or polymer microspheres or nanospheres or vesicles, or polymer patches and hydrogels allowing a controlled release. These topical compositions may be either in anhydrous form or in aqueous form depending on the clinical indication.

Via the ocular route, they are mainly eye lotions.

These pharmaceutical compositions of the present invention, especially for the topical or ocular route, contain at least one compound of formula (I) as defined above at a concentration preferably of between 0.0001% and 20% and preferably between 0.001% and 5%, relative to the total weight of the composition.

A subject of the present invention is also, as medicinal products, the pharmaceutical compositions as defined above.

The pharmaceutical compositions of the present invention are particularly suitable for treating complaints associated with an angiogenesis disorder or with cell proliferation, with or without an inflammatory nature, such as haemangiomas, benign or malignant tumours, cancers, melanomas, basal cell carcinomas, pyogenic granuloma, angiofibromas, scleroderma, ocular tumours, chorioretinal ischaemia, retinal neovascularization, neovascular glaucoma, trachomatous scars, rheumatoid diseases, rheumatoid arthritis, psoriasis, Kaposi's sarcoma, angiosarcoma, lupus, rosacea, proliferative retinopathy of diabetic origin, graft rejection, and cicatrization disorders such as cheloids and hypertrophic scars.

The compounds of formula (I) according to the invention also find an application in the cosmetic field, in particular in skin care or scalp care and especially for treating acne-prone skin, for the regrowth of hair, to prevent hair loss, to combat the greasy appearance of the skin or the hair, in protecting against the harmful effects of sunlight or in treating physiologically dry skin, and to prevent and/or combat light-induced or chronological ageing.

The present invention is thus also directed towards a cosmetic composition containing, in a cosmetically acceptable support, at least one compound of formula (I) as defined above.

This cosmetic composition may especially be in the form of a cream, a milk, a lotion, a gel, suspensions of lipid or polymer microspheres or nanospheres or vesicles, a soap or a shampoo.

The concentration of compound of formula (I) in the cosmetic compositions may be between 0.0001% and 3% by weight relative to the total weight of the composition.

The compounds according to the invention may also be used in cosmetic compositions for body and hair hygiene.

In the pharmaceutical and cosmetic fields, the compounds according to the invention may be advantageously used in combination with retinoids, with corticosteroids or oestrogens, in combination with free-radical scavengers, with $\alpha$-hydroxy or $\alpha$-keto acids or derivatives thereof, with salicylic acid derivatives, or alternatively with ion-channel blockers such as potassium-channel blockers, or alternatively, more particularly for pharmaceutical compositions, in combination with medicinal products known to interfere with the immune system (for example cyclosporin, FK 506, glucocorticoids, monoclonal antibodies, cytokines or growth factors, etc.).

The term "retinoids" means natural or synthetic RAR or RXR receptor ligands.

The term "antioxidants" means, for example, α-tocopherol, superoxide dismutase, ubiquinol or certain metal-chelating agents.

The expression "α-hydroxy or α-keto acids or derivatives thereof" means, for example, lactic acid, malic acid, citric acid, glycolic acid, mandelic acid, tartaric acid, glyceric acid or ascorbic acid, and also the salts, amides or esters thereof.

The expression "potassium-channel blockers" means, for example, Minoxidil (2,4-diamino-6-piperidinopyrimidine 3-oxide) and its derivatives.

The pharmaceutical and cosmetic compositions according to the invention may also contain inert or even pharmacodynamically or cosmetically active additives or combinations of these additives, and especially:

wetting agents;

depigmenting agents such as hydroquinone, azelaic acid, caffeic acid or kojic acid;

emollients;

moisturizers such as glycerol, PEG 400, thiamorpholinone and its derivatives or urea;

anti-seborrhoeic or anti-acne agents, such as S-carboxymethylcysteine, S-benzylcysteamine, salts thereof and derivatives thereof, or benzoyl peroxide;

antibiotics, for instance erythromycin and its esters, neomycin, clindamycin and its esters, and tetracyclines;

antifungal agents such as ketoconazole or poly-4,5-methyleneisothiazolin-3-ones;

agents for promoting regrowth of the hair, for instance Minoxidil (2,4-diamino-6-piperidinopyrimidine 3-oxide) and its derivatives, Diazoxide (7-chloro-3-methyl-1,2,4-benzothiadiazine 1,1-dioxide) and Phenytoin (5,4-diphenylimidazolidine-2,4-dione);

non-steroidal anti-inflammatory agents;

carotenoids and especially β-carotene;

anti-psoriatic agents such as anthralin and its derivatives;

and finally, eicosa-5,8,11,14-tetraynoic acid and eicosa-5,8,11-triynoic acid, esters thereof and amides thereof.

The pharmaceutical and cosmetic compositions according to the invention may also contain flavour enhancers, preserving agents such as para-hydroxybenzoic acid esters, stabilizers, moisture regulators, pH regulators, osmotic pressure modifiers, emulsifiers, UV-A and UV-B screening agents, and antioxidants such as α-tocopherol, butylhydroxyanisole or butylhydroxytoluene.

Several examples of the production of active compounds of formula (I) according to the invention, and also various concrete formulations based on such compounds and examples of tests to evaluate the biological activity of compounds of formula (I) according to the invention, will now be given by way of illustration and with no limiting nature.

EXAMPLES

Preliminary Preparation of Methyl 2-(R)-4-phenylselenyl-2-hydroxybutanoate

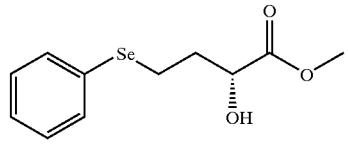

A solution of 29 g (93 mmol, 1.0 eq) of diphenyl diselenide in 150 mL of DMF is added slowly to a solution of 7.04 g (186 mmol, 2.0 eq) of sodium borohydride in 100 mL of DMF. The reaction medium is stirred at 20° C. until decolourized and the temperature is then raised to 80° C. A solution of 9.50 g (93 mmol, 1.0 eq) of (R)-(+)-α-hydroxybutyrolactone in 25 mL of DMF is added slowly at 80° C. using a cannula. The reaction mixture is stirred for two hours at 80° C. and then for one hour at 20° C. The reaction is quenched by adding 1M hydrochloric acid solution and then extracted with diethyl ether. The organic phases are washed with saturated sodium chloride solution and then dried over anhydrous sodium sulphate. The solvents are evaporated off and the residual oil is then dissolved in diethyl ether and treated with an excess of diazomethane. The reaction progress is monitored by thin layer chromatography (TLC): eluent (1/1 Cyclohexane (Cy)/Ethyl Acetate (EtOAc)). After evaporation of the solvents, the oil obtained is chromatographed on silica gel: eluent: (8/2 Cy/EtOAc).

18.7 g of colourless oil are obtained. Yield=74%.

$R_f$=0.22 (7/3 Cy/EtOAc).

$[\alpha]_D^{20}$=+6° (CHCl$_3$, C=1.18)

$^1$H NMR (250 MHz, CDCl$_3$): 7.49 (m, 2H, ArH); 7.26 (m, 3H, ArH); 4.32 (ddd, J=8, 5.3, 4.0, 1H, CHOH); 3.77 (s, 3H, OCH$_3$); 3.01 (dd, J=8.0, 7.2, 2H, SeCH$_2$); 2.79 (d, J=5.3, 1H, OH); 2.16 & 2.03 (2m, 2H, CH$_2$).

$^{13}$C NMR (62.9 MHz, CDCl$_3$): 175.0, 132.4, 129.6, 129.0, 126.8, 69.7, 52.5, 34.5, 22.6.

Methyl 2-(R)-4-phenylselenyl-2-p-methoxybenzyloxybutanoate

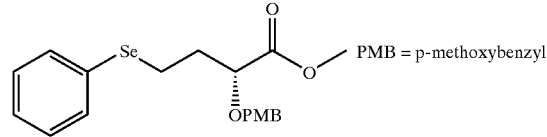

3.2 g (13.7 mmol, 0.2 eq) of CSA (camphorsulphonic acid) are added to a solution of 18.7 g (68.5 mmol, 1.0 eq) of methyl 2-(R)-4-phenylselenyl-2-hydroxybutanoate in 150 mL of dichloromethane in the presence of 38.7 g (137 mmol, 2.0 eq) of freshly prepared PMB acetimidate. The reaction mixture is stirred for 24 hours at room temperature. The reaction is quenched by adding saturated sodium hydrogen carbonate solution and then extracted with ethyl acetate. The organic phases are combined and dried over anhydrous sodium sulphate, and the solvents are then evaporated off. The residue is chromatographed on silica gel: eluent (9/1→8/2 Cy/EtOAc).

18.94 g of colourless oil are obtained. Yield=70%.

$R_f$=0.48 (8/2 Cy/EtOAc).

Elemental analyses: Calculated: C=58.02%; H=5.64%

Measured: C=58.12%; H=5.65%

$^1$H NMR (250 MHz, CDCl$_3$): 7.47 (m, 2H, ArH); 7.26 (m, 5H, ArH); 6.86 (d, J=8.5, 2H, ArH); 4.62 & 4.29 (2d, J=11.0,

2H, OCH$_2$Ar); 4.10 (dd, J=4.5, 8, 1H, CHCOOMe); 3.80 (s, 3H, OCH$_3$); 3.75 (s, 3H, COOCH$_3$); 2.97 (m, 2H, SeCH$_2$); 2.10 (m, 2H, SeCH$_2$CH$_2$).

$^{13}$C NMR (62.9 MHz, CDCl$_3$): 172.9, 159.4, 132.6, 129.7, 129.3, 129.0, 126.9, 113.7, 76.6, 72.1, 55.2, 51.9, 33.4, 23.3.

2-(R)-4-phenylselenyl-2-p-methoxybenzyloxybutanal

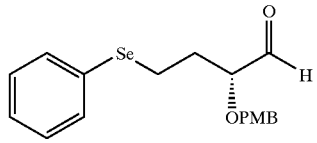

20.4 mL (30.6 mmol, 1.5 eq) of a 1.5 M solution of DIBAH (diisobutylaluminium hydride) in toluene are introduced at −78° C. into a solution of 7.8 g (19.8 mmol, 1.0 eq) of methyl 2-(R)-4-phenylselenyl-2-p-methoxybenzyloxybutanoate in 50 mL of toluene. The reaction medium is stirred for 20 minutes at −78° C. and 10 mL of methanol are then added cautiously. The cooling bath is removed, allowing the temperature to rise slowly to room temperature. After a white precipitate has formed, 0.5 mL of saturated sodium tartrate solution is added, followed by addition of 100 mL of ethyl acetate and 1 g of anhydrous magnesium sulphate. The reaction mixture is stirred for one hour at room temperature and then filtered. The solid is washed with 3×100 mL of ethyl acetate. The solvents are evaporated off and the residue is then chromatographed on silica: eluent (8/2 Cy/EtOAc).

6.75 g of yellowish oil are obtained. Yield=94%

R$_f$=0.38 (8/2 Cy/EtOAc).

$^1$H NMR (250 MHz, CDCl$_3$): 9.64 (d, 1H, J=1.6, CHO); 7.48 (m, 2H, ArH); 7.25 (m, 5H, ArH); 6.88 (d, J=8.7, 2H, ArH); 4.48 & 4.44 (2d, J=11.2, 2H, OCH$_2$Ar); 3.93 (ddd, J=7.0, 5.2, 1.6, 1H, CHCHO); 3.80 (s, 3H, OCH$_3$); 2.99 (m, 2H, SeCH$_2$); 2.02 (m, 2H, SeCH$_2$CH$_2$).

$^{13}$C NMR (62.9 MHz, CDCl$_3$): 203.0, 159.5, 132.7, 129.7, 129.1, 129.0, 127.0, 113.9, 82.2, 72.3, 55.2, 30.6, 22.8.

Example 1

(3R,4S,5S,6R)-5-methoxy-4-methyl-1-oxaspiro[2,5]oct-6-yl 4-methoxycinnamate

1. Preparation of (4R)-4-benzyl-3-[(2S,3S,4R)-2-methyl-3-hydroxy-4-p-methoxybenzyloxy-6-phenylselenylhexanoyl]-2-oxazolidinone

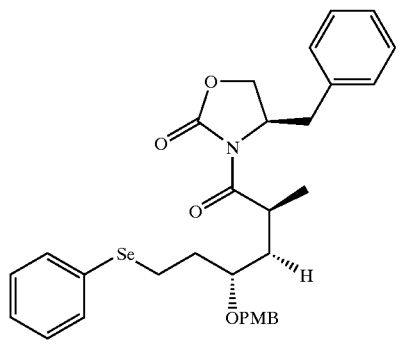

4 mL (6.41 mmol, 1.1 eq) of a 1.6 M solution of BuLi in hexane are added at 0° C. to a solution of 0.91 mL (6.41 mmol, 1.1 eq) of diisopropylamine in 2 mL of THF. The reaction medium is stirred for 15 minutes at 0° C. and then cooled to −78° C. A solution of 1.36 g (5.83 mmol, 1.0 eq) of (4R)-4-benzyl-3-propionyloxazolidin-2-one in 3 mL of THF is added using a cannula. After stirring for 30 minutes at −78° C., a solution of 2.18 g (5.96 mmol, 1.02 eq) of 2-(R)-4-phenylselenyl-2-p-methoxybenzyloxybutanal in 3 mL of THF is added using a cannula. The reaction mixture is stirred for 30 minutes at −78° C. and the reaction is then quenched by adding 10 mL of saturated ammonium chloride solution. The flask is warmed to room temperature and then extracted with diethyl ether. The organic phases are combined and then dried over anhydrous sodium sulphate. After evaporating off the solvents, the residue is chromatographed on silica gel: eluent (9/1→75/25 Cy/EtOAc).

2.54 g of gelatinous solid containing the two diastereoisomers (4R)-4-benzyl-3-[(2S,3S,4R)-2-methyl-3-hydroxy-4-p-methoxybenzyloxy-6-phenylselenylhexanoyl]-2-oxazolidinone and (4R)-4-benzyl-3-[(2R,3R,4R)-2-methyl-3-hydroxy-4-p-methoxybenzyloxy-6-phenylselenylhexanoyl]-2-oxazolidinone, are obtained in a 7/3 ratio, respectively. Yield=73%.

R$_f$=0.24 (7/3 Cy/EtOAc).

M=620.1 (M+Na).

Spectra of (4R)-4-benzyl-3-[(2S,3S,4R)-2-methyl-3-hydroxy-4-p-methoxybenzyloxy-6-phenylselenylhexanoyl]-2-oxazolidinone.

$^1$H NMR (250 MHz, CDCl$_3$): 7.50–7.46 (m, 2H, ArH); 7.35–7.16 (m, 10H, ArH); 6.86 (d, J=8.5, 2H, ArH); 4.59 (dddd, J=3.2, 3.2, 6.6, 10.4, 1H, CHN); 4.45 (AB, 2H, CH$_2$pC$_6$H$_4$OMe); 4.19–4.06 (3m, 4H, CHOH, NCOCHCH$_3$ & NCOOCH$_2$); 3.76 (s, 3H, OCH$_3$); 3.54 (bq, J=5.8, 1H, CHOPMB); 3.27 (dd, J=3.2, 13.3. 1H, CHPh); 3.04 (m, 2H, SeCH$_2$); 2.80 (d, J=2.2, 1H, OH); 2.47 (dd, J=10.2, 13.3, 1H, CHPh); 2.11 (m, 2H, SeCH$_2$CH$_2$); 1.19 (d, J=6.5, 3H, CH$_3$).

$^{13}$C NMR (62.9 MHz, CDCl$_3$): 177.4, 159.4, 152.7, 135.4, 132.2, 130.6, 130.0, 130.0, 129.3, 129.1, 129.0, 127.3, 126.6, 113.9, 77.4, 71.9, 71.5, 66.0, 55.4, 55.2, 38.9, 37.9, 30.3, 23.0, 12.0.

Spectrum of (4R)-4-benzyl-3-[(2R,3R,4R)-2-methyl-3-hydroxy-4-p-methoxybenzyloxy-6-phenylselenylhexanoyl]-2-oxazolidinone.

$^1$H NMR (250 MHz, CDCl$_3$): 7.51–7.47 (m, 2H, ArH); 7.34–7.17 (m, 10H, ArH); 6.85 (d, J=8.5, 2H, ArH); 4.61 (dddd, J=3.5, 3.5, 7.2, 11.0, 1H, CHN); 4.53 & 4.40 (2d, J=11.2, 2H, CH$_2$pC$_6$H$_4$OMe); 4.12 (ABC, 2H, NCOOCH$_2$); 3.94 (2m, 2H, CHOH, NCOCHCH$_3$); 3.79 (s, 3H, OCH$_3$); 3.51 (bq, J=5.7, 1H, CHOPMB); 3.22 (dd, J=3.2, 13.3, 1H, CHPh); 3.04 (t, J=7.2, 2H, SeCH$_2$); 2.44 (dd, J=10.3, 13.3, 1H, CHPh); 2.39 (d, J=7.6, 1H, OH); 2.06 (m, 2H, SeCH$_2$CH$_2$); 1.25 (d, J=6.5, 3H, CH$_3$).

2. Preparation of (4R)-4-benzyl-3-[(2S,3S,4R)-2-methyl-3-hydroxy-4-p-methoxybenzyloxyhex-5-enoyl]-2-oxazolidinone

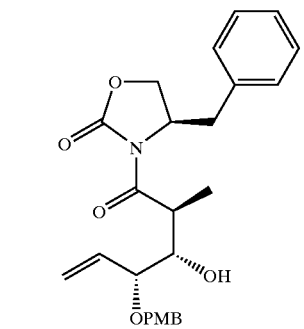

2.41 g (4.0 mmol, 1.0 eq) of a 7/3 mixture of (4R)-4-benzyl-3-[(2S,3S,4R)-2-methyl-3-hydroxy-4-p- methoxybenzyloxy-6-phenylselenylhexanoyl]-2-oxazolidinone and (4R)-4-benzyl-3-[(2R,3R,4R)-2-methyl-3-hydroxy-4p-methoxybenzyloxy-6-phenylselenylhexanoyl]-2-oxazolidinone are dissolved in 25 mL of chloroform in the presence of 2.45 g (5.6 mmol, 1.4 eq) of tetrabutylammonium periodate. The reaction is stirred at 65° C. for three hours. The chloroform is evaporated off and the residue is then chromatographed on silica gel: eluent (7/3 Cy/EtOAc).

461 g of (4R)-4-benzyl-3-[(2R,3R,4R)-2-methyl-3-hydroxy-4-p-methoxybenzyloxyhex-5-enoyl]-2-oxazolidinone. Yield=26%.

1.1 g de (4R)-4-benzyl-3-[(2S,3S,4R)-2-methyl-3-hydroxy-4-p-methoxybenzyloxyhex-5-enoyl]-2-oxazolidinone ($R_f$=0.17 (7/3 Cy/EtOAc)). Yield=62%.

$[\alpha]_D^{20}$=−29° (CHCl$_3$, C=1.15).

$^1$H NMR of (4R)-4-benzyl-3-[(2S,3S,4R)-2-methyl-3-hydroxy-4-p-methoxybenzyloxyhex-5-enoyl]-2-oxazolidinone (250 MHz, CDCl$_3$): 7.34–7.15 (m, 7H, ArH); 6.87 (d, J=8.5, 2H, ArH); 5.89 (ddd, J=7.7, 9, 17.7, 1H, CH=CH$_2$); 5.43 and 5.36 (2d, J=9, J=17.7, 2H, CH$_2$=CH); 4.57 (m, 1H, PhCH$_2$CHN); 4.56 and 4.29 (2d, J=11.2, 2H, CH$_2$pC$_6$H$_4$OMe); 4.18–4.04 (3m, 4H, CHOH, NCOCHCH$_3$, NCOOCH$_2$); 3.79–72 (m, 1H, CHOPMB); 3.76 (s, 3H, OCH$_3$); 3.23 (dd, J=3, 13.2, 1H, CHPh); 2.67 (d, J=3.2, 1H, OH); 2.39 (dd, J=10.2, 13.2, 1H, CHPh); 1.17 (d, J=6.7, 3H, CH$_3$).

$^{13}$C NMR of (4R)-4-benzyl-3-[(2S,3S,4R)-2-methyl-3-hydroxy-4-p-methoxybenzyloxyhex-5-enoyl]-2-oxazolidinone (62.9 MHz, CDCl$_3$) 176.9, 159.3, 152.7, 135.7, 135.4, 130.0, 129.8, 129.3, 128.9, 127.2, 120.0, 113.8, 80.7, 73.0, 70.1, 65.9, 55.4, 55.2, 39.4, 37.7, 11.9.

$^1$H NMR of (4R)-4-benzyl-3-[(2R,3R,4R)-2-methyl-3-hydroxy-4-p-methoxybenzyloxyhex-5-enoyl]-2-oxazolidinone (250 MHz, CDCl$_3$): 7.34–7.18 (m, 7H, ArH); 6.88 (d, J=8.5, 2H, ArH); 5.89 (ddd, J=8.5, 10.2, 17.2, 1H, CH=CH$_2$); 5.42 and 5.35 (2d, J=10.2, J=17.2, 2H, CH$_2$=CH); 4.64 (m, 1H, PhCH$_2$CHN); 4.60 and 4.28 (2d, J=11.5, 2H, CH$_2$pC$_6$H$_4$OMe); 4.15–4.01 (2m, 3H, CHOH, NCOOCH$_2$); 3.93 (dq, J=6.7, 5.2, 1H, NCOCHCH$_3$); 3.79 (s, 3H, OCH$_3$); 3.76 (dd, J=6.2, 8.4, 1H, CHOPMB); 3.22 (dd, J=3.2, 13.2, 1H, CHPh); 2.60 (d, J=4.5, 1H, OH); 2.42 (dd, J=10.2, 13.2, 1H, CHPh); 1.21 (d, J=6.7, 3H, CH$_3$).

$^{13}$C NMR of (4R)-4-benzyl-3-[(2R,3R,4R)-2-methyl-3-hydroxy-4-p-methoxybenzyloxyhex-5-enoyl]-2-oxazolidinone (62.9 MHz, CDCl$_3$): 175.1, 159.8, 135.4, 134.7, 129.7, 129.3, 128.9, 127.2, 120.6, 113.8, 81.7, 73.4, 69.6, 66.1, 40.1, 37.7, 11.0.

3. Preparation of (2S,3S,4R)-3-hydroxy-4-p-methoxybenzyloxy-2-methylhex-5-enoic acid methoxymethylamide

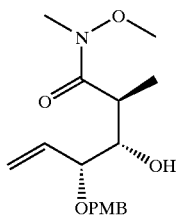

3.41 mL (6.82 mmol, 3.0 eq) of a 2 M solution of trimethylaluminium in toluene are added at 0° C. to a suspension of 665 mg (6.82 mmol, 3.0 eq) of N,O-dimethylhydroxylamine hydrochloride in 2 mL of THF (considerable evolution of gas). The solution obtained is stirred for 30 minutes at room temperature. A solution of 1.0 g (2.27 mmol, 1.0 eq) of (4R)-4-benzyl-3-[(2S,3S,4R)-2-methyl-3-hydroxy-4-p-methoxybenzyloxyhex-5-enoyl]-2-oxazolidinone in 4 mL (plus 1 mL of rinsing) of THF is added at −10° C. The reaction medium is stirred for two hours at 0° C. The reaction is transferred using a cannula into a 30% tartaric acid solution and then extracted with ethyl acetate. The organic phases are combined and dried over anhydrous sodium sulphate, and the solvents are then evaporated off. The residue is chromatographed on silica gel: eluent (7/3 Cy/EtOAc).

646 mg of gelatinous white solid are obtained. Yield=87%.

$R_f$=0.27 (6/4 Cy/EtOAc).

$[\alpha]_D^{20}$=−5.5° (CHCl$_3$, C=1.10)

M=346.1 (M+Na)

$^1$H NMR (250 MHz, CDCl$_3$): 7.24 & 6.88 (2d, J=8.5, 4H, ArH); 5.86 (ddd, J=7.7, 10.2, 17.3, 1H, CH=CH$_2$); 5.38 & 5.33 (2dm, J=10.5 & J=17.0, 2H, CH$_2$=CH); 4.55 & 4.29 (2d, J=11.2, 2H, CH$_2$pC$_6$H$_4$OMe); 3.91 (ddd, J=2.0, 4.2, 7.2, 1H, CHOH); 3.80 (s, 3H, ArOCH$_3$); 3.75 (tl, J=7.5, 1H, CHOPMB); 3.67 (s, 3H, OCH$_3$); 3.55 (d, J=2.0, 1H, OH); 3.25–3.14 (m, 1H, CHCH$_3$); 3.16 (s, 3H, NCH$_3$); 1.09 (d, J=7.1, 3H, CH$_3$).

$^{13}$C NMR (62.9 MHz, CDCl$_3$): 173.5, 159.1, 135.8, 130.3, 129.4, 119.7, 110.1, 79.7, 73.4, 69.8, 61.4, 55.2, 35.6. 31.9 (I), 10.9.

4. Preparation of (2S,3S,4R)-3-methoxy-4-p-methoxybenzyloxy-2-methylhex-5-enoic acid methoxymethylamide

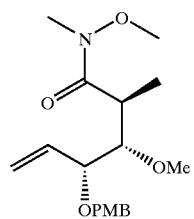

0.52 mL (8.34 mmol, 10 eq) of methyl iodide is added to a solution of 270 mg (0.834 mmol, 1.0 eq) of (2S,3S,4R)-3-hydroxy-4-p-methoxybenzyloxy-2-methylhex-5-enoic acid methoxymethylamide in 4 mL of THF in the presence of 1.5 mL of DMF. The reaction mixture is cooled to 0° C. and 83 mg (20.9 mmol, 2.5 eq) of a 60% dispersion of NaH in oil are added. The reaction medium is stirred for one hour at 0° C. 2 mL of a pH 7 buffer solution are added to quench the reaction, and the reaction mixture is then extracted with 3×40 mL of methylene chloride.

The organic phases are combined, dried over sodium sulphate and then concentrated to give a colourless oil, which is then chromatographed on silica gel; eluent: (6/4 Cy/EtOAc).

270 mg of colourless oil are obtained. Yield=96%.

$[\alpha]_D^{20}$=−38° (CHCl$_3$, C=1.0)

$^1$H NMR (250 MHz, CDCl$_3$): 7.24 & 6.85 (2d, J=8.7, 4H, ArH); 5.88 (ddd, J=7.6, 10.4, 17.3, 1H, CH$_2$=CHCHOPMB); 5.32 (bd, J=10.4, 1H, CH$_2$=CHCHOPMB); 5.26 (bd, J=17.3, 1H, CH$_2$=CHCHOPMB); 4.51 and 4.31 (2d, J=11.4, 2H, OCH$_2$pC$_6$H$_4$OMe); 3.79 (s, 3H, ArOCH$_3$); 3.77 (dd, J=7.6, 4.3, 1H, CHOPMB); 3.63 (dd, J=4.3, 8.2, 1H, CHOMe); 3.59 (s, 3H, NOCH$_3$); 3.50 (s, 3H, OCH$_3$); 3.09 (s, 3H, NCH$_3$); 3.04 (m, 1H, CHCH$_3$); 1.18 (d, J=7, 3H, CHCH$_3$).

$^{13}$C NMR (62.9 MHz, CDCl$_3$): 158.9, 135.5, 130.6, 129.0, 119.1, 113.5, 84.0, 82.1, 69.9, 61.2, 60.8, 37.8, 32.3, 13.6.

5. Preparation of (4S,5S,6R)-6-p-methoxybenzyloxy-4-methylocta-5-methoxy-1,7-dien-3-one

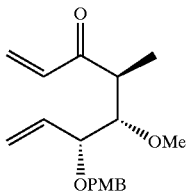

3.56 mL (3.56 mmol, 4.0 eq) of a 1M solution of vinylmagnesium bromide in THF are added at 0° C. to a solution of 300 mg (0.89 mmol, 1.0 eq) of (2S,3S,4R)-3-methoxy-4-p-methoxybenzyloxy-2-methylhex-5-enoic acid methoxymethylamide in 5 mL of THF. The reaction mixture is stirred for two hours at room temperature and then poured rapidly onto a mixture of 25 mL of saturated ammonium chloride solution in the presence of 25 mL of diethyl ether, with vigorous stirring. The mixture is extracted with 3×25 mL of diethyl ether and the organic phases are combined, dried over sodium sulphate and then concentrated to give a colourless oil, which is then chromatographed on silica gel: eluent (8/2 Cy/EtOAc).

237 mg of colourless oil are obtained. Yield=87%.

$[\alpha]_D^{20}$=−23.6° (CHCl$_3$, C=1.1)

$^1$H NMR (250 MHz, CDCl$_3$): 7.21 and 6.85 (2d, J=8.7, 4H, ArH); 6.40 (dd, J=10.2, 17.5, 1H, CH$_2$=CHCO); 6.21 (dd, J=1.6, 17.5, 1H, CH$_2$=CHCO); 5.83 (ddd, J=7.4, 10.4, 17.5, 1H, CH2=CHCHOPMB); 5.73 (dd, J=1.6, 10.2, 1H, CH$_2$=CHCO); 5.35 (dm, J=10.2, 1H, CH2=CHCHOPMB); 5.21 (dm, J=17.5, 1H, CH$_2$=CHCHOPMB); 4.48 and 4.24 (2d, J=11.4, 2H, CHOCH$_2$pC$_6$H$_4$OMe); 3.79 (s, 3H, ArOCH$_3$); 3.63 (m, 2H, CHOPMB and CHOMe); 3.38 (s, 3H, OCH$_3$); 3.08 (dq, J=5.8, 7.0, 1H, CHCH$_3$); 1.08 (d, J=7.0, 3H, CHCH$_3$).

$^{13}$C NMR (62.9 MHz, CDCl$_3$): 202.4, 159.0, 135.8, 135.3, 130.2, 129.3, 128.2, 119.5, 113.6, 83.5, 81.0, 69.8, 60.4, 55.2, 45.5, 11.5.

6. Preparation of (4R,5S,6S)-4-p-methoxybenzyloxy-6-methyl-5-methoxycyclohex-2-enone

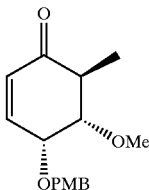

65 µl (0.22 mmol, 0.3 eq) of Ti(OiPr)$_4$ are added to a solution of 225 mg (0.74 mmol, 1.0 eq) of (4S,5S,6R)-6-p-methoxybenzyloxy-4-methylocta-5-methoxy-1,7-dien-3-one in 10 mL of dichloromethane. The reaction mixture is heated for 30 minutes at 40° C. and 60 mg (74 µmol, 0.1 eq) of Grubbs complex are then added to the solution. The reaction mixture is heated for eight hours at 40° C., a further 25 mg of Grubbs complex are added and the reaction mixture is then heated for a further 16 hours at 40° C. The reaction is quenched by adding 5 mL of pH 7 buffer and the resulting mixture is then extracted with diethyl ether. The organic phases are combined, dried over sodium sulphate and then concentrated to give a colourless oil, which is then chromatographed on silica gel: eluent (65/35 Cy/EtOAc)

121 mg of colourless oil are obtained. Yield=59%.

R$_f$=0.38 (65/35 Cy/EtOAc)

$[\alpha]_D^{20}$=−142° (CHCl$_3$, C=1.0)

$^1$H NMR (250 MHz, CDCl$_3$): 7.31 and 6.90 (2d, J=8.6, 4H, ArH); 6.80 (ddd, J=0.7, 4.3, 10.1, 1H, CH=CHCHOPMB); 6.02 (dd, J=1, 10.1, 1H, CH=CHCHOPMB); 4.68 (AB, J=11.8, 2H, OCH$_2$pC$_6$H$_4$OMe); 4.31 (ddd J=1, 3.3, 4.3, 1H, CHOPMB); 3.81 (s, 3H, ArOCH$_3$); 3.43 (s, 3H, OCH$_3$); 3.41 (dd, J=3.3, 8, 1H, CHOCH$_3$); 2.94 (qd, J=7.1, 8, 1H, CHCH$_3$); 1.17 (d, J=7.1, 3H, CHCH$_3$).

$^{13}$C NMR (62.9 MHz, CDCl$_3$): 200.2, 159.5, 144.4, 130.3, 130.0, 129.5, 113.9, 82.7, 71.7, 69.3, 57.7, 55.3, 44.1, 11.7.

7. Preparation of (4R,5S,6S)-4-p-methoxybenzyloxy-6-methyl-5-methoxycyclohexanone

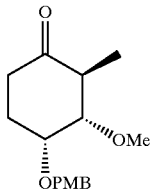

A solution of 120 mg (0.43 mmol) of (4R,5S,6S)-4-methoxybenzyloxy-6-methyl-5-methoxycyclohex-2-enone in 2 mL of methanol is stirred in the presence of 20 mg of 10% Pd/C and under a hydrogen atmosphere for 20 minutes.

The solvent is evaporated off and the residue is chromatographed on silica gel, eluent: (7/3 Cy/EtOAc).

80 mg of colourless oil are obtained. Yield=66%.

$[\alpha]_D^{20}$=−94° (CHCl$_3$, C=1.0)

$^1$H NMR (250 MHz, C$_6$D$_6$): 7.23 and 6.83 (2d, J=8.7, 4H, ArH); 4.44 (AB, 2H, OCH$_2$pC$_6$H$_4$OMe); 3.57 (ddd J=2.3, 2.3, 4.4, 1H, CHOPMB); 3.32 (s, 3H, ArOCH$_3$); 3.04 (qd, J=6.7, 11, 1H, CHCH$_3$); 2.99 3.43 (s, 3H, OCH$_3$); 2.55 (dd, J=2.4, 11, 1H, CHOCH$_3$); 2.47 (dt, J=6.2, 13.9, 13.9, 1H, CHCO); 2.07 (ddd, J=2.7, 4.8, 14, 1H, CHCO); 1.73 (dddd, J=2.8, 4.2, 6.3, 14, 1H, CHCH$_2$CO); 1.29 (d, J=6.5, 3H, CHCH$_3$); 0.94 (tdd, J=2.1, 4.9, 14, 14, 1H, CHCH$_2$CO).

$^{13}$C NMR (62.9 MHz, CDCl$_3$): 210.4, 159.2, 130.5, 129.1, 113.7, 86.2, 71.0, 69.9, 57.4, 55.2, 46.9, 35.3, 24.7, 10.5.

8. Preparation of (3R,4S,5S,6R)-methoxy-6-methoxybenzyloxy-4-methyl-1-oxaspiro[2,5]octane

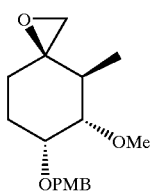

32 mg (0.82 mmol, 4.0 eq) of NaH as a 60% dispersion in oil are added at 20° C. to 1 mL of DMSO. 224 mg (1.02 mmol, 5.0 eq) of trimethylsulphoxonium iodide are added and the reaction medium is stirred for one hour at room temperature. A solution of 58 mg (0.20 mmol, 1.0 eq) of (4R,5S,6S)-4-p-methoxybenzyloxy-6-methyl-5-methoxycyclohexanone in 1 mL of DMSO is added and the reaction mixture is then stirred for 15 minutes at room temperature. The reaction is quenched by adding 2 mL of pH 7 buffer and is then extracted with ethyl acetate. The organic phases are combined, dried over sodium sulphate and then concentrated to give a colourless oil, which is chromatographed on preparative silica plates; eluent: (7/3 Cy/EtOAc).

31 mg of colourless oil are obtained. Yield=52%.

$[\alpha]_D^{20}$=−62° (CHCl$_3$, C=1.0)

$^1$H NMR (250 MHz, CDCl$_3$): 7.31 and 6.85 (2d, J=8.6, 4H, ArH); 3.90 (td, J=2.6, 2.6, 5.4, 1H, CHOPMB); 3.80 (s, 3H, ArOCH$_3$); 3.31 (s, 3H, OCH$_3$); 3.09 (dd, J=2.6, 9.2, CHOMe); 2.80 and 2.52 (2d, J=4.5, 2H, OCH$_2$epoxide); 2.32 (qd, J=6.8, 9.2, 1H, CHCH$_3$); 2.00 (m, 2H, CH$_2$—CH); 1.65 (m, 1H, CH$_2$—CH); 1.25 (m, 1H, CH$_2$—CHeqCO); 0.84 (d, J=6.9, 3H, CHCH$_3$).

$^{13}$C NMR (62.9 MHz, CDCl$_3$): 159.1, 131.0, 129.1, 113.7, 84.0, 71.5, 70.5, 59.9, 57.3, 55.2, 51.9, 35.2, 28.0, 24.9, 9.9.

9. Preparation of (3R,4S,5S,6R)-5-methoxy-4-methyl-1-oxaspiro[2,5]oct-6-yl 4-methoxycinnamate

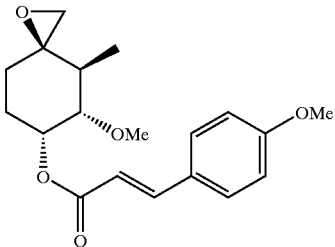

38 mg (0.169 mmol, 1.1 eq) of DDQ (2,3-dichloro-5,6-dicyano-1,4-benzoquinone) are added to a solution of 45 mg (0.154 mmol, 1.0 eq) of (3R,4S,5S,6R)-5-methoxy-6-p-methoxybenzyloxy-4-methyl-1-oxaspiro[2,5]octane in 2.5 mL of CH$_2$Cl$_2$ in the presence of 145 μL of water.

The reaction mixture is stirred for 1 hour 30 minutes. The reaction is quenched by adding 0.5 mL of saturated sodium hydrogen carbonate solution and is then extracted with ethyl acetate.

The organic phases are combined, dried over sodium sulphate and then concentrated to give a colourless oil, which is then filtered through a bed of silica gel: (eluent 1/1 Cy/EtOAc).

18 mg of colourless oil are obtained. Yield=69%.

The above oil is dissolved in 2 mL of dichloromethane and 194 mg (1.09 mmol, 10 eq) of p-methoxycinnamic acid are added, immediately followed by 133 mg (1.09 mmol, 10 eq) of DMAP (4-dimethylaminopyridine) and 224 mg (1.09 mmol, 10 eq) of DCC (dicyclohexylcarbodiimide).

The reaction mixture is stirred for 16 hours at room temperature. The solvents are evaporated off and the residue is chromatographed on a preparative silica plate: eluent (7/3 Cy/EtOAc).

30 mg of colourless oil are obtained. Yield=86%.

R$_f$=0.6 (7/3 Cy/EtOAc)

$[\alpha]_D^{20}$=−62° (CHCl$_3$, C=1.0)

$^1$H NMR (250 MHz, CDCl$_3$): 7.65 (d, J=16, 1H, COCH=CH); 7.48 and 6.90 (2d, J=8.7, 4H, ArH); 6.36 (d, J=16, 1H, COCH=CH); 5.55 (dt, J=5.1, 2.7, 2.7, 1H, CHOCO); 3.84 (s, 3H, ArOCH$_3$); 3.41 (s, 3H, OCH$_3$); 3.21 (dd, J=2.8, 9.4, CHOMe); 2.85 and 2.57 (2d, J=4.5, 2H, OCH$_2$epoxide); 2.31 (qd, J=6.8, 9.3, 1H, CHCH$_3$); 2.05–1.68 (m, 3H, CH$_2$—CHaxCO); 1.38 (m, 1H, CH$_2$—CHeqCO); 0.91 (d, J=6.5, 3H, CHCH$_3$).

$^{13}$C NMR (62.9 MHz, CDCl$_3$): 166.8, 161.3, 144.5, 129.7, 127.1, 115.7, 114.3, 82.6, 67.5, 59.5, 57.6, 55.3, 51.6, 35.7, 28.2, 25.6, 9.7.

Example 2

(3R,4S,5S,6R)-5-methoxy-4-[(E)-1,5-dimethylhexyl]-1-oxaspiro[2,5]oct-6-yl 4-methoxycinnamate 1. Preparation of (E)-3,7-dimethyloct-3-enol

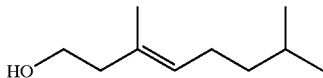

5 mL (66 mmol, 1.0 eq) of 1-butynol are added over three hours to a solution of 7.5 g (25 mmol, 0.4 eq) of zirconocene dichloride in the presence of 100 mL (200 mmol, 3.0 eq) of a 2M solution of trimethylaluminium in toluene and 150 mL of 1,2-dichloroethane, at 0° C. The reaction medium is stirred for 24 hours at room temperature, and a solution of 20 g of iodine (78 mmol, 1.2 eq) in 75 mL of THF is then added slowly, while maintaining the temperature at −30° C. The cardice bath is removed, allowing the temperature of the reaction medium to reach 0° C., and the medium is transferred using a cannula into saturated potassium carbonate solution. The reaction medium is extracted with 4×250 mL of a 2/1 cyclohexane/ether mixture. The organic phases are combined, washed with saturated sodium chloride solution and then dried over anhydrous sodium sulphate. The solvents are evaporated off and the residue is then dissolved in 100 mL of THF. 20 g (0.29 mol, 4.5 eq) of imidazole are added to the reaction medium, followed by addition of 9.0 g (60 mmol, 0.9 eq) of tert-butyldimethylsilyl chloride, the reaction medium is stirred for one hour at room temperature and the reaction is then quenched by adding 50 mL of saturated ammonium chloride solution. The reaction medium is extracted with 2×250 mL of diethyl ether and the organic phases are combined, washed with saturated sodium chloride solution and then dried over anhydrous sodium sulphate. The solvents are evaporated off and the residue is then filtered through silica gel; eluent: ether.

16.7 g (51.2 mmol) of crude vinyl iodide (intermediate A) are obtained, in the form of a slightly yellowish oil, which is used without further purification for the rest of the synthesis.

Yield=78% over two steps.

$^1$H NMR (250 MHz, CDCl$_3$): 5.92 (m, 1H, C=CH); 3.68 (t, J=6.6, 2H, TBSOCH$_2$); 2.41 (td, J=1.1, 6.6, 2H, CH$_2$CMe=C); 1.85 (s, 3H, CH$_3$); 0.89 (s, 9H, tBuSi); 0.04 (s, 6H, MeSi).

$^{13}$C NMR (62.9 MHz, CDCl$_3$): 145.0, 76.4, 61.3, 42.6, 25.9, 24.3, 18.2, −5.2.

3.96 mL (33.0 mmol, 2 eq) of isobutyl bromide in 15 mL of THF are added slowly to a suspension of 965 mg of magnesium (39.7 mmol, 2.4 eq) in 20 mL of THF, and, after the magnesium has been consumed, the suspension is heated for one hour at 70° C. and then cooled to 0° C. 35 mL (35 mmol, 2.1 eq) of a 1M solution of freshly prepared anhydrous zinc II chloride in THF are added to the above suspension, and the reaction mixture is then stirred for one hour at room temperature.

350 mg (0.34 mmol, 2 mol %) of tetrakis (triphenylphosphine)palladium are added, followed by addition of a solution of 5 g (15.3 mmol, 1 eq) of intermediate A in 25 mL of THF, at 0° C. The reaction mixture is stirred overnight at 20° C. The reaction is quenched by adding 100 mL of saturated ammonium chloride solution and then extracted with 250 mL of cyclohexane. The organic phases are combined and dried over anhydrous sodium sulphate. After evaporating off the solvents, the oil obtained is filtered through cotton wool. This oil is dissolved in 50 mL of THF, and 16 mL (16 mmol, 1.1 eq) of a 1M solution of tetrabutylammonium fluoride in THF are then added. The reaction is stirred for two hours at room temperature. The reaction is quenched by adding 100 mL of saturated ammonium chloride solution, and then extracted with 250 mL of diethyl ether. The organic phases are combined and dried over anhydrous sodium sulphate, and the residue is then filtered through silica gel: eluent (98/2→75/25 Cy/EtOAc).

1.97 g (12.6 mmol) of colourless oil are obtained. Yield=82%.

$^1$H NMR (250 MHz, CDCl$_3$): 5.22 (bt, J=7.0, 1H, C=CH); 3.63 (t, J=6.2, 2H, HOCH$_2$); 2.22 (t, J=6.2, 2H, CH$_2$CMe=C); 1.99 (dt, J=7.2, 7.9, 2H, C=CHCH$_2$); 1.61 (s, 3H, CH$_3$C=C); 1.53 (m, 1H, CHMe$_2$); 1.22 (m, 2H, C=CCH$_2$CH$_2$); 0.86 (d, J=6.6, 6H, (CH$_3$)$_2$).

$^{13}$C NMR (62.9 MHz, CDCl$_3$): 130.7, 128.2, 60.1, 42.6, 38.9, 27.6, 25.6, 22.4, 15.6.

2. 3,7-Dimethyloct-3-enoic acid

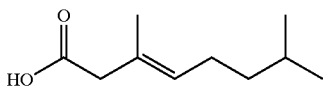

A solution of 8.84 g (88.4 mmol, 3 eq) of chromium VI oxide in 25 mL of water in the presence of 8.2 mL of 95% sulphuric acid is added to a solution of 4.6 g (29.5 mmol, 1 eq) of (E)-3,7-dimethyloct-3-enol in 250 mL of acetone, at 0° C., while maintaining the temperature at 0° C. After addition, the reaction mixture is stirred for 15 minutes at 0° C. and the reaction is then quenched by adding 250 mL of water. The reaction medium is extracted with 2×250 mL of diethyl ether. The organic phases are combined, washed with saturated sodium chloride solution and dried over anhydrous sodium sulphate, and the residue is then filtered through silica gel: eluent (95/5→75/25 Cy/EtOAc).

3.2 g (18.8 mmol) of colourless oil are obtained. Yield= 63%.

$^1$H NMR (250 MHz, CDCl$_3$): 7.5 (b, 1H, COOH); 5.30 (bt, J=6.6, 1H, C=CH); 3.01 (s, 2H, HOOCCH$_2$); 2.03 (dt, J=6.9, 8.3, 2H, C=CHCH$_2$); 1.70 (s, 3H, CH$_3$C=C); 1.55 (m, 1H, CHMe$_2$); 1.22 (m, 2H, C=CCH$_2$CH$_2$); 0.88 (d, J=6.6, 6H, (CH$_3$)$_2$).

$^{13}$C NMR (62.9 MHz, CDCl$_3$): 177.9, 130.5, 127.3, 44.7, 38.5, 27.6, 25.9, 22.5, 16.2.

3. Preparation of (4R)-4-benzyl-3-(3,7-dimethyloct-3-enoyl)oxazolidin-2-one

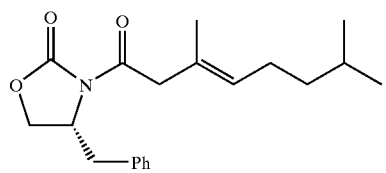

5.0 mL (40 mmol, 1.0 eq) of pivaloyl chloride are added at −78° C. to a solution of 6.95 g (40 mmol, 1.0 eq) of 3,7-dimethyloct-3-enoic acid in 90 mL of THF and 6.26 mL (44 mmol, 1.1 eq) of triethylamine. The reaction medium is stirred for 15 minutes at −78° C. and then for 15 minutes at 0° C.

26.6 mL (42 mmol, 1.05 eq) of a 1.6M solution of BuLi in hexane are added at −78° C. to a solution of 7.19 g (40 mmol, 1.0 eq) of (R)-(+)-4-benzyl-2-oxazolidinone in 80 mL of THF. The reaction medium is stirred for 15 minutes at −78° C. and this solution is then added, using a cannula, to the above solution at −78° C.

The reaction mixture is stirred for 20 minutes at −78° C., and the cardice bath is removed, allowing the temperature of the reaction medium to rise to 20° C. over one hour. The reaction is quenched by adding 50 mL of saturated ammonium chloride solution and is then extracted with dichloromethane. The organic phases are combined and dried over anhydrous sodium sulphate, and the residue is then chromatographed on silica gel; eluent: (95/5→75/25 Cy/EtOAc).

8.89 g of colourless oil are obtained. Yield=66%.

$[\alpha]_D^{20}$=−49° (CHCl$_3$, C=1.02)

$^1$H NMR (250 MHz, CDCl$_3$): 7.37–7.20 (m, 5H, ArH); 5.30 (tm, J=6.7, 1H, MeC=CH); 4.67 (dddd, J=3.0, 3.5, 7.0, 10.0, 1H, CHN); 4.18 (ABX, 2H, CH$_2$O); 3.62 (AB, 2H, COCH$_2$); 3.32 (dd, J=3.3, 13.3, 1H, CHPh); 2.75 (dd, J=9.8, 13.3, 1H, CHPh); 2.06 (bq, J=7.4, 2H, MeC=CHCH$_2$); 1.72 (s, 3H, CH$_3$C=CH); 1.55 (m, 1H, CHMe$_2$); 1.24 (m, 2H, CH$_2$CHMe$_2$); 0.88 (d, J=6.5, 6H, CH(CH$_3$)$_2$).

$^{13}$C NMR (62.9 MHz, CDCl$_3$): 171.6, 153.3, 135.3, 130.2, 129.4, 128.9, 127.6, 127.3, 66.1, 55.2, 45.4, 38.6, 37.8, 27.6, 25.9, 22.5, 16.6.

4. Preparation of (4R)-4-benzyl-3-{2(S)-2-[(1S,2R)-2-hydroxy-3-p-methoxybenzyloxybut-3-enyl]-3,7-dimethyloct-3-enoyl}oxazolidin-2-one

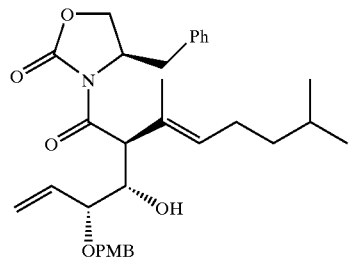

12.85 mL (20.56 mmol, 1 eq) of a 1.6M solution of butyllithium in hexane are added at 0° C. to a solution of 2.88 mL (20.56 mmol, 1 eq) of diisopropylamine in 10 mL of THF. The reaction medium is stirred for 15 minutes at 0° C. and then cooled to −78° C. A solution of 6.76 g (20.56 mmol, 1.0 eq) of (4R)-4-benzyl-3-(3,7-dimethyloct-3-enoyl)oxazolidin-2-one in 10 mL of THF is added using a cannula. After stirring for 30 minutes at −78° C., a solution of 8.28 g (22.62 mmol, 1.1 eq) of 2-(R)-4-phenylselenyl-2-p-methoxybenzyloxybutanal in 10 mL of THF is added using a cannula.

The reaction mixture is stirred for 1.5 hours at −78° C. and the reaction is then quenched by adding 10 mL of saturated ammonium chloride solution.

The flask is warmed to 20° C. and then extracted with diethyl ether. The organic phases are combined and then dried over anhydrous sodium sulphate. After evaporating off the solvents, the residue is redissolved in 150 mL of chloroform, 19.6 g (45.2 mmol, 2 eq) of tetrabutylammonium periodate are then added and the reaction mixture is stirred for two hours at 60° C.

The chloroform is evaporated off and the residue is then filtered through silica gel (4 cm) eluent: (1/1 Cy/EtOAc).

The filtrate is concentrated and then chromatographed on silica gel: eluent (9/1→8/2 Cy/EtOAc).

5.83 g of gelatinous solid are obtained. Yield=53%.

$[\alpha]_D^{20}$=−129° (CHCl$_3$, C=1.45)

$^1$H NMR (250 MHz, CDCl$_3$): 7.37–7.20 (m, 5H, ArH); 7.11 (m, 2H, ArH); 6.83 (d, J=8.6, 2H, ArH); 5.92 (ddd, J=8.0, 10.3, 17.2, 1H, CH=CH$_2$); 5.56 (tm, J=7.0, 1H, MeC=CH); 5.43 and 5.34 (2dd, J=1.8, 10.3, and J=1.8, 17.2, 2H, CH$_2$=CH); 4.77 (d, J=8.7, 1H, NCOCHC=C); 4.54 (d, J=10.8, 1H, CH$_2$pC$_6$H$_4$OMe); 4.43 (m, 1H, PhCH$_2$CHN); 4.31 (ddd, J=3.6, 6.3, 8.7, 1H, CHOH); 4.26 (d, J=10.8, 1H, CH$_2$pC$_6$H$_4$OMe); 4.01 (ABX, 2H, NCOOCH$_2$); 3.75 (m, 1H, CHOPMB); 3.69 (s, 3H, OCH$_3$); 3.08 (dd, J=3.1, 13.2, 1H, CHPh); 2.19 (d, J=3.6, 1H, OH); 2.05 (bq, J=7.3, 2H, C=CCH$_2$CH$_2$); 1.86 (dd, J=10.9, 13.2, 1H, CHPh); 1.73 (s, 3H, CH$_3$C=C); 1.50 (m, 1H, CHMe$_2$); 1.21 (m, 2H, CH$_2$CHMe$_2$); 0.85 (d, J=6.6, 6H, (CH$_3$)$_2$).

$^{13}$C NMR (62.9 MHz, CDCl$_3$): 171.8, 159.2, 152.7, 135.8, 135.7, 133.7, 130.1, 130.0, 129.4, 128.8, 127.1, 120.3, 113.7, 83.3, 72.0, 70.4, 65.6, 55.9, 55.1, 53.8, 38.4, 37.0, 27.7, 26.1, 22.5, 22.4, 14.6.

5. Preparation of 2(S)-2-[(1S,2R)-2-hydroxy-3-p-methoxybenzyloxybut-3-enyl]-3,7-dimethyloct-3-enoic acid methoxymethylamide

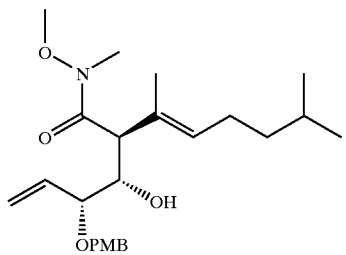

19 mL (37.9 mmol, 3.5 eq) of a 2M solution of trimethylaluminium in toluene are added at 0° C. to a suspension of 3.70 g (37.9 mmol, 3.5 eq) of N,O-dimethylhydroxylamine hydrochloride in 20 mL of THF. The reaction mixture is stirred for 30 minutes at room temperature and then cooled to 0° C. A solution of 5.79 g (10.8 mmol, 1.0 eq) of (4R)-4-benzyl-3-{2(S)-2-[(1S,2R)-2-hydroxy-3-p-methoxybenzyloxybut-3-enyl]-3,7-dimethyloct-3-enoyl}oxazolidin-2-one in 10 mL of THF is is added at 0° C. and the reaction medium is then stirred overnight at room temperature. The reaction mixture is poured into cold 25% tartaric acid solution and the resulting mixture is then extracted with 250 mL of ethyl acetate. The organic phases are combined and then dried over anhydrous sodium sulphate. After evaporating off the solvents, the residue is chromatographed on silica gel: eluent (85/15→8/2 Cy/EtOAc).

3.41 g of colourless oil are obtained. Yield=75%.

$[\alpha]_D^{20}$=−125° (CHCl$_3$, C=0.975)

$^1$H NMR (250 MHz, CDCl$_3$): 7.25 & 6.87 (2d, J=8.6, 4H, ArH); 5.89 (ddd, J=8.1, 10.3, 17.2, 1H, CH=CH$_2$); 5.39 (dd, J=2.0, 10.3, 1H, CH$_2$=CH); 5.36 (m, 1H, MeC=CH); 5.30 (dd, J=2.0, 17.2, 1H, CH$_2$=CH); 4.52 and 4.26 (2d, J=11.0, 2H, CH$_2$pC$_6$H$_4$OMe); 4.18 (dt, J=2.1, 6.2, 6.2, 1H, CHOH); 3.80 (s, 3H, ArOCH$_3$); 3.79 (m, 1H, CHOPMB); 3.70 (m, 1H, NCOCHC=C); 3.61 (s, 3H, NOCH$_3$); 3.31 (bs, 1H, OH); 3.12 (s, 3H, NCH$_3$); 2.06 (bq, J=7.1, 2H, C=CHCH$_2$); 1.73 (s, 3H, CH$_3$C=C); 1.54 (m, 1H, CHMe$_2$); 1.22 (m, 2H, CH$_2$CHMe$_2$); 0.87 (d, J=6.6, 6H, (CH$_3$)$_2$).

$^{13}$C NMR (62.9 MHz, CDCl$_3$): 159.0, 135.5, 131.8, 130.5, 129.6, 129.3, 119.7, 113.7, 81.2, 72.9, 69.7, 61.0, 55.2, 51.3, 38.6, 32.0, 27.7, 26.0, 22.5, 22.4, 15.2.

6. Preparation of 2(S)-2-[(1S,2R)-2-methoxy-3-p-methoxybenzyloxybut-3-enyl]-3,7-dimethyloct-3-enoic acid methoxymethylamide

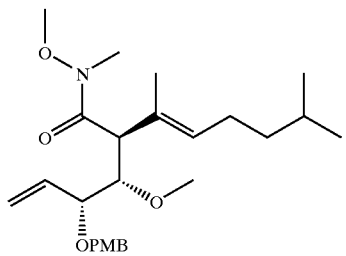

8 mL of methyl iodide are added to a suspension of 8 g of silver oxide (35 mmol, 5 eq) and 2 g of 4 Å molecular sieves in 10 mL of diethyl ether, in the presence of 2.96 g (7.0 mmol, 1.0 eq) of 2(S)-2-[(1S,2R)-2-hydroxy-3-p-methoxybenzyloxybut-3-enyl]-3,7-dimethyloct-3-enoic acid methoxymethylamide. The suspension is stirred for eight hours at 45° C. The reaction mixture is filtered through Celite and the solvents are then evaporated off. The residual oil is chromatographed on silica gel; eluent: (9/1 Cy/EtOAc).

2.8 g of colourless oil are obtained. Yield=93%

$[\alpha]_D^{20}$=−121° (CHCl$_3$, C=1.0)

$^1$H NMR (250 MHz, CDCl$_3$): 7.26 & 6.85 (2d, J=8.6, 4H, ArH); 5.92 (ddd, J=8.1, 10.3, 17.3, 1H, CH=CH$_2$); 5.36 (bt, J=7.1, 1H, MeC=CH); 5.31 (dd, J=2.1, 10.3, 1H, CH$_2$=CH); 5.20 (dd, J=2.0, 17.3, 1H, CH$_2$=CH); 4.51 and 4.34 (2d, J=11.4, 2H, CH$_2$pC$_6$H$_4$OMe); 3.98 (dd, J=3, 9.9, 1H, CHOMe); 3.80 (m, 1H, CHOPMB); 3.79 (s, 3H, ArOCH$_3$); 3.58 (s, 3H, NOCH$_3$); 3.49 (m, 1H, NCOCHC=C); 3.46 (s, 3H, OCH$_3$); 3.07 (s, 3H, NCH$_3$); 2.00 (bq, J=7.4, 2H, C=CHCH$_2$); 1.72 (s, 3H, CH$_3$C=C); 1.53 (m, 1H, CHMe$_2$); 1.23 (m, 2H, CH$_2$CHMe$_2$); 0.86 (d, J=6.6, 6H, (CH$_3$)$_2$).

$^{13}$C NMR (62.9 MHz, CDCl$_3$): 158.8, 135.4, 130.9, 130.7, 129.9, 129.0, 119.2, 113.5, 82.9, 82.8, 69.9, 61.0, 60.9, 55.2, 52.0, 38.5, 32.3, 27.6, 25.9, 22.5, 22.5, 15.3.

7. Preparation of (4S,5E)-4-[(1S,2R)-2-methoxy-3-p-methoxybenzyloxybut-3-enyl]-5,9-dimethyldeca-1,5-dien-3-one

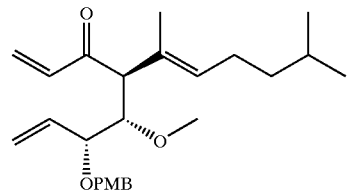

10 mL (10 mmol, 5.0 eq) of a 1M solution of vinylmagnesium bromide in THF are added at 0° C. to a solution of 877 mg (2.02 mmol, 1.0 eq) of 2(S)-2-[(1S,2R)-2-methoxy-3-p-methoxybenzyloxybut-3-enyl]-3,7-dimethyloct-3-enoic acid methoxymethylamide in 5 mL of THF. After stirring the reaction mixture for 12 hours at 20° C., it is transferred using a cannula into a round-bottomed flask containing 5 mL of an NH$_4$Cl/THF mixture (2/1) at 0° C. 15 mL of saturated sodium chloride solution are added to the reaction mixture and the resulting mixture is then extracted with diethyl ether. The organic phases are combined and then dried over anhydrous sodium sulphate. After evaporating off the solvents, the residue is chromatographed on silica gel; eluent: (95/5 Cy/EtOAc).

689 mg of colourless oil are obtained. Yield=85%.

$[\alpha]_D^{20}$=−293° (CHCl$_3$, C=1.07)

$^1$H NMR (250 MHz, CDCl$_3$): 7.24 & 6.86 (2d, J=8.6, 4H, ArH); 6.35 (dd, J=10.1, 17.4, 1H, CH$_2$=CHCO); 6.18 (dd, J=1.8, 17.4, 1H, CH$_2$=CHCO); 5.88 (ddd, J=8.2, 10.3, 17.3, 1H, CH$_2$=CHCHOPMB); 5.64 (dd, J=1.8, 10.1, 1H, CH$_2$=CHCO); 5.36 (tm, J=7.0, 1H, MeC=CH); 5.31 (dm, J=10.3, 1H, CH$_2$=CH); 5.15 (dm, J=17.4, 1H, CH=CH); 4.49 and 4.28 (2d, J=11.4, 2H, CH$_2$pC$_6$H$_4$OMe); 4.01 (dd, J=3.8, 9.1, 1H, CHOMe); 3.80 (s, 3H, ArOCH$_3$); 3.70 (dd, J=3.8, 9.1, 1H, CHOPMB); 3.47 (s, 3H, OCH$_3$); 3.46 (d, J=9.1, 1H, COCHC=C); 2.03 (bq, J=7.6, 2H, C=CHCH$_2$); 1.60 (s, 3H, CH$_3$C=C); 1.51 (m, 1H, CHMe$_2$); 1.21 (m, 2H, CH$_2$CHMe$_2$); 0.86 (2d, J=6.6, 6H, (CH$_3$)$_2$).

$^{13}$C NMR (62.9 MHz, CDCl$_3$): 198.0, 158.9, 135.5, 135.5, 132.7, 130.7, 129.3, 129.1, 127.8, 119.5, 113.6, 82.5, 81.4, 69.9, 61.4, 60.7, 55.2, 38.4, 27.6, 26.2, 22.5, 22.5, 14.4.

8. Preparation of (4R,5S,6S)-5-methoxy-4-p-methoxybenzyloxy-6-(1,5-dimethylhex-1-enyl)cyclohex-2-enone

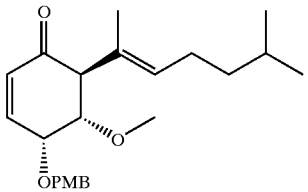

11.5 μL (0.039 mmol, 0.25 eq) of Ti(OiPr)$_4$ are added to a solution of 63 mg (0.157 mmol, 1.0 eq) of (4S,5E)-4-[(1S,2R)-2-methoxy-3-p-methoxybenzyloxybut-3-enyl]-5,9-dimethyldeca-1,5-dienone in 3 mL of dichloromethane. The reaction mixture is heated for 30 minutes at 40° C., and 26 mg (0.30 mmol, 0.2 eq) of Grubbs complex 1 are then added to the solution. The reaction mixture is heated for 16 hours at 60° C. The reaction is quenched by adding 5 mL of pH 7 buffer and the reaction mixture is extracted with diethyl ether. The residue is chromatographed on silica gel: eluent (8/2 Cy/EtOAc) to give 28 mg of (4R,5S,6S)-5-methoxy-4-p-methoxybenzyloxy-6-(1,5-dimethylhex-1-enyl)cyclohex-2-enone. Yield=48%.

$R_f$=0.42 (8/2 Cy/EtOAc)

$[\alpha]_D^{20}$=−86° (CHCl$_3$, C=1.8)

$^1$H NMR (250 MHz, CDCl$_3$): 7.30 & 6.89 (2d, J=8.7, 4H, ArH); 6.78 (ddd, J=1.0, 3.7, 10.1, 1H, CH=CHCHOPMB); 6.06 (dd, J=1.5, 10.1, 1H, CH=CHCHOPMB); 5.13 (tm, J=7.0, 1H, MeC=CH); 4.65 (AB, 2H, OCH$_2$pC$_6$H$_4$OMe); 4.31 (dt, J=1.5, 3.4, 3.4, 1H, CHOPMB); 3.81 (s, 3H, ArOCH$_3$); 3.75 (ddd, J=1.1, 3.2, 6.8, 1H, CHOMe); 3.42 (d, J=6.8, 1H, COCHC=C); 3.41 (s, 3H, OCH$_3$); 2.00 (bq, J=7.2, 2H, C=CHCH$_2$); 1.58 (s, 3H, CH$_3$C=C); 1.50 (m, 1H, CHMe$_2$); 1.19 (m, 2H, CH$_2$CHMe$_2$); 0.86 (d, J=6.6, 6H, (CH$_3$)$_2$).

$^{13}$C NMR (62.9 MHz, CDCl$_3$): 199.0, 159.4, 145.5, 130.8, 130.2, 129.9, 129.6, 128.9, 113.9, 80.0, 71.6, 70.6, 58.6, 57.7, 55.3, 38.4, 27.6, 25.9, 22.5, 22.5, 15.3.

9. Preparation of (2S,3S,4R)-3-methoxy-4-p-methoxybenzyloxy-2-(1,5-dimethylhex-1-enyl)cyclohexanone

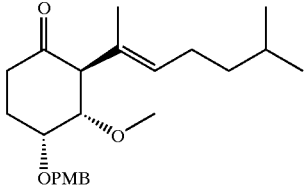

15 drops of a suspension of Raney nickel are added to a solution of 45 mg (0.121 mmol) of (4R,5S,6S)-5-methoxy-4-p-methoxybenzyloxy-6-(1,5-dimethylhex-1-enyl)cyclohex-2-enone in 1.5 mL of THF at 0° C. The medium is stirred vigorously for 20 minutes at 0° C. The reaction is quenched by adding 2 mL of diethyl ether and is then extracted with ethyl acetate. The organic solvents are filtered through a patch of silica (1 cm). The solvents are evaporated off and the residue is then chromatographed on silica gel: eluent (8/2 Cy/EtOAc).

37 mg of colourless oil are obtained. Yield=82%.

$[\alpha]_D^{20}$=−10° (CHCl$_3$, C=1.0)

$^1$H NMR (250 MHz, CDCl$_3$): 7.33 & 6.88 (2d, J=8.6, 4H, ArH); 5.16 (tm, J=7.0, 1H, MeC=CH); 4.67 (AB, 2H, OCH$_2$pC$_6$H$_4$OMe); 4.11 (dt, J=2.2, 2.2, 4.6, 1H, CHOPMB); 3.80 (s, 3H, ArOCH$_3$); 3.49 (d, J=10.7, 1H, COCHC=C); 3.43 (dd, J=2.2, 10.7, 1H, CHOMe); 3.33 (s, 3H, OCH$_3$); 2.60 (m, 1H, CH$_{ax}$CO); 2.26–2.14 (m, 2H, CH$_{eq}$CO & CH$_{eq}$CHOPMB); 2.06 (m, 2H, C=CHCH$_2$); 1.65–1.46 (m, 2H, CH$_{ax}$CHOPMB & CHMe$_2$); 1.57 (s, 3H, CH$_3$C=C); 1.19 (m, 2H, CH$_2$CHMe$_2$); 0.87 (d, J=6.6, 6H, (CH$_3$)$_2$).

$^{13}$C NMR (62.9 MHz, CDCl$_3$): 209.1, 159.2, 130.8, 130.5, 129.2, 129.0, 113.7, 81.9, 71.1, 70.3, 61.9, 57.4, 55.3, 38.6, 35.8, 27.6, 25.9, 24.5, 22.5, 22.5, 14.1.

10. Preparation of (3R,4S,5S,6R)-4-(1,5-dimethylhex-1-enyl)-5-methoxy-6-p-methoxybenzyloxy-1-oxaspiro[2,5]octane

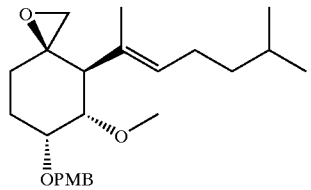

1 mL of DMSO is added to 40 mg (1.01 mmol, 10 eq) of sodium hydride at 60% in grease, degreased beforehand in pentane. The reaction medium is stirred for five minutes at room temperature and 334 mg (1.52 mmol, 15 eq) of trimethylsulphoxonium iodide are then added to the above solution. The reaction mixture is stirred for one hour at room temperature, followed by addition of 1 mL of THF and 163 mg (1.21 mmol, 12 eq) of lithium iodide. The suspension is stirred for 40 minutes at room temperature. A solution of 38 mg (0.101 mmol, 1.0 eq) of (2S,3S,4R)-3-methoxy-4-p-methoxybenzyloxy-2-(1,5-dimethylhex-1-enyl)cyclohexanone in 1 mL of 1/1 DMSO/THF is added at 0° C. The reaction mixture is stirred for 30 minutes at room temperature. The reaction is quenched by adding 5 mL of diethyl ether and 5 mL of pH 7 buffer solution. The medium is extracted with diethyl ether. The organic phases are combined and then dried over anhydrous sodium sulphate. After evaporating off the solvents, the residue is chromatographed on silica gel: eluent (9/1 Cy/EtOAc).

30 mg of colourless oil are obtained. Yield=77%.

$[\alpha]_D^{20}$=−68° (CHCl$_3$, C=0.85)

$^1$H NMR (250 MHz, CDCl$_3$): 7.32 & 6.87 (2d, J=8.6, 4H, ArH); 5.21 (tm, J=7.4, 1H, MeC=CH); 4.62 (s, 2H, OCH$_2$pC$_6$H$_4$OMe); 4.07 (dt, J=2.3, 2.3, 4.5, 1H, CHOPMB); 3.80 (s, 3H, ArOCH$_3$); 3.49 (dd, J=2.6, 11.2, 1H, CHOMe); 3.30 (s, 3H, OCH$_3$); 2.99 (d, J=11.2, 1H, CHC=C); 2.65 & 2.42 (2d, J=5.0, 2H, OCH$_2$ epoxide); 2.23 (dt, J=4.3, 13.5, 13.5, 1H, CHaxCO); 2.11–1.94 (m, 3H, CH$_{eq}$CHOPMB & C=CHCH$_2$); 1.69–1.47 (m, 2H, CH$_{ax}$-CHOPMB & CHMe$_2$); 1.54 (s, 3H, CH$_3$C=C); 1.29–1.15 (m, 2H, CH$_2$CHMe$_2$); 1.06 (ddd, J=2.8, 4.0, 13.5, 1H, CHeqCO); 0.87 & 0.86 (2d, J=6.6, 6H, (CH$_3$)$_2$).

$^{13}$C NMR (62.9 MHz, CDCl$_3$): 159.0, 131.7, 131.0, 130.7, 129.2, 113.6, 81.0, 70.7, 70.4, 60.9, 56.6, 55.2, 51.4, 48.6, 38.8, 28.5, 27.7, 25.7, 25.0, 22.6, 22.5, 14.1.

11. Preparation of (3R,4S,5S,6R)-5-methoxy-4-[(E)-1,5-dimethylhexyl]-1-oxaspiro[2,5]oct-6-yl 4-methoxycinnamate

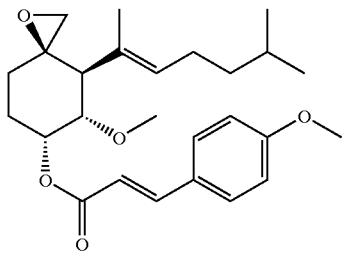

11 mg (48 μmol, 1.1 eq) of DDQ (2,3-dichloro-5,6-dicyano-1,4-benzoquinone) are added to a solution of 17 mg (43.8 μmol, 1 eq) of (3R,4S,5S,6R)-4-(1,5-dimethylhex-1-enyl)-5-methoxy-6-p-methoxybenzyloxy-1-oxaspiro[2,5] octane in 2 mL of $CH_2Cl_2$ in the presence of 65 μL of water.

The reaction mixture is stirred for 1 hour 30 minutes. The reaction is quenched by adding 0.5 mL of saturated sodium hydrogen carbonate solution and then extracted with ethyl acetate.

The organic phases are combined, dried over sodium sulphate and then concentrated to give a colourless oil, which is then filtered through a bed of silica gel; eluent: (6/4 Cy/EtOAc).

10.5 mg of colourless oil are obtained Yield=90%.

The above oil is dissolved in 2 mL of dichloromethane and 77 mg (0.42 mmol, 10 eq) of p-methoxycinnamic acid are added, immediately followed by addition of 53 mg (0.42 mmol, 10 eq) of DMAP (4-dimethylaminopyridine) and 86 mg (0.42 mmol, 10 eq) of DCC (dicyclohexylcarbodiimide). The reaction mixture is stirred for 48 hours at room temperature.

The solvents are evaporated off and the residue is chromatographed on a preparative silica plate; eluent: (8/2 n-hex/EtOAc).

13.5 mg of colourless oil are obtained. Yield=72% over the two steps.

$[\alpha]_D^{20}$=−118° (CHCl$_3$, C=0.67)

$^1$H NMR (250 MHz, CDCl$_3$): 7.66 (d, J=16, 1H, COCH=CH); 7.48 and 6.90 (2d, J=8.8, 4H, ArH); 6.38 (d, J=16, 1H, COCH=CH); 5.72 (dt, J=2.6, 2.6, 3.9, 1H, CHOCO); 5.26 (tm, J=7.2, 1H, MeC=CH); 3.84 (s, 3H, ArOCH$_3$); 3.63 (dd, J=2.8, 11.2, 1H, CHOMe); 3.37 (s, 3H, OCH$_3$); 2.93 (d, J=11.2, 1H, CHC=C); 2.70 and 2.49 (2d, J=5, 2H, OCH$_2$epoxide); 2.22 (dt, J=4.5, 13.6, 13.6, 1H, CH$_2$axCO); 2.12–1.99 (m, 3H, C=CHCH$_2$, CH$_2$eqCHOCO); 1.89 (tdd, J=2.4, 4.2, 13.6, 13.6, 1H, CH$_2$axCHOCO); 1.58 (s, 3H, CH$_3$C=C); 1.54 (m, 1H, CHMe$_2$); 1.26–1.17 (m, 2H, CH$_2$CHMe$_2$); 1.18 (ddd, J=2.5, 4.1, 13.8, 1H, CH$_2$eqCO); 0.87 & 0.86 (2d, J=6.6, 6H, (CH$_3$)$_2$).

$^{13}$C NMR (62.9 MHz, CDCl$_3$): 166.9, 161.3, 144.5, 131.0, 130.8, 129.7, 127.2, 115.9, 114.3, 79.2, 66.7, 60.6, 57.0, 55.3, 51.4, 49.4, 38.8, 28.8, 27.7, 25.8, 25.7, 22.6, 22.4, 14.1.

Example 3

(3R,4S,5S,6R,7R)-6-hydroxy-5-methoxy-7-methyl-4-[(E)-1,5-dimethylhexyl]-1-oxaspiro[2,5]octane

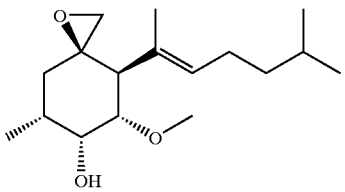

1. Preparation of (4R,5S,6S)-4-hydroxy-5-methoxy-6-(1,5-dimethylhex-1-enyl)cyclohex-2-enone

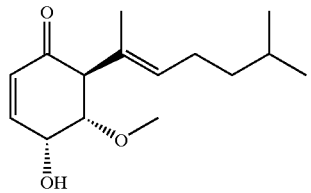

13 mg (59 μmol, 1.1 eq) of DDQ (2,3-dichloro-5,6-dicyano-1,4-benzoquinone) are added to a solution of 20 mg (53 μmol, 1.0 eq) of (4R,5S,6S)-5-methoxy-4-p-methoxybenzyloxy-6-(1,5-dimethylhex-1-enyl)cyclohex-2-enone in 2 mL of $CH_2Cl_2$ in the presence of 65 μL of water. The reaction mixture is stirred for seven hours at room temperature. The reaction is quenched by adding 0.5 mL of saturated sodium hydrogen carbonate solution and then extracted with ethyl acetate. The organic phases are combined, dried over sodium sulphate and then concentrated to give a colourless oil, which is then filtered through a bed of silica gel: eluent (6/4 Cy/EtOAc).

10.5 mg of white solid are obtained. Yield=78%.
m.p.=46–47° C.
$[\alpha]_D^{20}$=−43° (CHCl$_3$, C=1.02)
$^1$H NMR (250 MHz, CDCl$_3$): 6.78 (ddd, J=1.3, 3.1, 10.1, 1H, CH=CHCHOH); 6.07 (dd, J=1.7, 10.1, 1H, CH=CHCHOH); 5.15 (tm, J=7.0, 1H, MeC=CH); 4.51 (m, 1H, CHOH); 3.77 (ddd, J=1.3, 3.7, 5.1, 1H, CHOMe); 3.44 (s, 3H, OCH$_3$); 3.39 (d, J=5.2, 1H, COCHC=C); 3.84 (s, 1H, OH); 2.02 (bq, J=7.1, 2H, C=CHCH$_2$); 1.68 (s, 3H, CH$_3$C=C); 1.52 (m, 1H, CHMe$_2$); 1.19 (m, 2H, CH$_2$CHMe$_2$); 0.86 (2d, J=6.6, 6H, (CH$_3$)$_2$).

$^{13}$C NMR (62.9 MHz, CDCl$_3$): 198.4, 147.3, 130.4, 130.0, 128.7, 81.2, 64.8, 57.4, 57.3, 38.5, 27.6, 26.0, 22.5, 22.4, 15.8.

2. Preparation of (2S,3S,4R,5R)-4-hydroxy-3-methoxy-5-methyl-2-(1,5-dimethylhex-1-enyl)cyclohexanone

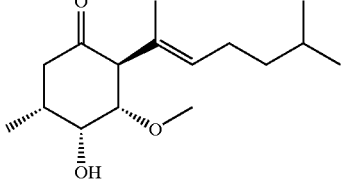

0.8 mL (1.6 mmol, 10 eq) of a 2 M solution of Me$_3$Al in toluene are added at 0° C. to a solution of 42 mg (0.166 mmol, 1.0 eq) of (4R,5S,6S)-4-hydroxy-5-methoxy-6-(1,5-dimethylhex-1-enyl)cyclohex-2-enone. The reaction medium is stirred for four hours at room temperature and then poured into 20% tartaric acid solution. The reaction mixture is extracted with ethyl acetate. The organic phases are combined, dried over sodium sulphate and then concentrated to give a colourless oil, which is then chromatographed on preparative silica plates: eluent (7/3 Cy/EtOAc).

26.5 mg of colourless oil are obtained. Yield=58%.

$[\alpha]_D^{20}$=+22° (CHCl$_3$, C=0.95)

m.p.=33–34° C.

$^1$H NMR (250 MHz, CDCl$_3$): 5.18 (tm, J=6.9, 1H, MeC=CH); 4.14 (bs, 1H, CHOH); 3.41 (s, 3H, OCH$_3$); 3.39 (dd, J=2.6, 11.2, 1H, CHOMe); 3.26 (d, J=11.2, 1H, COCHC=C); 2.55 (t, J=13.9, 1H, CHaxCO); 2.37 (s, 1H, OH); 2.15–2.04 (m, 3H, C=CHCH$_2$ & CHeqCO); 1.83 (m, 1H, MeCHCHOH); 1.61 (s, 3H, CH$_3$C=C); 1.57 (m, 1H, CHMe$_2$); 1.26 (m, 2H, CH$_2$CHMe$_2$); 1.17 (d, J=6.7, 3H, MeCHCHOH); 0.86 (2d, J=6.6, 6H, (CH$_3$)$_2$).

$^{13}$C NMR (62.9 MHz, CDCl$_3$): 208.3, 131.4, 128.7, 82.2, 68.4, 60.5, 57.6, 42.8, 38.6, 32.0, 27.6, 25.9, 22.6, 22.5, 17.7, 14.2.

3. Preparation of (2S,3S,4R,5R)-3-methoxy-5-methyl-4-trimethylsilyloxy-2-(1,5-dimethylhex-1-enyl)cyclohexanone

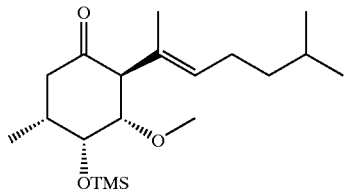

29 μL (0.233 mmol, 2.5 eq) of TMSCl (trimethylsilyl chloride) are added at room temperature to a solution of 25 mg (93 μmol, 1.0 eq) of (2S,3S,4R,5R)-4-hydroxy-3-methoxy-5-methyl-2-(1,5-dimethylhex-1-enyl)cyclohexanone in 2 mL of CH$_2$Cl$_2$ in the presence of 130 μL (0.93 mmol, 10.0 eq) of triethylamine and 34 mg (0.279 mmol, 3.0 eq) of DMAP (4-dimethylaminopyridine). The reaction mixture is stirred for one hour at room temperature. The reaction is quenched by adding 10 mL of saturated ammonium chloride solution and is then extracted with diethyl ether. The organic phases are combined and dried over anhydrous sodium sulphate, and the residue is then chromatographed on preparative silica plates: eluent (9/1 Cy/EtOAc).

29.8 mg of colourless oil are obtained. Yield=94%.

$[\alpha]_D^{20}$=−4.3° (CHCl$_3$, C=1.40)

$^1$H NMR (250 MHz, CDCl$_3$): 5.12 (tm, J=6.9, 1H, MeC=CH); 4.10 (bs, 1H, CHOTMS); 3.33 (s, 3H, OCH$_3$); 3.32 (d, J=11.4, 1H, COCHC=C); 3.22 (dd, J=1.9, 11.4, 1H, CHOMe); 2.44 (t, J=13.9, 1H, CHaxCO); 2.13–2.02 (m, 3H, C=CHCH$_2$ & CHeqCO); 1.76 (m, 1H, MeCHCHOTMS); 1.58 (s, 3H, CH$_3$C=C); 1.57 (m, 1H, CHMe$_2$); 1.25 (m, 2H, CH$_2$CHMe$_2$); 1.01 (d, J=6.6, 3H, MeCHCHOTMS); 0.87 (2d, J=6.9, 6H, (CH$_3$)$_2$); 0.16 (s, 9H, SiMe$_3$).

$^{13}$C NMR (62.9 MHz, CDCl$_3$): 209.3, 131.0, 129.0, 82.8, 70.5, 60.6, 57.7, 43.4, 38.7, 32.6, 27.7, 25.9, 22.6, 22.6. 18.1, 14.3, 0.6.

4. Preparation of (3R,4S,5S,6R,7R)-5-methoxy-7-methyl-6-trimethylsilyloxy-4-[(E)-1,5-dimethylhexyl]-1-oxaspiro[2,5]octane

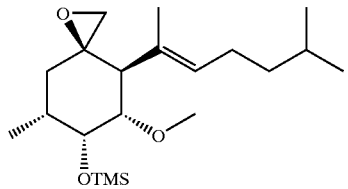

1 mL of DMSO is added to 31 mg (0.79 mmol, 10 eq) of sodium hydride at 60% in grease, degreased beforehand in pentane. The reaction medium is stirred for five minutes at room temperature, and 261 mg (1.19 mmol, 15 eq) of trimethylsulphoxonium iodide are then added to the above suspension. The reaction mixture is stirred for one hour at room temperature, 1 mL of THF and 127 mg (0.95 mmol, 12 eq) of lithium iodide are added, and the suspension is stirred for 40 minutes at room temperature. A solution of 25 mg (0.073 mmol, 1.0 eq) of (2S,3S,4R,5R)-3-methoxy-5-methyl-4-trimethylsilyloxy-2-(1,5-dimethylhex-1-enyl)cyclohexanone in 1 mL of 1/1 DMSO/THF is added at 0° C. The reaction mixture is stirred for two hours at room temperature. The reaction is quenched by adding 5 mL of diethyl ether and 5 mL of a pH 7 buffer solution. The medium is extracted with diethyl ether. The organic phases are combined and then dried over anhydrous sodium sulphate. After evaporating off the solvents, the residue is chromatographed on silica gel: eluent (9/1 Cy/EtOAc).

21.6 mg of colourless oil are obtained. Yield=83%.

$[\alpha]_D^{20}$=−55° (CHCl$_3$, C=1.52)

$^1$H NMR (250 MHz, CDCl$_3$): 5.16 (tm, J=6.7, 1H, MeC=CH); 4.07 (bs, 1H, CHOTMS); 3.34 (dd, J=2.1, 11.6, 1H, CHOMe); 3.33 (s, 3H, OCH$_3$); 2.85 (d, J=11.5, 1H, CHCMe=C); 2.62 & 2.38 (2d, J=5.1, 2H, OCH$_2$ epoxide); 2.11–1.79 (m, 3H, C=CHCH$_2$ & MeCHCHOTMS); 2.05 (t, J=12.9, 1H, CHaxCHMe); 1.54 (s, 3H, CH$_3$C=C); 1.53 (m, 1H, CHMe$_2$); 1.20 (m, 2H, CH$_2$CHMe$_2$); 0.92 (d, J=6.6, 3H, MeCHCHOTMS); 0.87 & 0.86 (2d, J=6.6, 6H, (CH$_3$)$_2$); 0.85 (m, 1H, CHeqCHMe); 0.16 (s, 9H, SiMe$_3$).

$^{13}$C NMR (62.9 MHz, CDCl$_3$): 131.2, 130.6, 82.4, 70.6, 60.6, 57.1, 51.0, 47.1, 38.9, 36.1, 32.8, 27.7, 25.8, 22.6, 22.5, 18.2, 14.6. 0.6.

5. Preparation of (3R,4S,5S,6R,7R)-6-hydroxy-5-methoxy-7-methyl-4-[(E)-1,5-dimethylhexyl]-1-oxaspiro[2,5]octane

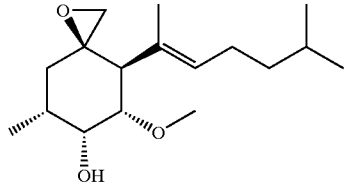

2 mg (7.9 μmol, 10 mol %) of PPTS (pyridinium p-toluenesulphonate) are added to a solution of 28 mg (79 μmol, 1.0 eq) of (3R,4S,5S,6R,7R)-5-methoxy-7-methyl-6-trimethylsilyloxy-4-[(E)-1,5-dimethylhexyl]-1-oxaspiro[2,5]octane in 2 mL of THF in the presence of 0.1 mL of water. The reaction medium is stirred for 24 hours at room temperature. The reaction is quenched by adding 2 mL of saturated sodium hydrogen carbonate solution. The reaction medium is extracted with diethyl ether. The organic phases are combined and then dried over anhydrous sodium sulphate. After evaporating off the solvents, the residue is chromatographed on silica gel: eluent (7/3 Cy/EtOAc).

6.6 mg of colourless oil are obtained. Yield=30%.

$^1$H NMR (250 MHz, CDCl$_3$): 5.21 (tm, J=7.6, 1H, MeC=CH); 4.13 (bs, 1H, CHOH); 3.50 (dd, J=2.7, 11.4, 1H, CHOMe); 3.39 (s, 3H, OCH$_3$); 2.77 (d, J=11.4, 1H, CHCMe=C); 2.62 & 2.43 (2d, J=5.0, 2H, OCH$_2$ epoxide); 2.16 (bs, 1H, OH); 2.09 (t, J=13.0, 1H, CHaxCHMe); 2.08–1.93 (m, 3H, MeCH & C=CHCH$_2$); 1.56 (s, 3H, CH$_3$C=C); 1.53 (m, 1H, CHMe$_2$); 1.19 (m, 2H, CH$_2$CHMe$_2$); 1.08 (d, J=6.6, 3H, MeCHCHOH); 0.94 (dd, J=3.6, 13.1, 1H, CHeqCHMe); 0.88 & 0.87 (2d, J=6.6, 6H, (CH$_3$)$_2$).

$^{13}$C NMR (62.9 MHz, CDCl$_3$): 130.9, 81.4, 68.5, 60.4, 56.8, 50.9, 47.3, 38.8, 35.6, 31.7, 27.7, 25.7, 22.6, 22.5, 17.7, 14.5.

Example 4

Preparation of (3R,4S,5S,6R,7R)-6-hydroxy-5-methoxy-7-methyl-4-[(1R,2R)-1,2-epoxy-1,5-dimethylhexyl]-1-oxaspiro[2,5]octane

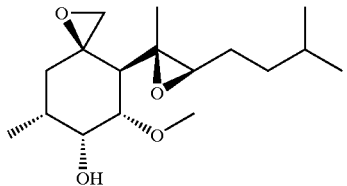

8 mg (31 μmol, 1.5 eq) of 70% meta-chloroperbenzoic acid are added at 0° C. to a solution of 6.6 mg (21 μmol, 1.0 eq) of (3R,4S,5S,6R,7R)-hydroxy-5-methoxy-7-methyl-4-[(E)-1,5-dimethylhexyl]-1-oxaspiro[2,5]octane in 2 mL of dichloromethane in the presence of 10 mg (0.126 mmol, 6.0 eq) of sodium hydrogen carbonate. The reaction mixture is stirred for one hour at 0° C. and then for one hour at room temperature. The reaction is quenched by adding 5 mL of saturated sodium hydrogen carbonate solution and is then extracted with ethyl acetate. The organic phases are combined and then dried over anhydrous sodium sulphate. After evaporating off the solvents, the residue is chromatographed on preparative silica plates: eluent (7/3 Cy/EtOAc).

6.0 mg of colourless oil are obtained. Yield=94%.

$^1$H NMR (250 MHz, CDCl$_3$): 4.16 (bs, 1H, CHOH); 3.62 (dd, J=2.5, 11.3, 1H, CHOMe); 3.50 (s, 3H, OCH$_3$); 2.85 & 2.57 (2d, J=4.9, 2H, OCH$_2$ epoxide); 2.54 (dd, J=4.5, 7.4, 1H, OCH epoxide); 2.04 (t, J=13.5, 1H, CHaxCHMeCHOH); 1.92 (m, 1H, MeCHCHOH); 1.90 (d, J=11.4, 1H, CHCHOMe); 1.66–1.20 (m, 6H, CH$_2$CH$_2$CHMe$_2$, CHOH); 1.18 (s, 3H, CH$_3$); 1.08 (d, J=6.6, 3H, MeCHCHOH); 0.90 (2d, J=6.6, 6H, Me$_2$CH); 0.89 (m, 1H, CHeqCHMeCHOH).

$^{13}$C NMR (62.9 MHz, CDCl$_3$): 81.5, 68.1, 62.0, 59.5, 58.4, 56.4, 50.6, 46.5, 36.1, 35.6, 31.7, 27.9, 26.0, 22.6, 22.3, 17.5, 13.9.

Example 5

(3R,4S,5S,6R,7R)-5-methoxy-7-methyl-4-[(1R,2R)-1,2-epoxy-1,5-dimethylhexyl]-1-oxaspiro[2,5]oct-6-yl 4-methoxycinnamate

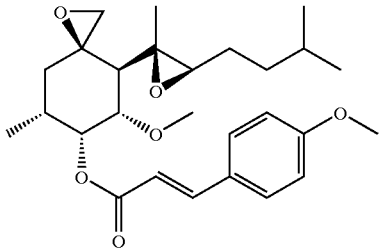

35 mg (0.20 mmol, 10 eq) of p-methoxycinnamic acid, followed immediately by 25 mg (0.20 mmol, 10 eq) of DMAP (4-dimethylaminopyridine) and 41 mg (0.20 mmol, 10 eq) of DCC (dicyclohexylcarbodiimide), are added to a solution of 6 mg (20 μmol, 1.0 eq) of (3R,4S,5S,6R,7R)-6-hydroxy-5-methoxy-7-methyl-4-[(1R,2R)-1,2-epoxy-1,5-dimethylhexyl]-1-oxaspiro[2,5]octane in 2 mL of dichloromethane. The reaction mixture is stirred overnight at room temperature. The solvents are evaporated off and the residue is filtered through a patch of silica (1 cm): eluent (1/1 Cy/EtOAc). The residue is then chromatographed on preparative silica plates: eluent (8/2 n-hex/EtOAc).

7.9 mg of colourless oil are obtained. Yield=95%.

$[\alpha]_D^{20}$=–43° (CHCl$_3$, C=0.39) (contains 15% of cis isomer).

$^1$H NMR (250 MHz, CDCl$_3$): 7.62 (d, J=15.9, 1H, COCH=CH); 7.47 & 6.90 (2d, J=8.7, 4H, ArH); 6.36 (d, J=15.9, 1H, COCH=CH); 5.90 (bs, 1H, CHOCO); 3.83 (s, 3H, ArOCH$_3$); 3.70 (dd, J=2.7, 11.5, 1H, CHOMe); 3.48 (s, 3H, OCH$_3$); 2.92 & 2.60 (2d, J=4.4, 2H, OCH$_2$epoxide); 2.57 (m, 1H, OCHepoxide); 2.10 (m, 1H, MeCH); 1.99 (t, J=13.0, 1H, CHaxCHMe); 1.97 (d, J=11.4, 1H, CHCHOMe); 1.67–1.16 (m, 5H, CH$_2$CH$_2$CHMe$_2$); 1.18 (s, 3H, CH$_3$); 1.00 (m, 1H, CHeqCHMe); 0.94 (d, J=6.6, 3H, MeCH); 0.89 (2d J=6.6, 6H, Me$_2$CH).

$^{13}$C NMR (62.9 MHz, CDCl$_3$): 167.1, 161.3, 144.6, 129.8, 127.3, 115.9, 114.3, 79.7, 69.3, 61.7, 59.3, 58.4, 56.8, 55.4, 50.7, 47.7, 37.5, 35.7, 31.4, 27.9, 26.0, 22.6, 22.3, 17.2, 13.9.

Example 6

Preparation of (3R,4S,5S,6R,7R)-7-ethyl-6-hydroxy-5-methoxy-4-[(1R,2R)-1,2-epoxy-1,5-dimethylhexyl]-1-oxaspiro[2,5]octane 1. Preparation of (2S,3S,4R,5R)-5-ethyl-4-hydroxy-3-methoxy-2-(1,5-dimethylhex-1-enyl)cyclohexanone

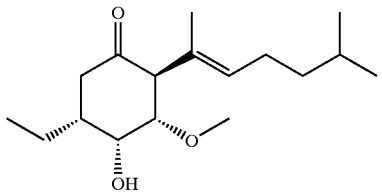

0.55 mL (0.55 mmol, 10 eq) of a 1M solution of Et$_3$Al in hexane is added at 0° C. to a solution of 14 mg (55.5 μmol, 1.0 eq) of (4R,5S,6S)-4-hydroxy-5-methoxy-6-(1,5- dimethylhex-1-enyl)cyclohex-2-enone. The reaction medium is stirred for two hours at room temperature and then poured into 20% tartaric acid solution. The reaction mixture is extracted with ethyl acetate. The organic phases are combined, dried over sodium sulphate and then concentrated to give a colourless oil, which is then chromatographed on preparative silica plates: eluent (7/3 Cy/EtOAc).

8.0 mg of colourless oil are obtained. Yield=51%.

$[\alpha]_D^{20}$=+20° (CHCl$_3$, C=1.05)

$^1$H NMR (250 MHz, CDCl$_3$): 5.18 (tm, J=7.0, 1H, MeC=CH); 4.25 (bs, 1H, CHOH); 3.41 (s, 3H, OCH$_3$); 3.38 (dd, J=2.4, 11.2, 1H, CHOMe); 3.29 (d, J=11.3, 1H, COCHC=C); 2.49 (t, J=13.4, 1H, CHaxCO); 2.35 (bs, 1H, OH); 2.20 (dd, J=3.8, 13.8, 1H, CHeqCO); 2.09 (bq, J=7.3, 2H, C=CHCH$_2$); 1.71–1.45 (m, 4H, CH$_3$CH$_2$CH, CHMe$_2$); 1.61 (s, 3H, CH$_3$C=C); 1.24 (m, 2H, CH$_2$CHMe$_2$); 0.96 (t, J=7.0, 3H, CH$_3$CH$_2$CH); 0.88 (2d, J=6.6, 6H, (CH$_3$)$_2$).

$^{13}$C NMR (62.9 MHz, CDCl$_3$): 208.3, 131.3, 128.8, 82.3, 66.4, 61.0, 57.7, 41.2, 38.7, 38.6, 27.6, 25.9, 25.0, 22.6, 22.5, 14.2, 11.6.

2. Preparation of (2S,3S,4R,5R)-4-benzoyloxy-5-ethyl-3-methoxy-2-(1,5-dimethylhex-1-enyl)cyclohexanone

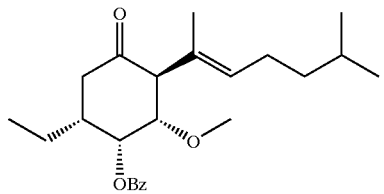

86 mg (0.71 mmol, 10 eq) of benzoic acid, followed immediately by 86 mg (0.71 mmol, 10 eq) of DMAP (4-dimethylaminopyridine) and 146 mg (0.71 mmol, 10 eq) of DCC (dicyclohexylcarbodiimide), are added to a solution of 20 mg (71 µmol, 1.0 eq) of (2S,3S,4R,5R)-5-ethyl-4-hydroxy-3-methoxy-2-(1,5-dimethylhex-1-enyl) cyclohexanone in 2 mL of dichloromethane. The reaction mixture is stirred overnight at room temperature. The solvents are evaporated off and the residue is filtered through a patch of silica (1 cm): eluent (1/1 Cy/EtOAc). The residue is chromatographed on preparative silica plates: eluent (8/2 n-hex/EtOAc).

26 mg of colourless oil are obtained. Yield=92%.

$[\alpha]_D^{20}$=−45° (CHCl$_3$, C=1.25)

$^1$H NMR (250 MHz, CDCl$_3$): 8.05 (d, J=7.0, 2H, ArH); 7.58 & 7.46 (2m, 3H, ArH); 5.99 (bs, 1H, CHOBz); 5.18 (tm, J=6.9, 1H, MeC=CH); 3.54 (dd, J=2.6, 11.6, 1H, CHOMe); 3.43 (s, 3H, OCH$_3$); 3.39 (d, J=11.6, 1H, COCHC=C); 2.53 (t, J=14.6, 1H, CHaxCO); 2.43 (dd, J=4.7, 14.6, 1H, CHeqCO); 2.07 (m, 2H, C=CHCH$_2$); 1.83 (m, 1H, EtCH); 1.60 (s, 3H, CH$_3$C=C); 1.60–1.20 (m, 5H, CH$_2$CHMe$_2$ & MeCH$_2$CH); 0.97 (t, J=7.4, 3H, MeCH$_2$CH); 0.86 (2d, J=6.6, 6H, (CH$_3$)$_2$).

$^{13}$C NMR (62.9 MHz, CDCl$_3$): 207.5, 165.8, 133.2, 132.8, 131.6, 130.0, 129.7, 128.5, 80.6, 68.0, 62.2, 57.7, 42.5, 38.6, 38.1, 27.6, 25.9, 25.0, 22.5, 22.5, 13.9, 11.5.

3. Preparation of (3R,4S,5S,6R,7R)-6-benzoyloxy-7-ethyl-5-methoxy-4-[(E)-1,5-dimethylhexyl]-1-oxaspiro[2,5]octane

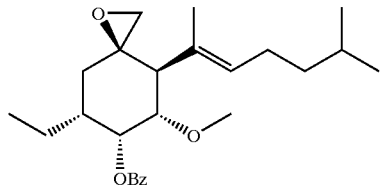

1 mL of DMSO is added to 25 mg (0.62 mmol, 10 eq) of 60% sodium hydride in grease, degreased beforehand in pentane. The reaction medium is stirred for five minutes at room temperature and 204 mg (0.93 mmol, 15 eq) of trimethylsulphoxonium iodide are then added to the above suspension. The reaction mixture is stirred for one hour at room temperature, 1 mL of THF and 99 mg (0.74 mmol, 12 eq) of lithium iodide are added, and the suspension is stirred for 40 minutes at room temperature. A solution of 25 mg (62 µmol, 1.0 eq) of (2S,3S,4R,5R)-4-benzoyloxy-5-ethyl-3-methoxy-2-(1,5-dimethylhex-1-enyl)cyclohexanone in 1 mL of 1/1 DMSO/THF is added at 0° C. The reaction mixture is stirred for two hours at room temperature. The reaction is quenched by adding 5 mL of diethyl ether and 5 mL of pH 7 buffer solution. The medium is extracted with diethyl ether. The organic phases are combined and then dried over anhydrous sodium sulphate. After evaporating off the solvents, the residue is chromatographed on silica gel: eluent (8/2 Cy/EtOAc).

21 mg of colourless oil are obtained. Yield=82%.

$[\alpha]_D^{20}$=−72° (CHCl$_3$, C=1.05)

$^1$H NMR (250 MHz, CDCl$_3$): 8.04 (m, 2H, ArH); 7.55 (m, 1H, ArH); 7.41 (m, 2H, ArH); 5.95 (bs, 1H, CHOBz); 5.22 (tm, J=6.6, 1H, MeC=CH); 3.65 (dd, J=2.7, 11.6, 1H, CHOMe); 3.42 (s, 3H, OCH$_3$); 2.93 (d, J=11.6, 1H, CHCMe=C); 2.73 & 2.51 (2d, J=5.0, 2H, OCH$_2$ epoxide); 2.14 (t, J=13.2, 1H, CHaxCHEt); 2.11–1.86 (m, 3H, EtCH & C=CHCH$_2$); 1.56 (s, 3H, CH$_3$C=C); 1.55–1.15 (m, 6H, CH$_2$CHMe$_2$, MeCH$_2$CH & CHeqCHEt); 0.94 (t, J=7.4, 3H, MeCH$_2$CH); 0.86 (2d, J=6.6, 6H, (CH$_3$)$_2$).

$^{13}$C NMR (62.9 MHz, CDCl$_3$): 166.0, 132.9, 131.2, 130.8, 130.5, 129.7, 128.3, 80.1, 68.8, 60.2, 57.2, 51.2, 49.2, 38.8, 38.3, 35.4, 27.7, 25.7, 24.8, 22.6, 22.4, 14.0, 11.6.

4. Preparation of (3R,4S,5S,6R,7R)-6-benzoyloxy-7-ethyl-5-methoxy-4-[(1R,2R)-1,2-epoxy-1,5-dimethylhexyl]-1-oxaspiro[2,5]octane

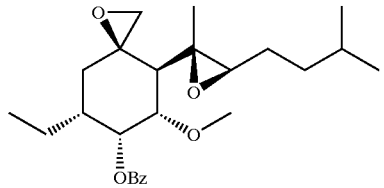

16 mg (68 µmol, 1.5 eq) of 70% meta-chloroperbenzoic acid are added at 0° C. to a solution of 19 mg (45 µmol, 1.0 eq) of (3R,4S,5S,6R,7R)-6-benzoyloxy-7-methyl-5-methoxy-4-[(E)-1,5-dimethylhexyl]-1-oxaspiro[2,5]octane in 2 mL of dichloromethane in the presence of 10 mg (0.126 mmol, 6.0 eq) of sodium hydrogen carbonate. The reaction mixture is stirred for one hour at 0° C. and then for one hour at room temperature. The reaction is quenched by adding 5 mL of saturated sodium hydrogen carbonate solution and then extracted with ethyl acetate. The organic phases are combined and then dried over anhydrous sodium sulphate. After evaporating off the solvents, the residue is chromatographed on preparative silica plates: eluent (7/3 Cy/EtOAc). 16.6 mg of colourless oil are obtained. Yield=84%.

$^1$H NMR (250 MHz, CDCl$_3$): 7.98 (m, 2H, ArH); 7.54 (m, 1H, ArH); 7.41 (m, 2H, ArH); 5.97 (bs, 1H, CHOBz); 3.73 (dd, J=2.7, 11.5, 1H, CHOMe); 3.52 (s, 3H, OCH$_3$); 2.96 & 2.64 (2d, J=4.5, 2H, OCH$_2$ epoxide); 2.56 (dd, J=4.0, 7.0, 1H, OCH epoxide); 2.07 (t, J=13.0, 1H, CHaxCHEt); 2.01 (d, J=11.5, 1H, CHCHOMe); 1.91 (m, 1H, CHEt); 1.68–1.18 (m, 7H, CH$_2$CH$_2$CHMe$_2$ & MeCH$_2$CH); 1.19 (s, 3H, CH$_3$); 1.13 (dd, J=3.5, 13.0, CHeqCHEt); 0.93 (t, J=7.3, 3H, MeCH$_2$CH); 0.89 (2d, J=6.6, 6H, Me$_2$CH).

$^{13}$C NMR (62.9 MHz, CDCl$_3$): 166.0, 132.8, 130.4, 129.7, 128.3, 80.1, 68.3, 61.7, 59.2, 58.2, 57.0, 50.8, 48.3, 38.4, 36.0, 35.7, 27.8, 26.0, 24.6, 22.6, 22.3, 13.9, 11.5.

5. Preparation of (3R,4S,5S,6R,7R)-7-ethyl-6-hydroxy-5-methoxy-4-[(1R,2R)-1,2-epoxy-1,5-dimethylhexyl]-1-oxaspiro[2,5]octane

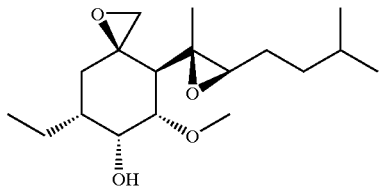

50 mg of potassium carbonate are added to a solution of 16 mg (37 μmol, 1.0 eq) [lacuna] in 1 mL of methanol. The reaction mixture is stirred for 24 hours at room temperature. 10 mL of saturated ammonium chloride solution are added and the medium is then extracted with ethyl acetate. The organic phases are combined and then dried over anhydrous sodium sulphate. After evaporating off the solvents, the residue is chromatographed on preparative silica plates: eluent (6/4 Cy/EtOAc).

7 mg of colourless oil are obtained. Yield=58%.

$^1$H NMR (250 MHz, CDCl$_3$): 4.27 (bs, 1H, CHOH); 3.60 (dd, J=2.6, 11.3, 1H, CHOMe); 3.50 (s, 3H, OCH$_3$); 2.86 & 2.58 (2d, J=4.3, 2H, OCH$_2$ epoxide); 2.54 (dd, J=4.4, 7.5, 1H, OCH epoxide); 2.19 (bs, 1H, CHOH); 1.98 (t, J=12.9, 1H, CHaxCHEt); 1.92 (d, J=11.3, 1H, CHCHOMe); 1.68–1.20 (m, 8H, CHEt, CH$_2$CH$_2$CHMe$_2$ & MeCH$_2$CH); 1.18 (s, 3H, CH$_3$); 0.97 (t, J=7.4, 3H, MeCH$_2$CH); 0.96 (m, 1H, CHeqCHEt); 0.89 (2d, J=6.6, 6H, Me$_2$CH).

Example 7

(3R,4S,5S,6R,7R)-7-ethyl-5-methoxy-4-[(1R,2R)-1,2-epoxy-1,5-dimethylhexyl]-1-oxaspiro[2,5]oct-6-yl 4-methoxycinnamate

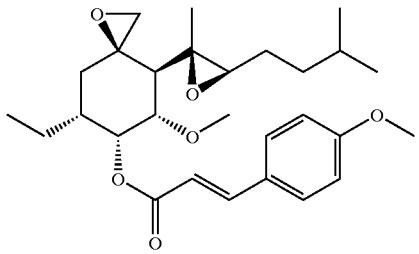

62 mg (0.35 mmol, 12 eq) of p-methoxycinnamic acid, followed immediately by 43 mg (0.35 mmol, 12 eq) of DMAP (4-dimethylaminopyridine) and 72 mg (0.35 mmol, 12 eq) of DCC (dicyclohexylcarbodiimide), are added to a solution of 9 mg (29 μmol, 1.0 eq) of (3R,4S,5S,6R,7R)-7-ethyl-6-hydroxy-5-methoxy-4-[(1R,2R)-1,2-epoxy-1,5-dimethylhexyl]-1-oxaspiro[2,5]octane in 2 mL of dichloromethane. The reaction mixture is stirred overnight at room temperature. The solvents are evaporated off and the residue is filtered through a patch of silica (1 cm): eluent (1/1 Cy/EtOAc). The residue is then chromatographed on preparative silica plates: eluent (8/2 n-hex/EtOAc).

12.3 mg of colourless oil are obtained. Yield=90%.

$[\alpha]_D^{20}$=−43° (CHCl$_3$, C=0.6) (contains 10% of cis isomer).

$^1$H NMR (250 MHz, CDCl$_3$): 7.61 (d, J=16.0, 1H, COCH=CH); 7.46 & 6.89 (2d, J=8.7, 4H, ArH); 6.32 (d, J=16.0, 1H, COCH=CH); 5.85 (bs, 1H, CHOCO); 3.83 (s, 3H, ArOCH$_3$); 3.68 (dd, J=2.7, 11.5, 1H, CHOMe); 3.49 (s, 3H, OCH$_3$); 2.93 & 2.61 (2d, J=4.4, 2H, OCH$_2$epoxide); 2.56 (dd, J=4.2, 7.5, 1H, OCHepoxide); 1.99 (d, J=11.3, 1H, CHCHOMe); 1.98 (t, J=12.7, 1H, CHaxCHEt); 1.86 (m, 1H, EtCH); 1.67–1.18 (m, 7H, CH$_3$CH$_2$CH & CH$_2$CH$_2$CHMe$_2$); 1.20 (s, 3H, CH$_3$); 1.08 (dd, J=3.0, 12.9, 1H, CHeqCHEt); 0.92 (t, J=7.3, 3H, MeCH$_2$CH); 0.89 (2d, J=6.6, 6H, Me$_2$CH).

$^{13}$C NMR (62.9 MHz, CDCl$_3$): 166.9, 161.3, 144.5, 129.7, 127.3, 115.9, 114.3, 80.0, 67.5, 61.7, 59.3, 58.4, 56.9, 55.4, 50.8, 48.0, 38.3, 35.8, 35.7, 27.9, 26.0, 24.6, 22.6, 22.3, 13

Example 8

(3R,4S,5S,6R)-4-(cyclohex-1-enyl)-5-methoxy-1-oxaspiro[2,5]oct-6-yl 4-methoxycinnamate

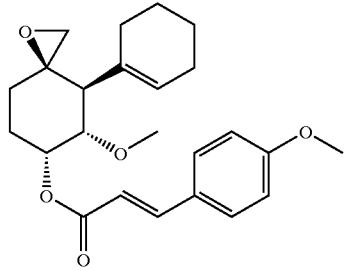

1. Preparation of (4R)-4-benzyl-3-(2-cyclohex-1-enylacetyl) oxazolidin-2-one

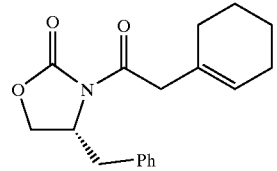

In the same manner as for the preparation of (4R)-4-benzyl-3-(3,7-dimethyloct-3-enoyl)oxazolidin-2-one, starting with 1.6 g (11.43 mmol) of 2-cyclohex-1-enylacetic acid and 2.217 g of (R)-(+)-4-benzyl-2-oxazolidinone, 2.051 g (60%) of (4R)-4-benzyl-3-(2-cyclohex-1-enylacetyl) oxazolidin-2-one are obtained.

$^1$H NMR (250 MHz, CDCl$_3$): 7.40–7.20 (m, 5H, ArH); 5.59 (bs, C=CH); 4.67 (dddd, J=3.0, 3.5, 7.0, 10.0, 1H, CHN); 4.18 (ABX, 2H, CH$_2$O); 3.59 (AB, 2H, COCH$_2$); 3.35 (dd, J=3.2, 13.5, 1H, CHPh); 2.75 (dd, J=9.7, 13.5, 1H, CHPh); 2.06 (m, 4H, CH$_2$C=CHCH$_2$); 1.75–1.50 (m, 4H, CH$_2$—CH$_2$—C=CH CH$_2$—CH$_2$).

2. Preparation of (4R)-4-benzyl-3-[(2S,3S,4R)-2-(cyclohex-1-enyl)-3-hydroxy-4-p-methoxybenzyloxyhex-5-enoyl]oxazolidin-2-one

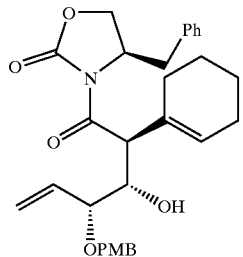

0.9 mL (1.44 mmol) of a 1.6M solution of butyllithium in hexane is added at 0° C. to a solution of 204 µL of diisopropylamine in 2.5 mL of THF. The reaction medium is stirred for one hour at −78° C. A solution of 430 mg (1.44 mmol) of (4R)-4-benzyl-3-(2-cyclohex-1-enylacetyl)oxazolidin-2-one in 2.5 mL of THF is then added using a cannula. After stirring for 1.5 hours at −78° C., a solution of 575 mg (1.1 eq) of 2-(R)-4-phenylselenyl-2-p-methoxybenzyloxybutanal in 2.5 mL of THF is added using a cannula.

The reaction mixture is stirred for 1.5 hours at −78° C. and the reaction is then quenched by adding 5 mL of saturated ammonium chloride solution.

The flask is warmed to 20° C. and then extracted with diethyl ether. The organic phases are combined and then dried over anhydrous sodium sulphate. After evaporating off the solvents, the residue is redissolved in 10 mL of chloroform, 1.2 g (2.8 mmol) of tetrabutylammonium periodate are then added and the reaction mixture is stirred for two hours at 60° C.

The chloroform is evaporated off and the residue is then filtered through silica gel (4 cm) eluent: (9/1 Cy/EtOAc).

The filtrate is concentrated and then chromatographed on silica gel: eluent (8/2 Cy/EtOAc).

228 mg of aldol are obtained. Yield=31%.

$^1$H NMR (250 MHz, CDCl$_3$): 7.40–7.10 (m, 7H, ArH); 6.85 (d, J=8.7, 2H, ArH); 5.91 (m, CH=CH$_2$); 5.83 (bs, C=CH); 5.43 and 5.34 (2dd, J=1.7, 10.3, and J=1.2, 17.2, 2H, CH$_2$=CH); 4.74 (d, J=8.7, 1H, NCOCHC=C); 4.54 (d, J=10.8, 1H, CH$_2$pC$_6$H$_4$OMe); 4.43 (m, 1H, PhCH$_2$CHN); 4.29 (m, 1H, CHOH); 4.26 (d, J=10.8, 1H, CH$_2$pC$_6$H$_4$OMe); 4.04 (t, J=9, 1H, NCOOCH$_{2a}$); 3.96 (dd, J=2.5, 9, 1H, NCOOCH$_{2b}$) 3.75 (m, 1H, CHOPMB); 3.69 (s, 3H, OCH$_3$); 3.08 (dd, J=2.8, 13.1, 1H, CHPh); 2.26 (d, J=3.3, 1H, OH); 2.2–1.9 (m, 4H, CH$_2$C=CHCH$_2$); 1.85 (dd, J=11, 13.1, 1H, CHPh); 1.7–1.5 (m, 4H, CH$_2$—CH$_2$—C=CH CH$_2$—CH$_2$).

3. Preparation of (2S,3S,4R)-2-(cyclohex-1-enyl)-3-methoxy-4-p-methoxybenzyloxyhex-5-enoic acid methoxymethylamide

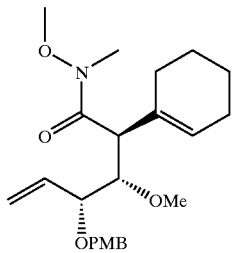

3.15 mL of a 2M solution of trimethylaluminium in toluene are added at 0° C. to a suspension of 614 mg of N,O-dimethylhydroxylamine hydrochloride in 2 mL of THF. The reaction mixture is stirred for 30 minutes at room temperature and then cooled to 0° C. A solution of 912 mg of (4R)-4-benzyl-3-[(2S,3S,4R)-2-(cyclohex-1-enyl)-3-hydroxy-4-p-methoxybenzyloxyhex-5-enoyl]oxazolidin-2-one in 3 mL of THF is added at 0° C. and the reaction medium is then stirred overnight at room temperature. The reaction mixture is poured into cold 10% tartaric acid solution and then extracted with ethyl acetate. The organic phases are combined and then dried over anhydrous sodium sulphate. After evaporating off the solvents, the residue is chromatographed on a short column (5×5 cm) of silica gel: eluent (8/2 Cy/EtOAc) to give 626 mg of 2(S)-2-[(1S,2R)-1-hydroxy-2-p-methoxybenzyloxybut-3-enyl]-2-cyclohex-1-enylacetic acid, which is dissolved in ether (5 mL) and treated with MeI (1.6 mL) in the presence of Ag$_2$O (1.7 g) and 4 Å molecular sieves (400 mg). The reaction mixture is stirred overnight, under argon, at 45° C. After working up the reaction and chromatography on silica gel: eluent (5/1 Cy/EtOAc), 329 mg (45%) of (2S,3S,4R)-2-(cyclohex-1-enyl)-3-methoxy-4-p-methoxybenzyloxyhex-5-enoic acid methoxymethylamide are obtained.

$^1$H NMR (250 MHz, CDCl$_3$): 7.25 & 6.84 (2d, J=8.6, 4H, ArH); 5.91 (ddd, J=8.1, 10.3, 17.2, 1H, CH=CH$_2$); 5.66 (bs, 1H, C=CH); 5.31 (dd, J=1.9, 10.3, 1H, CH$_2$=CH); 5.20 (dd, J=1.7, 17.5, 1H, CH$_2$=CH); 4.50 and 4.34 (2d, J=11.5, 2H, CH$_2$pC$_6$H$_4$OMe); 3.99 (dd, J=2.9, 10, 1H, CHOMe); 3.79 (s, 3H, ArOCH$_3$); 3.77 (m, 1H, NCOCHC=C); 3.59 (s, 3H, NOCH$_3$); 3.49 (s, 3H, CHOCH$_3$); 3.67 (m, 1H, CHOPMB); 3.55–3.45 (m, 1H, CHOPMB); 3.13 (s, 3H, NCH$_3$); 2.2–1.9 (m, 4H, CH$_2$C=CHCH$_2$); 1.7–1.5 (m, 4H, CH$_2$—CH$_2$—C=CH CH$_2$—CH$_2$).

4. Preparation of (4S,5S,6R)-4-(cyclohex-1-enyl)-5-methoxy-6-p-methoxybenzyloxyocta-1,7-dien-3-one

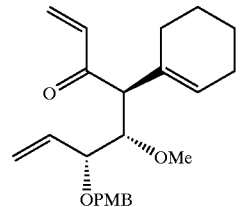

279 mg (0.69 mmol) of (2S,3S,4R)-2-(cyclohex-1-enyl)-3-methoxy-4-p-methoxybenzyloxyhex-5-enoic acid methoxymethylamide are dissolved in THF (4 mL) and treated, at 0° C., with an excess of vinylmagnesium bromide (as a 1M solution in THF, 2.76 mL, 2.76 mmol, 4 equivalents). After addition, the mixture is allowed to warm to room temperature and is stirred overnight. An excess of saturated NH$_4$Cl in a 1:1 THF/water mixture is then added. After extraction and evaporation of the solvents, the residue is chromatographed on silica (eluent (5/1 Cy/EtOAc)) to give 187 mg (73%) of (4S,5S,6R)-4-(cyclohex-1-enyl)-5-methoxy-6-p-methoxybenzyloxyocta-1,7-dien-3-one.

$^1$H NMR (250 MHz, CDCl$_3$): 7.23 & 6.86 (2d, J=8.6, 4H, ArH); 6.37 (dd, J=10.1, 17.4, 1H, CH$_2$=CHCO); 6.18 (dd, J=1.8, 17.4, 1H, CH$_2$=CHCO); 5.87 (ddd, J=8.2, 10.3,17.3, 1H, CH$_2$=CHCHOPMB); 5.64 (dd, J=1.8, 10.1, 1H, CH$_2$=CHCO); 5.63 (bs, 1H, C=CH); 5.31 (dd, J=1.8, 10, 1H, CH$_2$=CH); 5.15 (dd, J=1.3, 17.2, 1H, CH$_2$=CH); 4.49 and 4.29 (2d, J=11.4, 2H, CH$_2$pC$_6$H$_4$OMe); 4.01 (dd, J=3.7, 9.4, 1H, CHOMe); 3.80 (s, 3H, ArOCH$_3$); 3.68 (dd, J=3.6, 8.2, 1H, CHOPMB); 3.49 (s, 3H, OCH$_3$); 3.42 (d, J=9.4, 1H, COCHC=C); 2.03 & 1.95 (2×m, 4H, CH$_2$C=CHCH$_2$); 1.7–1.5 (m, 4H, CH$_2$—CH$_2$—C=CH CH$_2$—CH$_2$).

5. Preparation of (2S,3S,4R)-2-(cyclohex-1-enyl)-3-methoxy-4-p-methoxybenzyloxycyclohexanone

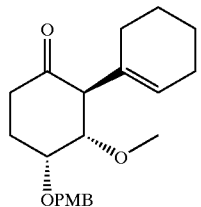

In a Sclenck tube, under an argon atmosphere, 187 mg (0.50 mmol) of (4S,5S,6R)-4-(cyclohex-1-enyl)-5-methoxy-6-p-methoxybenzyloxyocta-1,7-dien-3-one dissolved in dichloromethane (4 mL) containing 59 μL (0.4 equivalent) of Ti(OiPr)$_4$, and 82 mg (0.2 equivalent) of catalyst are refluxed for 12 hours. After working up in a manner similar to that of Example 4(8), the intermediate cyclohexenone obtained (43 mg) is treated directly with Raney nickel (6 drops of suspension). After working up in a manner similar to that of Example 4(9), 39 mg of (2S,3S,4R)-2-(cyclohex-1-enyl)-3-methoxy-4-p-methoxybenzyloxycyclohexanone are obtained.

$^1$H NMR (250 MHz, CDCl$_3$): 7.33 & 6.88 (2d, J=8.6, 4H, ArH); 5.43 (m, 1H, C=CH); 4.67 (s, 2H, OCH$_2$pC$_6$H$_4$OMe); 4.11 (m, 1H, CHOPMB); 3.81 (s, 3H, ArOCH$_3$); 3.5–3.3 (m, 2H, COCHC=C & CHOMe); 3.33 (s, 3H, OCH$_3$); 2.70–2.50 (m, 1H, CH$_{2a}$CO); 2.30–2.14 (m, 11H).

6. Preparation of (3R,4S,5S,6R)-4-(cyclohex-1-enyl)-5-methoxy-6-p-methoxybenzyloxy-1-oxaspiro[2,5]octane

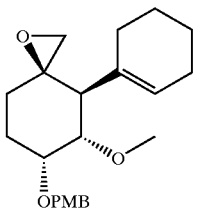

385 mg (1.74 mmol) of trimethylsulphoxonium iodide are added to a suspension of sodium hydride (28 mg, 1.16 mmol) in 1 mL of DMSO. The mixture is stirred for 40 minutes, followed by successive addition of 1 mL of THF and 186 mg of anhydrous lithium iodide. The mixture is stirred for a further 30 minutes, cooled to 0° C., and 39 mg (0.11 mmol) of (2S,3S,4R)-2-(cyclohex-1-enyl)-3-methoxy-4-p-methoxybenzyloxy-cyclohexanone dissolved in 0.5 mL of THF are added. The bath is removed and the reaction is allowed to continue for 40 minutes at room temperature. After adding pH 7 buffer, extracton and evaporation of the solvents, the product is purified by chromatography on a preparative silica plate (eluent: 1:1 ether/pentane) to give 19 mg (45%) of (3R,4S,5S,6R)-4-(cyclohex-1-enyl)-5-methoxy-6-p-methoxybenzyloxy-1-oxaspiro[2,5]octane in the form of a colourless oil.

[α]$_D^{20}$=−68° (CHCl$_3$, C=0.85)

$^1$H NMR (250 MHz, CDCl$_3$): 7.32 & 6.87 (2d, J=8.6, 4H, ArH); 5.49 (m, 1H, C=CH); 4.61 (s, 2H, OCH$_2$pC$_6$H$_4$OMe); 4.04 (m, 1H, CHOPMB); 3.80 (s, 3H, ArOCH$_3$); 3.48 (dd, J=2.4, 11, 1H, CHOMe); 3.32 (s, 3H, OCH$_3$); 2.94 (d, J=11, 1H, CHC=C); 2.68 & 2.45 (2d, J=5.0, 1H, OCH$_2$ epoxide); 2.19 (dt, J=4.3, 13.3, 13.3, 1H, CH$_2$'axCO); 2.10–1.50 (m, 11H); 1.10 (dm, J=13.5, 1H, CH$_2$eqCO).

7. Preparation of (3R,4S,5S,6R)-4-(cyclohex-1-enyl)-5-methoxy-1-oxaspiro[2,5]oct-6-yl4-methoxycinnamate

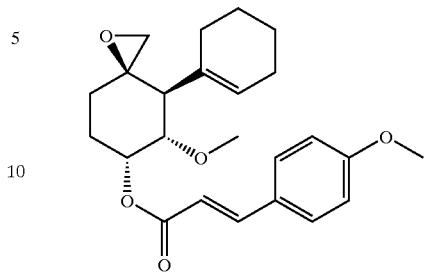

19 mg (0.055 mmol) of (3R,4S,5S,6R)-4-(cyclohex-1-enyl)-5-methoxy-6-p-methoxybenzyloxy-1-oxaspiro[2,5] octane are dissolved in 1 mL of dichloromethane containing 40 μL of H$_2$O. 14 mg of DDQ (2,3-dichloro-5,6-dicyano-1,4-benzoquinone) are added and the mixture is stirred at 20° C. for 20 minutes. Saturated NaHCO$_3$ solution is added and the mixture is extracted with ether and evaporated. The residue is dissolved in 1 mL of dichloromethane, followed by addition of p-methoxycinnamic acid (97 mg), DMAP (4-dimethylaminopyridine) (67 mg) and DCC (dicyclohexylcarbodiimide) (112 mg). The resulting mixture is stirred overnight at room temperature. The solvent is evaporated off and the residue is extracted with pentane. The product is purified by preparative chromatography on a silica plate (eluent 1:1 ether/pentane) to give 9 mg (42%) of (3R,4S,5S,6R)-4-(cyclohex-1-enyl)-5-methoxy-1-oxaspiro [2,5]oct-6-yl 4-methoxycinnamate (containing 90% trans isomer and 10% cis isomer).

$^1$H NMR (250 MHz, CDCl$_3$): 7.65 (d, J=16, 1H, COCH=CH); 7.48 and 6.90 (2d, J=8.8, 4H, ArH); 6.37 (d, J=16, 1H, COCH=CH); 5.70 (m, 1H, CHOCO); 5.49 (m, 1H, C=CH), 3.84 (s, 3H, ArOCH$_3$); 3.64 (dd, J=2.8, 11, 1H, CHOMe); 3.37 (s, 3H, OCH$_3$); 3.19 (m, 1H), 2.88 (d, J=11, 1H, CHC=C); 2.72 and 2.51 (2d, J=5, 2H, OCH$_2$epoxide); 2.18 (dt, J=4.4, 13.5, 13.5, 1H, CH$_2$axCO); 2.10–1 (m, 10H).

Example 9

Preparation of (3R,4S,5S,6R,7S)-4-(1,5-dimethylhex-1-enyl)-5-methoxy-7-methyl-1-oxaspiro[2,5]oct-6-yl 4-methoxycinnamate

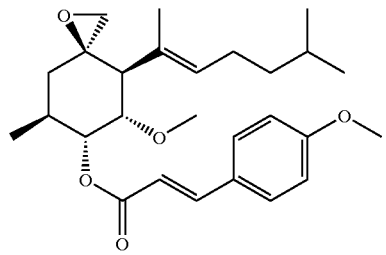

C$_{27}$H$_{38}$O$_5$M = 442.60 a. Preparation of (2S,3S,4R,5S)-2-(1,5-dimethylhex-1-enyl)-3-methoxy-4-(4-methoxybenzyloxy)-5-methylcyclohexanone

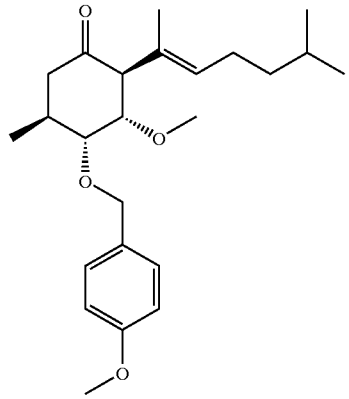

422 μL (0.59 mmol, 2.2 eq) of a 1.4 M solution of MeLi in diethyl ether are added to a suspension, at 0° C., of 56 mg (0.29 mmol, 1.1 eq) of copper I iodide in 1 mL of diethyl ether. The solution is stirred for one hour at 0° C. and a solution of 100 mg (0.27 mmol, 1 eq) of (4R,5S,6S)-5-methoxy-4-p-methoxybenzyloxy-6-(1,5-dimethylhex-1-enyl)cyclohex-2-enone in 0.5 mL of diethyl ether is added. The mixture is stirred for one hour at 0° C. and the reaction is then quenched by adding 2 mL of saturated ammonium chloride solution and extracted with ether. The organic phases are dried over magnesium sulphate. After evaporating off the solvents, the residue is chromatographed on a preparative silica plate (eluent: 8/2 n-hexane/EtOAc).

80 mg of a colourless oil are obtained. Yield=77%.

$R_f$=0.25 (Cy/EtOAc 4/1).

$^1$H NMR (400 MHz, CDCl$_3$): 0.81 (d, 6H, J=6.8 Hz, (CH$_3$)$_2$), 0.92 (d, 3H, J=7.2 Hz, CH$_3$—CH), 1.15 (m, 2H, CH$_2$—CHMe$_2$), 1.46 (m, 1H, CH(Me)$_2$), 1.50 (s, 3H, CH$_3$C═C), 2.05 (m, 3H, CH$_2$—C═C and CHH—C═O), 2.36 (m, 1H, Me—CH), 2.57 (dd, 1H, J=14.5, 6.0 Hz, CHH—C═O), 3.28 (s, 3H, CH$_3$O), 3.31 (m, 1H, CH—C═O), 3.60 (dd, 1H, J=8.5, 2 Hz, CH—OMe), 3.65 (dd, 1H, J=6.0, 2.0 Hz, CH—O—PMB), 3.73 (s, 3H, O—CH$_3$), 4.56 and 4.63 (2d, 2H, AB, J=11.8 Hz, CH$_2$—Ar), 5.03 (t, 1H, J=7.0 Hz, C═CH), 6.81 and 7.24 (2d, 4H, J=8.4 Hz, ArH).

$^{13}$C NMR (100 MHz, CDCl$_3$): 15.11 (CH$_3$—C═C), 18.8 (CH$_3$—CH), 22.9 ((CH$_3$)$_2$—C═C), 26.3 (CH$_2$—HC═C), 28.1 (CH—(CH$_3$)$_2$), 31.8 (CH—(CH$_3$)), 39.0 (CH$_2$—CH—(CH$_3$)$_2$), 44.2 (CH$_2$—C═O), 55.7 (CH$_3$—O), 58.0 (CH$_3$—O), 62.3 (CH—C═O), 72.1 (CH$_2$—Ar), 77.4 (CH—OPMB), 79.4 (CH—O—CH$_3$), 114.1 (Ar), 129.7 (Ar), 130.4 (CH═C), 131 (Ar$^{IV}$), 159.6 (Ar$^{IV}$), 210.0 (C═O).

$[\alpha]_D^{20}$=+43° (CHCl$_3$, C=1.1)

b. Preparation of (3R,4S,5S,6R,7S)-4-(1,5-dimethylhex-1-enyl)-5-methoxy-6-(4-methoxybenzyloxy)-7-methyl-1-oxaspiro[2,5]octane

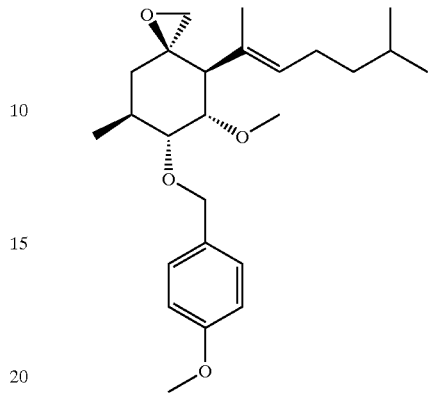

520 μL (0.835 mmol, 5.0 eq) of a 1.6 M solution of BuLi in hexane are added to a solution, at −78° C., of 65 mg (0.167 mmol, 1.0 eq) of (2S,3S,4R,5S)-2-(1,5-dimethylhex-1-enyl)-3-methoxy-4-(4-methoxybenzyloxy)-5-methylcyclohexanone and 68 μL (0.835 mmol, 5.0 eq) of diiodomethane in 1 mL of THF. The solution is stirred for one hour at −78° C. and then for 1.5 hours at room temperature. The reaction is quenched by adding 1 mL of an ammonium chloride solution and then extracted with ethyl acetate. The organic phases are combined and then dried over anhydrous sodium sulphate. After evaporating off the solvents, the residue is chromatographed on a preparative silica plate: eluent (8/2 Cy/EtOAc).

35 mg of colourless oil are obtained. Yield 52%.

$R_f$=0.25 (9/1 Cy/EtOAc).

$^1$H NMR (400 MHz, CDCl$_3$): 0.88 and 0.89 (2d, 6H, J=6.6 Hz, (CH$_3$)$_2$), 1.04 (d, 3H, J=7.0 Hz, CH$_3$—CH), 1.22 (m, 2H, CH$_2$—CH(Me)$_2$), 1.32 (dd, J=13.7, 5.8 Hz, 1H, CHHax-CH(Me)), 1.54 (m, 1H, CH(Me)$_2$), 1.57 (s, 3H, CH$_3$C═C), 1.93 (dd, J=13.7, 5.0 Hz, 1H, CHHequ-CH(Me)), 2.02 (m, 2H, CH$_2$C═C), 2.26 (m, 1H, Me—CH), 2.38 and 2.54 (2d, J=5.0 Hz, CH$_2$(spiro-epoxide)), 2.71 (d, 1H, J=8.0 Hz, CH(OMe)—CH—C(spiro-epoxide)), 3.34 (s, 3H, CH$_3$—O), 3.54 (bd, J=4.3 Hz, 1H, CH—O—PMB), 3.70 (dd, 1H, J=8.3, 2.0 Hz, CH—OMe), 3.80 (s, 3H, Ar—O—CH$_3$), 4.58 (2d, 2H, AB, J=11.8 Hz, CH2—Ar), 5.29 (m, 1H, C═CH), 6.87 and 7.29 (2d, 4H, J=8.3 Hz, ArH).

$^{13}$C NMR (100 MHz, CDCl$_3$): 14.9 (CH$_3$—C═C), 18.1 (CH$_3$—CH), 22.5 and 22.6 ((CH$_3$)$_2$), 25.9 (CH$_2$—HC═C), 27.8 (CH—(CH$_3$)$_2$), 31.7 (CH—CH$_3$), 35.6 (CH$_2$—CH(CH$_3$)) 38.8 (CH$_2$—CH(CH$_3$)$_2$), 49.5 (CH—CH(OMe)—CH(OPMB)), 51.0 (CH$_2$ spiro-epoxide), 55.3 (Ar—O—CH$_3$), 57.0 (CH$_3$—O), 58.8 (C-spiro-epoxide), 71.4 (CH$_2$—Ar), 77.7 (CH—OPMB), 78.0 (CH—OMe), 113.7 (Ar), 129.2 (Ar), 130.0 (CH═C), 131 (Ar and CH═C), 159.1 (Ar).

$[\alpha]_D^{20}$=−12° (CHCl$_3$, C=1.75)

c. Preparation of (3R,4S,5S,6R,7S)-4-(1,5-dimethylhex-1-enyl)-5-methoxy-7-methyl-1-oxaspiro[2,5]octan-6-ol

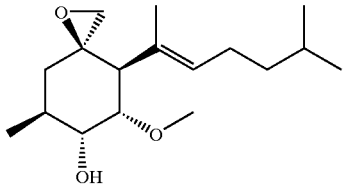

22 mg (96 μmol, 1.1 eq) of DDQ are added to a solution of 35 mg (87 μmol, 1 eq) of (3R,4S,5S,6R,7S)-4-(1,5-dimethylhex-1-enyl)-5-methoxy-6-(4-methoxybenzyloxy)-7-methyl-1-oxaspiro[2,5]octane in 3 mL of $CH_2Cl_2$ in the presence of 85 μL of water.

The reaction mixture is stirred for 1 hour 30 minutes at room temperature. The reaction is quenched by adding 0.5 mL of saturated sodium hydrogen carbonate solution and then extracted with ethyl acetate. The organic phases are combined, dried over sodium sulphate and then concentrated. The residue obtained is then chromatographed on preparative silica plates (eluent: 8/2 Cy/EtOAc).

20.0 mg of colourless oil are obtained. Yield 80%.

$R_f$=0.25 (4/1 Cy/EtOAc).

$^1$H NMR (400 MHz, $CDCl_3$): 0.88 (d, 6H, J=6.4 Hz, $(CH_3)_2$), 1.10 (d, 3H, J=7.6 Hz, $CH_3$—CH), 1.22 (m, 3H, $CH_2$—$CH(Me)_2$ and CHH—CH(Me)), 1.53 (m, 1H, $CHMe_2$), 1.60 (s, 3H, $CH_3C$=C), 1.95–2.10 (m, 3H, CHH—CH(Me) and $CH_2$—C=C), 2.18 (m, 1H, Me—CH), 2.34 (bs, 1H, CHOH), 2.36 and 2.51 (2d, J=5.2 Hz, $CH_2$ (spiro-epoxide)), 2.66 (d, 1H, J=9.0, CH(OMe)—CH—C (spiro-epoxide)), 3.39 (s, 3H, $CH_3$—O), 3.68 (dd, J=9.0, 2.5 Hz, 1H, CH—O—Me), 3.89 (m, 1H, CH—OH), 5.28 (t, 1H, J=7.0 Hz, C=CH).

$^{13}$C NMR (100 MHz, $CDCl_3$): 15.11 ($CH_3$—C=C), 17.8 ($CH_3$—CH), 22.5 and 22.6 ($(CH_3)_2$), 25.9 ($CH_2$—HC=C), 27.7 (CH—$(CH_3)_2$), 33.4, 33.6, 38.8 ($CH_2$—CH—$(CH_3)_2$), 48.5 ($CH_2$-spiro-epoxide), 50.0 (CH—OMe—CH—C-spiro-epoxide), 57.1 ($CH_3$—O), 58.9 (C-spiro-epoxide), 70.7 (CH—OH), 79.3 (CH—O—$CH_3$), 130.4 (CH=C), 130.7 (CH=C).

d. Preparation of (3R,4S,5S,6R,7S)-4-(1,5-dimethylhex-1-enyl)-5-methoxy-7-methyl-1-oxaspiro[2,5]oct-6-yl 4-methoxycinnamate

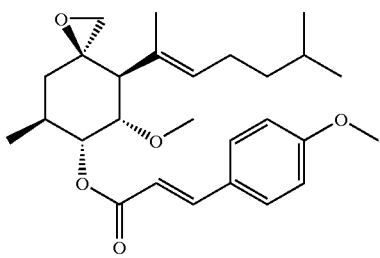

185 mg (1.04 mmol, 12 eq) of p-methoxycinnamic acid, followed immediately by 127 mg (1.04 mmol, 12 eq) of DMAP and 215 mg (1.04 mmol, 12 eq) of DCC, are added to a solution of 25 mg (0.087 mmol, 1.0 eq) of (3R,4S,5S,6R,7S)-4-(1,5-dimethylhex-1-enyl)-5-methoxy-7-methyl-1-oxaspiro[2,5]octan-6-ol in 2 mL of dichloromethane. The reaction mixture is stirred overnight at room temperature. The solvents are evaporated off and the residue is filtered through a patch of silica (1 cm): eluent (1/1 Cy/EtOAc). The residue is then chromatographed on a preparative silica plate: eluent (85/15: n-hex/EtOAc).

18 mg of colourless oil are obtained. Yield 49%.

$R_f$=0.3 (9/1 Cy/EtOAc).

$^1$H NMR 400 MHz, $CDCl_3$): 0.89 (d, 6H, J=6.4 Hz, $(CH_3)_2$), 1.13 (d, 3H, J=7.2 Hz, $CH_3$—CH), 1.26 (m, 2H, $CH_2$—$CH(Me)_2$), 1.45 (dd, J=13.5, 5.6 Hz, 1H, CHHeq-CH(Me)—CH(OPMB)), 1.55 (m, 1H, $CH(Me)_2$), 1.65 (s, 3H, $CH_3$—C=C), 1.98 (dd, J=13.5, 4.5 Hz, 1H, CHHax-CH(Me)—CH(OPMB)), 2.05 (m, 2H, $CH_2$—CH=C), 2.32 (m, 1H, Me—CH), 2.44 and 2.60 (2d, J=5.0 Hz, $CH_2$(spiro-epoxide)), 2.70 (d, 1H, J=8.3, CH(OMe)—CH—C=C), 3.36 (s, 3H, $CH_3$—O), 3.83 (s, 3H, Ar—O—$CH_3$), 3.87 (m, 1H, CH—OMe), 5.25 (m, 1H, CH—COO), 5.40 (t, J=6.8 Hz, 1H, C=CH), 6.38 (d, J=16.0 Hz, 1H, Ar—CH=C), 6.91 and 7.48 (2d, 4H, J=8.8 Hz, ArH), 7.66 (d, J=16.0 Hz, 1H, COO—CH=C).

$^{13}$C NMR (100 MHz, $CDCl_3$): 14.8 ($CH_3$—C=C), 17.9 ($CH_3$—CH), 22.5 (($CH_3)_2$), 25.9 ($CH_2$—CH=C), 27.8 (CH—$(CH_3)_2$), 32.0 (CH—$CH_3$), 35.5 ($CH_2$—$CH(CH_3)$), 38.8 ($CH_2$—CH—$(CH_3)_2$), 50.0 (CH—CH(OMe)—CH (OPMB)), 50.7 ($CH_2$-spiro-epoxide), 55.3 (Ar—O—$CH_3$), 57.5 ($CH_3$—O), 58.6 ($C^{IV}$-spiro-epoxide), 73.0 (CH—COO), 77.3 (CH—OMe), 114.3 (Ar), 115.8 (C=CH—Ar), 127.2 (MeC=CH), 130.3 (MeC=CH), 130.5 ($Ar^{IV}$), 129.8 (Ar), 144.6 (COO—CH=C), 161.4 ($Ar^{IV}$), 166.9 (COO).

$[\alpha]_D^{20}$=−49° ($CHCl_3$, C=0.9)

Example 10

Preparation of (3R,4S,5S,6R,7S)-4-(1,5-dimethylhex-1-enyl)-7-hydroxy-5-methoxy-1-oxaspiro[2,5]oct-6-yl 4-methoxycinnamate

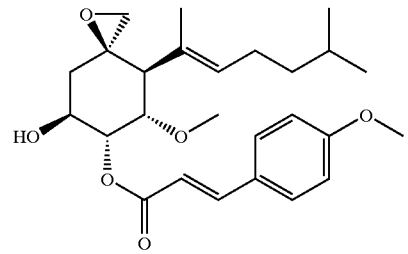

$C_{26}H_{36}O_6$M = 444.57 a. Preparation of (1R,3S,4S,5R,6S)-3-(1,5-dimethylhex-1-enyl)-4-methoxy-5-(4-methoxybenzyloxy)-7-oxabicyclo[4.1.0]heptan-2-one

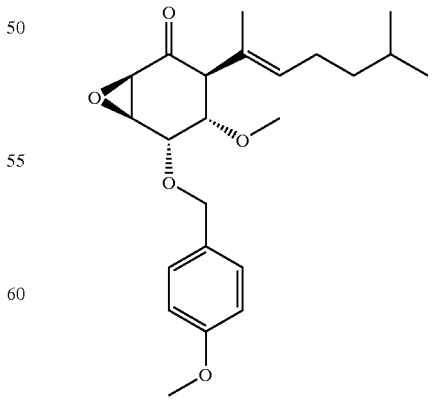

TBHP (0.135 mL, 0.671 mmol, 5 eq, 5–6 M in decane) and then Triton B (6 μl, 13 μmol, 0.1 eq) are added to a solution, at 0° C., of (4R,5S,6S)-5-methoxy-4-p-methoxybenzyloxy-6-(1,5-dimethylhex-1-enyl)cyclohex-2-enone (50 mg, 0.134 mmol) in 0.5 ml of THF. After 30 minutes at 0° C., the reaction is quenched by adding ammonium chloride solution and is then extracted with hexane. The organic phases are combined, dried over sodium sulphate and then concentrated to give a yellow oil, which is then purified on preparative silica plates: eluent: 85/15 Hex/EtOAc.

40 mg of yellow oil are obtained. Yield 77%

$R_f$=0.2 4/1 Cy/EtOAc.

$^1$H NMR (400 MHz, CDCl$_3$): 0.89 (d, 6H, J=6.4 Hz, (CH$_3$)$_2$), 1.20–1.29 (m, 3H, CH$_2$—CH(Me)$_2$ and CH(Me)$_2$), 1.43 (s, 3H, CH$_3$—C=C), 2.06 (m, 2H, CH$_2$—CH=C), 3.10 (d, 1H, J=10.1 Hz, CO—CH), 3.27 (d, 1H, J=3.8 Hz, CO—CH—O), 3.37 (s, 3H, CH$_3$—O), 3.47 (t, 1H, J=3.8 Hz, CH(OPMB)—CH—CH—C=O), 3.78 (dd, J=10.1 and 2.5 Hz, CH—OMe), 3.81 (s, 3H, Ar—O—CH$_3$), 4.45 (dd, 1H, J=3.6 and 2.7 Hz, CH(OPMB)), 4.59 and 4.87 (2d, 2H, AB, J=11.8 Hz, CH$_2$—Ar), 5.37 (t, 1H, J=7.2 Hz, C=CH—CH$_2$), 6.89 and 7.28 (2d, 4H, J=8.5 Hz, ArH).

$[\alpha]_D^{20}$=−46° (CHCl$_3$, C=1.0)

b. Preparation of (2S,3S,4R,5S)-2-(1,5-dimethylhex-1-enyl)-5-hydroxy-3-methoxy-4-(4-methoxybenzyloxy)cyclohexanone

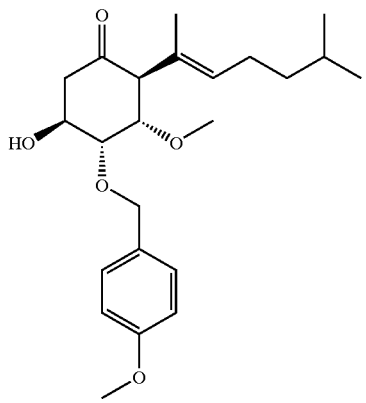

NaBH$_4$ (26.2 mg, 0.70 mmol, 3 eq) is added in two portions to a solution of PhSeSePh (109 mg, 0.35 mmol, 1.5 eq) in ethanol (4 ml). This mixture is stirred for 15 minutes at room temperature and then cooled to 0° C. Glacial acetic acid (6 µl, 0.5 eq) is then added, followed by addition of the epoxide (1R,3S,4S,5R,6S)-3-(1,5-dimethylhex-1-enyl)-4-methoxy-5-(4-methoxybenzyloxy)-7-oxabicyclo[4.1.0]heptan-2-one dissolved in 3 ml of ethanol. After 15 minutes at 0° C., the reaction is quenched by adding EtOAc and then washed with saturated aqueous NaCl solution. This aqueous phase is then extracted three times with EtOAc. The organic phases are combined, dried over sodium sulphate and then concentrated to give a yellow oil, which is then filtered through a bed of silica (Cy and then 1/1 Cy/EtOAc). The residue is then purified on a preparative silica plate: eluent: 75/25 Hex/EtOAc.

74 mg of yellow oil are obtained. Yield 82%.

$R_f$=0.1 7/3Cy/EtOAc.

$^1$H NMR (400 MHz, CDCl$_3$): 0.88 (d, 6H, J=6.4 Hz, (CH$_3$)$_2$), 1.22 (m, 2H, CH$_2$—CH(Me)$_2$), 1.53 (m, 1H, CH(Me)$_2$), 1.58 (s, 3H, CH$_3$—C=C), 2.05 (m, 2H, CH$_2$—C=C), 2.37 (dd, 1H, J=14.8 and 5.3 Hz, CHHequ-CO), 2.82 (dd, 1H, J=14.8 and 3.8 Hz, CHHax-CO), 3.37 (s, 3H, CH$_3$—O), 3.40 (m, 1H, CO—CH), 3.81 (s, 3H, Ar—O—CH$_3$), 3.85 (m, 1H, CH—OMe), 3.96 (m, 1H, CH—OPMB), 4.63 and 4.80 (2d, 2H, AB, J=11.6 Hz, CH$_2$—Ar), 5.13 (t, 1H, J=6.6 Hz, C=CH—CH$_2$), 6.89 and 7.30 (2d, 4H, J=8.3 Hz, ArH).

$^{13}$C NMR (100 MHz, CDCl$_3$): 14.6 (CH$_3$—C=C), 22.5 ((CH$_3$)$_2$), 26.0 (CH$_2$—CH=C), 27.7 (CH—(CH$_3$)$_2$), 38.6 (CH$_2$—CH(CH$_3$)$_2$), 45.0 (CH$_2$—CO), 55.3 (Ar—O—Me), 57.9 (O—Me), 61.9 (CO—CH), 67.9 (CH—OH), 72.8 (CH$_2$—Ar), 75.7 (CH—OPMB), 78.5 (CH—OMe), 113.8 (Ar), 129.5 (Me—C=C)), 130.0 (Ar), 131.0 (CH=C—Me), 131.9 (Ar$^{IV}$), 159.4 (Ar$^{IV}$), 208.0 (C=O).

$[\alpha]_D^{20}$=+34° (CHCl$_3$, C=1.48)

c. Preparation of (2S,3S,4R,5S)-2-(1,5-dimethylhex-1-enyl)-5-(isopropyldimethylsilanyloxy)-3-methoxy-4-(4-methoxybenzyloxy)cyclohexanone

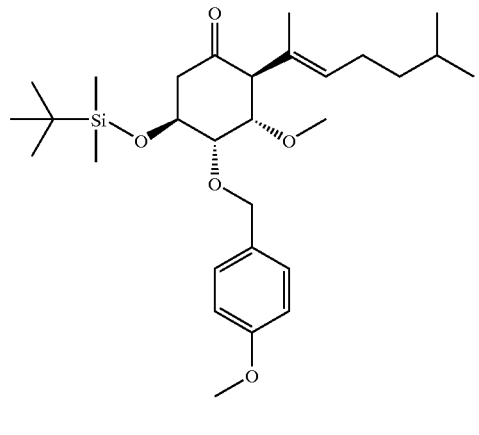

37 mL (237 mmol, 1.5 eq) of isopropyldimethylsilyl chloride are added at room temperature to a solution of 62 mg (158 mmol) of alcohol (2S,3S,4R,5S)-2-(1,5-dimethylhex-1-enyl)-5-hydroxy-3-methoxy-4-(4-methoxybenzyloxy)cyclohexanone in 1 mL of a THF:DMF (1:1) mixture in the presence of 38 mg (316 mmol, 2 eq) of DMAP. The reaction mixture is stirred for one hour at room temperature. The reaction is quenched by adding 1 mL of saturated ammonium chloride solution and then extracted with cyclohexane. The organic phases are combined and dried over anhydrous sodium sulphate, and the residue is then chromatographed on a preparative silica plate: eluent (9/1 Hex/EtOAc).

59 mg of colourless oil are obtained. Yield 76%.

$R_f$=0.4 4/1 Cy/EtOAc.

$^1$H NMR (400 MHz, CDCl$_3$): −0.02 and −0.01 (s, 6H, (Me)$_2$Si), 0.70 (m, 1H, CH—Si), 0.88 (m, 12H, (CH$_3$)$_2$CH—CH$_2$ and (CH$_3$)$_2$CH—Si), 1.24 (m, 2H, CH$_2$—CH(Me)$_2$), 1.56 (m, 4H, CH(Me)$_2$ and Me—C=C), 2.08 (m, 2H, CH$_2$—C=C), 2.24 (ddd, 1H, J=14.7, 3.3 and 0.9 Hz, CHH—C=O), 2.76 (dd, 1H, J=14.7 and 3.4 Hz, CHH—C=O), 3.35 (s, 3H, CH$_3$—O), 3.36 (d, 1H, J=10.7 Hz, C=O—CH), 3.80 (dd, 1H, J=10.7 and 2.8 Hz, CH—OMe), 3.81 (s, 3H, Ar—O—CH$_3$), 3.88 (m, 1H, CH—OPMB), 4.08 (dt, 1H, J=4.5 and 3.3 Hz, CH—O—Si), 4.60 and 4.84 (2d, 2H, AB, J=11.8 Hz, CH$_2$—Ar), 5.19 (t, 1H, J=6.9 Hz, C=CH), 6.90 and 7.30 (2d, 4H, J=8.8 Hz, ArH).

$[\alpha]_D^{20}$=+19° (CHCl$_3$, C=0.65)

d. Preparation of (3R,5S,6R,7S,8S)-8-(1,5-dimethylhex-1-enyl)-7-methoxy-6-(4-methoxybenzyloxy)-1-oxaspiro[2,5]oct-5-yloxy]isopropyldimethylsilane

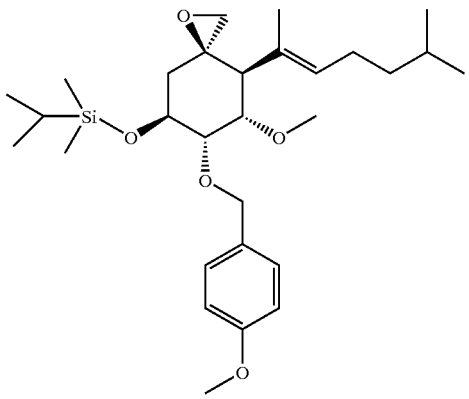

375 μL (600 μmol, 5.0 eq) of a 1.6 M solution of BuLi in hexane are added to a solution, at −78° C., of 59 mg (120 μmol, 1.0 eq) of (2S,3S,4R,5S)-2-(1,5-dimethylhex-1-enyl)-5-(isopropydimethylsilanyloxy)-3-methoxy-4-(4-methoxybenzyloxy)cyclohexanone and 68 μL (835 μmol, 5.0 eq) of diiodomethane in 1 mL of THF. The solution is stirred for one hour at −78° C. and then for 1.5 hours at room temperature. The reaction is quenched by adding 1 mL of ammonium chloride solution and then extracted with ethyl acetate. The organic phases are combined and then dried over anhydrous sodium sulphate. After evaporating off the solvents, the residue is chromatographed on a preparative silica plate: eluent (9/1 Cy/EtOAc).

22 mg of colourless oil are obtained. Yield 36%

$R_f$=0.35 4/1 Cy/EtOAc.

$^1$H NMR (400 MHz, CDCl$_3$): 0.00 and 0.01 (s, 6H, (Me)$_2$Si), 0.76 (m, 1H, CH—Si), 0.86 and 0.88 (2d, 6H, J=6.6 Hz, (Me)$_2$CH), 0.93 and 0.94 (2d, 6H, (CH$_3$)$_2$CH—Si), 1.20 (m, 2H, CH$_2$—CH(Me)$_2$), 1.35 (dd, 1H, J=13.8 and 4.7 Hz, CHH—CH(OSi)), 1.54 (s, 3H, Me—C=C), 1.96 (m, 2H, CH$_2$—C=C), 2.15 (dd, 1H, J=13.8, 2.5 Hz, CHH—CH(OSi)), 2.24 and 2.49 (2d, AB, 2H, J=5.3 Hz, CH$_2$(spiro-epoxide)), 2.79 (d, 1H, J=9.8 Hz, CH(OMe)), 3.34 (s, 3H, CH$_3$—O), 3.74 (dd, 1H, J=5.0 and 2.3 Hz, CH(OPMB)), 3.81 (s, 3H, Ar—O—CH$_3$), 3.84 (dd, 1H, J=9.8 and 2.5 Hz, CH(OMe)), 4.01 (m, 1H, CH(OSi)), 4.57 and 4.70 (2d, 2H, AB, J=12.1 Hz, CH$_2$—Ar), 5.21 (t, 1H, J=6.9 Hz, CH=C), 6.87 and 7.29 (2d, 4H, J=8.8 Hz, ArH).

e. Preparation of (3R,4S,5S,6R,7S)-4-(1,5-dimethylhex-1-enyl)-7-(isopropyldimethylsilanyloxy)-5-methoxy-1-oxaspiro[2,5]octan-6-ol

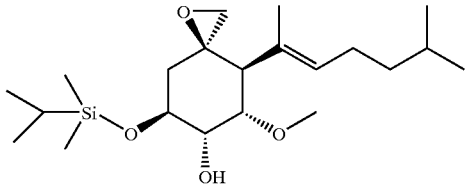

7 mg (31 μmol, 1.2 eq) of DDQ are added to a solution of 13 mg (26 μmol, 1 eq) of (3R,5S,6R,7S,8S)-8-(1,5-dimethylhex-1-enyl)-7-methoxy-6-(4-methoxybenzyloxy)-1-oxaspiro[2,5]oct-5-yloxy]isopropyldimethylsilane in 1 mL of CH$_2$Cl$_2$ in the presence of 25 μL of water. The reaction mixture is stirred for two hours at room temperature. The reaction is quenched by adding 0.5 mL of saturated sodium hydrogen carbonate solution and then extracted with ethyl acetate. The organic phases are combined, dried over sodium sulphate and then concentrated under reduced pressure. The residue is then chromatographed on preparative silica plates (eluent CH$_2$Cl$_2$).

8.0 mg of colourless oil are obtained. Yield 80%.

$^1$H NMR (400 MHz, CDCl$_3$): 0.07 (s, 3H, Si—Me), 0.08 (s, 3H, Si—Me), 0.82 (m, 1H, (Me)$_2$CH—Si), 0.87 and 0.88 (d, 6H, J=6.4 Hz, (CH$_3$)$_2$), 0.97 (d, 6H, J=6.8 Hz, (Me)$_2$CH—Si), 1.23 (m, 2H, CH$_2$—CH(Me)$_2$), 1.46 (dd, 1H, J=14.1, 5.0 Hz, CHH—CH(OSi)), 1.53 (m, 1H, CH(Me)$_2$), 1.62 (s, 3H, CH$_3$C=C), 2.00 (m, 2H, CH$_2$—CH=C), 2.10 (dd, 1H, J=14.1 and 3.5 Hz, CHH—CH(OSi)), 2.30 and 2.49 (2d, AB, J=4.5 Hz, CH$_2$(spiro-epoxide)), 2.32 (d, 1H, J=2.0 Hz, OH), 2.62 (d, 1H, J=9.0 Hz, CH(OMe)—CH—C(spiro-epoxide)), 3.39 (s, 3H, CH$_3$—O), 3.86 (dd, J=9.0 and 2.8 Hz, 1H, CH—O—Me), 3.97 (m, 1H, CH—OH), 4.09 (m, 1H, CH(OSi)), 5.27 (t, 1H, J=7.8 Hz, C=CH).

f. Preparation of (3R,4S,5S,6R,7S)-4-(1,5-dimethylhex-1-enyl)-7-hydroxy-5-methoxy-1-oxaspiro[2,5]oct-6-yl 4-methoxycinnamate

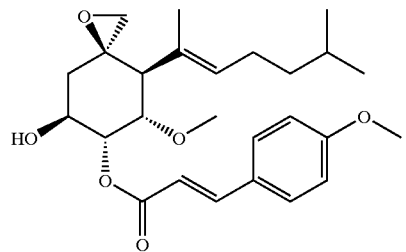

0.88 and 0.89 (d, 6H, J=6.4 Hz, (CH$_3$)$_2$), 1.23 (m, 2H, CH$_2$—CH(Me)$_2$), 1.48–1.61 (m, 2H, CHHax-CHOH and CH(Me)$_2$), 1.61 (s, 3H, CH$_3$—C=C), 2.05 (m, 2H, CH$_2$—CH=C), 2.37 (dd, J=14.6, 3.3 Hz, 1H, CHHequ-CHOH), 2.47 and 2.66 (2d, AB, J=4.8 Hz, CH$_2$(spiro-epoxide)), 2.57 (d, 1H, J=6.4 Hz, CHOH), 2.84 (d, 1H, J=10.4 Hz, C(spiro-epoxide)-CH—CH(OMe)), 3.39 (s, 3H, CH$_3$—O), 3.85 (s, 3H, Ar—O—CH$_3$), 4.02 (dd, 1H, J=10.0, 2.8 Hz, CH—OMe), 4.20 (m, 1H, CHOH), 5.33 (t, J=7.2 Hz, 1H, C=CH), 5.62 (m, 1H, CH—COO), 6.35 (d, J=16.0 Hz, 1H, Ar—CH=CH—COO), 6.91 and 7.48 (2d, 4H, J=8.8 Hz, ArH), 7.67 (d, J=16.0 Hz, 1H, Ar—CH=CH—COO).

Compound Z:

0.88 and 0.89 (d, 6H, J=6.4 Hz, (CH$_3$)$_2$), 1.23 (m, 2H, CH$_2$—CH(Me)$_2$), 1.48–1.61 (m, 2H, CHHax-CHOH and CH(Me)$_2$), 1.59 (s, 3H, CH$_3$—C=C), 2.05 (m, 2H, CH$_2$—CH=C), 2.22 (dd, J=14.6, 3.3 Hz, 1H, CHHequ-CHOH), 2.42 and 2.62 (2d, AB, J=4.8 Hz, CH$_2$(spiro-epoxide)), 2.55 (d, 1H, J=6.4 Hz, CHOH), 2.75 (d, 1H, J=10.4 Hz, C(spiro-epoxide)-CH—CH(OMe)), 3.38 (s, 3H, CH$_3$—O), 3.83 (s, 3H, Ar—O—CH$_3$), 3.98 (dd, 1H, J=10.0, 2.8 Hz, CH—OMe), 4.00 (m, 1H, CHOH), 5.28 (t, J=7.2 Hz, 1H, C=CH), 5.59 (m, 1H, CH—COO), 5.88 (d, J=12.4 Hz, 1H, Ar—CH=CH—COO), 6.88 and 7.68 (2d, 4H, J=8.8 Hz, ArH), 6.90 (d, J=12.4 Hz, 1H, Ar—CH=CH—COO).

Example 11

Preparation of (3R,4S,5S,6R,8R)-4-(1,5-dimethylhex-1-enyl)-5-methoxy-8-methyl-1-oxaspiro[2,5]oct-6-yl 4-methoxycinnamate

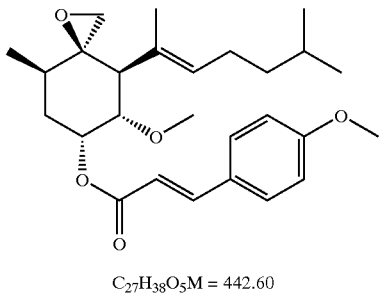

C$_{27}$H$_{38}$O$_5$M = 442.60 a. Preparation of (4R,5S,6S)-6-(1,5-dimethylhex-1-enyl)-2-hydroxymethyl-5-methoxy-4-(4-methoxybenzyloxy)cyclohex-2-enone

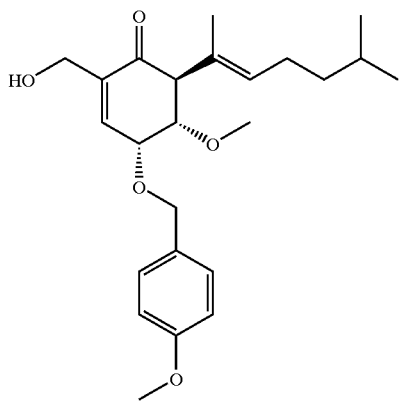

130 µl (0.53 mmol, 0.85 eq) of tri-n-butylphosphine, followed by 130 µl (1.62 mmol, 2.6 eq) of aqueous 40% formaldehyde solution, are added to a solution of 230 mg (0.618 mmol, 1.0 eq) of (4R,5S,6S)-5-methoxy-4-p-methoxybenzyloxy-6-(1,5-dimethylhex-1-enyl)cyclohex-2-enone in 5 mL of THF. The reaction mixture is stirred overnight at room temperature and then partitioned between water and ethyl acetate. After separation of the phases, the aqueous phase is extracted with ethyl acetate. The organic phases are combined, dried over sodium sulphate and then concentrated to give a colourless oil which is then chromatographed on silica gel (eluent: 7/3 CyHex/EtOAc).

200.0 mg of colourless oil are obtained. Yield 80%

R$_f$=0.15 7/3 Cy/EtOAc.

$^1$H NMR (400 MHz, CDCl$_3$): 0.85 (d, 6H, J=6.4 Hz, (CH$_3$)$_2$), 1.15 (m, 2H, CH$_2$—CH(Me)$_2$), 1.50 (m, 1H, CH(Me)$_2$), 1.56 (s, 3H, CH$_3$—C=C), 2.00 (m, 2H, CH$_2$—CH=C), 3.40 (s, 3H, CH$_3$—O), 3.45 (d, 1H, J=6.4 Hz, CH—C=O), 3.74 (m, 1H, CH—OMe), 3.80 (s, 3H, Ar—O—CH$_3$), 4.18 (d, 1H, J=14.4 Hz, CHH—OH), 4.36 (m, 2H, CH—OPMB and CHH—OH), 4.64 and 4.68 (2d, 2H, AB, J=11.6 Hz, CH$_2$—Ar), 5.12 (t, 1H, J=7.0 Hz, C=CH), 6.75 (m, 1H, C=CH—CH(OPMB)), 6.88 and 7.28 (2d, 4H, J=8.8 Hz, ArH).

$^{13}$C NMR (100 MHz, CDCl$_3$): 15.2 (CH$_3$—C=C), 22.5 ((CH$_3$)$_2$—CH), 26.0 (CH$_2$—HC=C), 27.7 (CH—(CH$_3$)$_2$), 38.4 (CH$_2$—CH(CH$_3$)$_2$), 55.3 (CH$_3$—O), 57.7 (CH—C=O), 58.8 (CH$_3$—O), 61.1 (CH$_2$OH), 69.7 (CH(OPMB)), 71.6 (CH$_2$—Ar), 80.1 (CH—OMe), 113.9 (Ar), 128.9 (Me—C=CH), 129.5 (Ar), 129.9 (Ar$^{IV}$), 130.4 (CH=C—Me), 139.6 (C=C—CH$_2$OH), 140.6 (C=C—CH$_2$OH), 159.5 (Ar$^{IV}$), 199.5 (C=O).

[α]$_D^{20}$=−116° (CHCl$_3$, C=1.4)

b. Preparation of (4R,5S,6S)-2-(tert-butyldimethylsilanyloxymethyl)-6-(1,5-dimethythex-1-enyl)-5-methoxy-4-(4-methoxybenzyloxy)cyclohex-2-enone

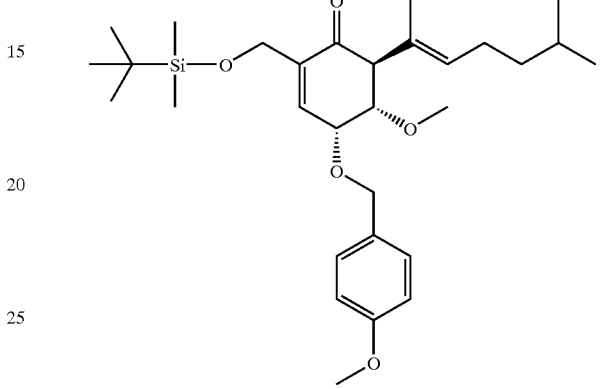

80 mg (530 µmol, 1.1 eq) of TBSCl are added at room temperature to a solution of 195 mg (485 µmol, 1.0 eq) of alcohol (4R,5S,6S)-6-(1,5-dimethylhex-1-enyl)-2-hydroxymethyl-5-methoxy-4-(4-methoxybenzyloxy)cyclohex-2-enone in 3 mL of THF in the presence of 89 mg (728 µmol, 1.5 eq) of DMAP. The reaction mixture is stirred for four hours at room temperature. The reaction is quenched by adding 3 mL of saturated ammonium chloride solution and then extracted with cyclohexane. The organic phases are combined and dried over anhydrous sodium sulphate, and the residue is then chromatographed on silica gel: eluent (9/1 Cy/EtOAc).

170 mg of colourless oil are obtained. Yield 68%.

R$_f$=0.2 9/1 Cy/EtOAc.

$^1$H NMR (400 MHz, CDCl$_3$): 0.06 and 0.08 (2s, 6H, (CH$_3$)$_2$Si), 0.86 (d, 6H, J=6.8 Hz, (CH$_3$)$_2$CH), 0.92 (s, 9H, tBu-Si), 1.19 (q, 2H, J=7.6 Hz, CH$_2$—CH(Me)$_2$), 1.52 (m, 1H, CH(Me)$_2$), 1.56 (s, 3H, CH$_3$—C=C), 2.03 (m, 2H, CH$_2$—CH=C), 3.40 (s, 3H, CH$_3$—O), 3.46 (d, 1H, J=6.4 Hz, CH—C=O), 3.71 (m, 1H, CH—OMe), 3.81 (s, 3H, Ar—O—CH$_3$), 4.34 (m, 3H, CH$_2$(OTBS) and CH(OPMB)), 4.66 (s, 2H, CH$_2$—Ar), 5.13 (t, 1H, J=7.0 Hz, C=CH—CH$_2$), 6.84 (bs, 1H, C=CH—CH(OPMB)), 6.88 and 7.30 (2d, 4H, J=8.0 Hz, ArH).

$^{13}$C NMR (100 MHz, CDCl$_3$): −4.6 ((CH$_3$)$_2$Si), 15.0 (CH$_3$—C=C), 18.3 (Si—C(Me)$_3$), 22.5, 25.9 (CH$_3$)$_3$C—Si and CH$_2$—CH=C), 27.6 (CH—(CH$_3$)$_2$), 38.4 (CH$_2$—CH—CH$_3$)$_2$), 55.2, 57.5, 58.9, 59.8, 70.2 (CH(OPMB)), 71.5 (CH$_2$—Ar), 80.1 (CH—OMe), 113.9 (Ar), 129.0 (Me—C=C), 129.5 (Ar), 130.3 (Ar$^{IV}$), 130.5 (CH=C—Me), 138.5 (C=C—CH$_2$OSi), 140.2 (C=C—CH$_2$OSi), 159.4 (Ar$^{IV}$), 198.2 (C=O).

[α]$_D^{20}$=−74° (CHCl$_3$, C=0.9)

c. Preparation of (2S,3S,4R)-2-(1,5-dimethylhex-1-enyl)-3-methoxy-4-(4-methoxybenzyloxy)-6-methylenecyclohexanone

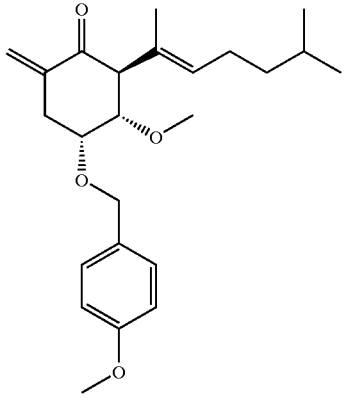

Et$_3$SiH (1.5 mL) and then the Wilkinson catalyst RhCl(PPh$_3$)$_3$ (6 mg, 7 μmol, 0.03 eq) are successively added to a solution of (4R,5S,6S)-2-(tert-butyldimethylsilanyloxymethyl)-6-(1,5-dimethylhex-1-enyl)-5-methoxy-4-(4-methoxybenzyloxy)cyclohex-2-enone (135 mg, 261 μmol) in toluene (1.5 mL). The solution is then heated at 65° C. for four hours. The solvent is then evaporated off and the residue is filtered through silica gel (eluent Cy and then 9/1 Cy/EtOAc). 176 mg of an impure oil are obtained. This oil is dissolved in a 1/1 THF/H$_2$O mixture and a 1M TFA solution (260 μl, 1 eq) is then added. The mixture is stirred for 1 hour 30 minutes at room temperature and the reaction is then quenched with water. The mixture is then extracted with CH$_2$Cl$_2$. The organic phases are combined and then dried over anhydrous sodium sulphate. After evaporating off the solvents, the residue is chromatographed on silica gel: eluent (9/1 Cy/EtOAc).

70 mg of colourless oil are obtained. Yield 70%

R$_f$=0.15 4/1 Cy/EtOAc.

$^1$H NMR (400 MHz, CDCl$_3$): 0.87 (d, 6H, J=6.8 Hz, (CH$_3$)$_2$CH), 1.23 (m, 2H, CH$_2$—CH(Me)$_2$), 1.55 (m, 1H, CH(Me)$_2$), 1.57 (s, 3H, CH$_3$—C=C), 2.03 (m, 2H, CH$_2$—CH=C), 2.53 (dd, 1H, J=16 Hz, 2.8 Hz, CHHeq-CH(OPMB)), 2.92 (dd, 1H, J=16 Hz, 6.4 Hz, ChaxH—CH(OPMB)), 3.38 (s, 3H, CH$_3$—O), 3.42 (d, 1H, J=8.6 Hz, CH—C=O), 3.60 (dd, 1H, J=8.6, 1.5 Hz, CH—OMe), 3.81 (s, 3H, Ar—O—Me), 4.08 (m, 1H, CH(OPMB)), 4.60 (s, 2H, CH$_2$—Ar), 5.17 (t, 1H, J=7 Hz, C=CH—CH$_2$), 5.21 (d, 1H, J=1.5 Hz, C=CHH), 5.98 (s, 1H, C=CHH), 6.87 and 7.27 (2d, 4H, J=8.8 Hz, ArH).

$^{13}$C NMR (100 MHz, CDCl$_3$): 14.8, 22.5, 26.0, 27.6, 32.5, 55.3, 57.6, 60.9, 70.7, 71.1, 80.7, 113.8, 113.9, 123.2, 129.2, 130.0, 130.5, 131.2, 141.2, 159.2, 200.0 (C=O).

$[\alpha]_D^{20}$=−5.6° (CHCl$_3$, C=1.8)

d. Preparation of (2S,3S,4R,6R)-2-(1,5-dimethylhex-1-enyl)-3-methoxy-4-(4-methoxybenzyloxy)-6-methylcyclohexanone

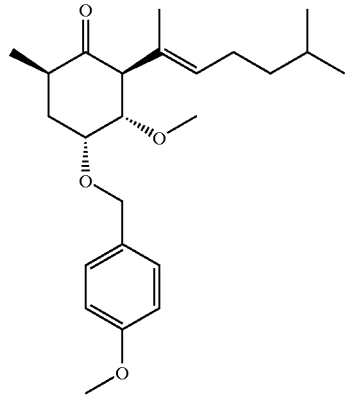

10 drops of a Raney nickel suspension are added to a solution of 70 mg (106 μmol) of (2S,3S,4R)-2-(1,5-dimethylhex-1-enyl)-3-methoxy-4-(4-methoxybenzyloxy)-6-methylenecyclohexanone in 1 mL of THF at 0° C. The medium is stirred vigorously for two hours at 0° C. The reaction is filtered through a bed of Celite 545 with diethyl ether and then evaporated. The residue is chromatographed on a preparative silica plate: eluent: 9/1 Cy/EtOAc.

11 mg of (2S,3S,4R,6R)-2-(1,5-dimethylhex-1-enyl)-3-methoxy-4-(4-methoxybenzyloxy)-6-methylcyclohexanone (16% yield) and 25 mg of the diastereoisomer (2S,3S,4R,6S)-2-(1,5-dimethylhex-1-enyl)-3-methoxy-4-(4-methoxybenzyloxy)-6-methylcyclohexanone (36% yield) are obtained.

R$_f$=0.30 4/1 Cy/EtOAc.

$^1$H NMR (400 MHz, CDCl$_3$): 0.88 (d, 6H, J=6.4 Hz, (CH$_3$)$_2$CH), 0.98 (d, 3H, J=6.8 Hz, Me—CH), 1.17–1.28 (m, 3H, CH$_2$—CH(Me) and CHHax-CH(OPMB)), 1.55 (m, 1H, CH(Me)$_2$), 1.59 (s, 3H, CH$_3$—C=C), 2.08 (m, 2H, CH$_2$—CH=C), 2.20 (ddd, 1H, J=14.4, 5.8, 4.0 Hz, CHHeq-CH(OPMB)), 2.75 (d quint, 1H, J=13, 6.6 Hz, CH(Me)), 3.30 (s, 3H, CH$_3$—O), 3.35 (dd, 1H, J=11.9, 2.5 Hz, CH—OMe), 3.57 (d, 1H, J=11.9 Hz, CH—C=O), 3.82 (s, 3H, Ar—O—Me), 4.11 (m, 1H, CH(OPMB)), 4.63 (2d, AB, 2H, J=11.6 Hz, CH$_2$—Ar), 5.18 (t, 1H, J=6.8 Hz, C=CH—CH$_2$), 6.88 and 7.34 (2d, 4H, J=8.4 Hz, ArH).

$^{13}$C NMR (100 MHz, CDCl$_3$): 13.9, 22.6, 25.9, 27.7, 29.7, 33.9, 38.5, 38.7, 55.3, 57.2, 61.8, 70.4, 71.4, 82.7, 117.1, 129.3, 129.4, 130.7, 130.8, 159.2, 209.7 (C=O).

$[\alpha]_D^{20}$=−16° (CHCl$_3$, C=0.5)

e. Preparation of (3R,4S,5S,6R,8R)-4-(1,5-dimethylhex-1-enyl)-5-methoxy-6-(4-methoxybenzyloxy)-8-methyl-1-oxaspiro[2,5]octane

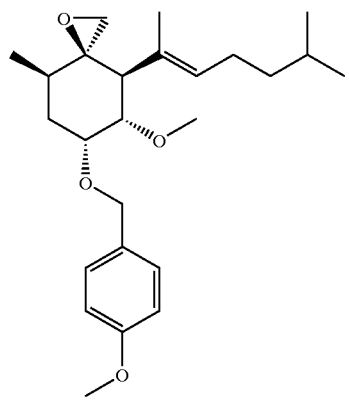

160 μL (250 μmol, 5.0 eq) of a 1.6 M solution of BuLi in hexane are added to a solution, at −78° C., of 20 mg (51 μmol, 1.0 eq) of (2S,3S,4R,6R)-2-(1,5-dimethylhex-1-enyl)-3-methoxy-4-(4-methoxybenzyloxy)-6-methylcyclohexanone and 20 μL (250 μmol, 5.0 eq) of diiodomethane in 0.3 mL of THF. The solution is stirred for 45 minutes at −78° C. and then for 1.5 hours at room temperature. The reaction is quenched by adding 1 mL of saturated ammonium chloride solution and then extracted with ethyl acetate. The organic phases are combined and then dried over anhydrous sodium sulphate. After evaporating off the solvents, the residue is chromatographed on a preparative silica plate: eluent (9/1 Cy/EtOAc).

11 mg of colourless oil are obtained. Yield 54%

$R_f$=0.5 4/1 Cy/EtOAc.

$^1$H NMR (400 MHz, CDCl$_3$): 0.67 (d, 3H, J=6.8 Hz, Me—CH), 0.87 and 0.88 (2d, 6H, J=6.4 Hz, (CH$_3$)$_2$CH), 1.22 (m, 3H, CH$_2$—CH(Me)$_2$), 1.37 (td, 1H, J=13.0 and 2.0 Hz, CHHax-CH(OPMB)), 1.52 (m, 1H, CH(Me)$_2$), 1.54 (s, 3H, CH$_3$—C=C), 1.89 (dt, J=14.0 and 3.8 Hz, CHHeq-CH (OPMB), 2.01 (m, 2H, CH$_2$—CH=C), 2.34 (dtd, 1H, J=13.0, 6.8, 3.8 Hz, CH(Me)), 2.47 and 2.61 (2d, AB, 2H, J=4.8 Hz, CH$_2$ spiro-epoxide), 3.01 (d, 1H, J=11.6 Hz, CH—CHOH—CH(OPMB)), 3.29 (s, 3H, CH$_3$—O), 3.46 (dd, 1H, J=11.6, 2.4 Hz, CH—OMe), 3.81 (s, 3H, Ar—O—Me), 4.06 (bs, 1H, CH(OPMB)), 4.61 and 4.67 (2d, AB, 2H, J=12.0 Hz, CH$_2$—Ar), 5.21 (t, 1H, J=6.6 Hz, C=CH—CH$_2$), 6.87 and 7.32 (2d, 4H, J=8.8 Hz, A $^{13}$C NMR (100 MHz, CDCl$_3$): 13.8 ((CH$_3$—C=C) and Me—CH), 22.5 and 22.6 ((CH$_3$)$_2$), 25.8 (CH$_2$—HC=C), 27.7 (CH—(CH$_3$)$_2$), 28.4 (CH—CH$_3$), 34.4 (CH$_2$—CH (CH$_3$)), 38.9 (8 (CH$_2$—CH(CH$_3$)$_2$), 47.9 (CH$_2$-spiro-epoxide), 49.8 (C—CHOMe—CH(OPMB)), 55.3 (Ar—O—Me), 56.6 (OMe), 70.0 (CH—OPMB and CH$_2$—Ar), 81.1 (CH—OMe), 114.8 (Ar), 129.2 (Ar), 130.6 (C=CH and C=CH), 131.3 (Ar$^{IV}$), 159.1 (Ar$^{IV}$).

[α$_D^{20}$=−53° (CHCl$_3$, C=0.55)

f. Preparation of (3R,4S,5S,6R,8R)-4-(1,5-dimethylhex-1-enyl)-5-methoxy-6-methyl-1-oxaspiro[2,5]octan-6-ol

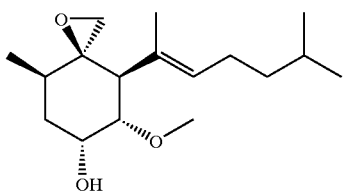

8 mg (33 μmol, 1.2 eq) of DDQ are added to a solution of 11 mg (27 μmol, 1 eq) of (3R,4S,5S,6R,8R)-4-(1,5-dimethylhex-1-enyl)-5-methoxy-6-(4-methoxybenzyloxy)-8-methyl-1-oxaspiro[2,5]octane in 0.5 mL of CH$_2$Cl$_2$ in the presence of 30 μL of water.

The reaction mixture is stirred for one hour at room temperature. The reaction is quenched by adding 0.5 mL of saturated sodium hydrogen carbonate solution and then extracted with ethyl acetate. The organic phases are combined, dried over sodium sulphate and then concentrated under reduced pressure. The residue is then chromatographed on preparative silica plates (eluent: 9/1 Cy/EtOAc).

6.0 mg of colourless oil are obtained. Yield 77%.

$R_f$=0.2 (4/1 Cy/EtOAc).

$^1$H NMR (400 MHz, CDCl$_3$): 0.69 (d, 3H, J=6.8 Hz, Me—CH), 0.87 and 0.89 (d, 6H, J=6.4 Hz, (CH$_3$)$_2$), 1.22 (m, 2H, CH$_2$—CH(Me)$_2$), 1.52 (m, 1H, CH(Me)$_2$), 1.57 (s, 3H, CH$_3$C=C), 1.93 (dt, 1H, J=14.1 and 3.7 Hz, CHH—CHOH), 2.04 (m, 2H, CH$_2$—CH=C), 2.37 (m, 2H, Me—CH and CHH—CHOH), 2.51 and 2.64 (2d, AB, J=4.5 Hz, CH$_2$-spiro-epoxide), 2.80 (d, 1H, J=11.3, CH(OMe)-CH—C(spiro-epoxide)), 3.38 (s, 3H, CH$_3$—O), 3.49 (dd, J=11.3 and 2.8 Hz, 1H, CH—O—Me), 4.33 (m, 1H, CH—OH), 5.22 (t, 1H, J=6.9 Hz, C=CH).

g. Preparation of (3R,4S,5S,6R,8R)-4-(1,5-dimethylhex-1-enyl)-5-methoxy-8-methyl-1-oxaspiro[2,5]oct-6-yl 4-methoxycinnamate

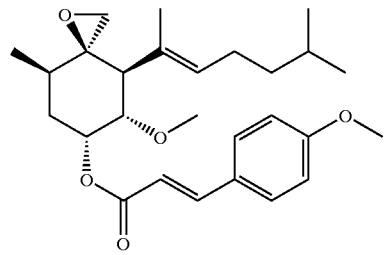

44 mg (250 μmol, 10 eq) of p-methoxycinnamic acid, followed immediately by 30 mg (250 μmol, 10 eq) of DMAP and 51 mg (250 μmol, 10 eq) of DCC, are added to a solution of 6 mg (0.087 mmol, 1.0 eq) of (3R,4S,5S,6R,8R)-4-(1,5-dimethylhex-1-enyl)-5-methoxy-8-methyl-1-oxaspiro[2,5] octan-6-ol in 1 mL of dichloromethane. The reaction mixture is stirred overnight at room temperature. The solvents are evaporated off and the residue is filtered through a patch of silica (1 cm): eluent (7/3 Cy/EtOAc). The residue is then chromatographed on a preparative silica plate: eluent (9/1 n-hex/EtOAc).

8 mg of colourless oil are obtained. Yield 90%.

$R_f$=0.4 (4/1 Cy/EtOAc).

$^1$H NMR (400 MHz, CDCl$_3$): 0.71 (d, 3H, J=6.8 Hz, CH$_3$—CH), 0.88 and 0.89 (d, 6H, J=6.6 Hz, (CH$_3$)$_2$), 1.26 (m, 2H, CH$_2$—CH(Me)$_2$), 1.53 (m, 1H, CH(Me)$_2$), 1.57 (s, 3H, CH$_3$—C=C), 1.64 (td, 1H, J=13.7, 2.0 Hz, CHH—CH (Me)), 1.95 (dt, 1H, J=14.6, 3.8 Hz, CHHax-CH(Me)—CH (OPMB)), 2.05 (m, 2H, CH$_2$—CH=C), 2.32 (m, 1H, Me—CH), 2.44 and 2.60 (2d, J=5.0 Hz, CH$_2$-spiro-epoxide), 2.70 (d, 1H, J=8.3, CH(OMe)—CH—C=C), 3.36 (s, 3H, CH$_3$—O), 3.83 (s, 3H, Ar—O—CH$_3$), 3.87 (m, 1H, CH—OMe), 5.25 (m, 1H, CH—COO), 5.40 (t, J=6.8 Hz, 1H, C=CH), 6.38 (d, J=16 Hz, 1H, Ar—CH=C), 6.91 and 7.48 (2d, 4H, J=8.8 Hz, ArH), 7.66 (d, J=16 Hz, 1H, COO—CH=C).

$^{13}$C NMR (100 MHz, CDCl$_3$): 14.8 (CH$_3$—C=C), 17.9 (CH$_3$—CH), 22.5 ((CH$_3$)$_2$), 25.9 (CH$_2$13 CH=C), 27.8 (CH—(CH$_3$)$_2$), 32.0 (CH—CH$_3$), 35.5 (CH$_2$—CH(CH$_3$)), 38.8 (CH$_2$—CH—(CH$_3$)$_2$), 50.0 (CH—CH(OMe)—CH (OPMB)), 50.7 (CH$_2$-spiro-epoxide), 55.3 (Ar—O—CH$_3$), 57.5 (CH$_3$—O), 58.6 (C$^{IV}$-spiro-epoxide), 73.0 (CH—COO), 77.3 (CH—OMe), 114.3 (Ar), 115.8 (C=CH—Ar), 127.2 (MeC=CH), 130.3 (MeC=CH), 130.5 (Ar$^{IV}$), 129.8 (Ar), 144.6 (COO—CH=C), 161.4 (Ar$^{IV}$), 166.9 (COO).

[α]$_D^{20}$=−49° (CHCl$_3$, C=0.9)

Example 12

Formulation Examples

1) ORAL ROUTE
(a) 0.2 g tablet

| | |
|---|---|
| Compound of Example 1 | 0.001 g |
| Starch | 0.114 g |
| Dicalcium phosphate | 0.020 g |

-continued

| | |
|---|---|
| Silica | 0.020 g |
| Lactose | 0.030 g |
| Talc | 0.010 g |
| Magnesium stearate | 0.005 g |
| (b) Drinkable suspension in 5 ml ampules | |
| | |
| Compound of Example 3 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavouring qs | |
| Purified water qs | 5 ml |
| (c) 0.8 g tablet | |
| | |
| Compound of Example 10 | 0.250 g |
| Compound of Example 8 | 0.250 g |
| Pregelatinized starch | 0.100 g |
| Microcristalline cellulose | 0.115 g |
| Lactose | 0.075 g |
| Magnesium stearate | 0.010 g |
| (d) Drinkable suspension in 10 ml ampules | |
| | |
| Compound of Example 7 | 0.05 g |
| Glycerol | 1.000 g |
| 70% sorbitol | 1.000 g |
| Sodium saccharinate | 0.010 g |
| Methyl para-hydroxybenzoate | 0.080 g |
| Flavouring qs | |
| Purified water qs | 10 ml |
| 2) TOPICAL ROUTE | |
| (a) Ointment | |
| | |
| Compound of Example 9 | 0.020 g |
| Isopropyl myristate | 81.700 g |
| Fluid liquid petroleum jelly | 9.100 g |
| Silica ("Aerosil 200" sold by Degussa) | 9.180 g |
| (b) Ointment | |
| | |
| Compound of Example 4 | 0.150 g |
| Compound of Example 6 | 0.150 g |
| White petroleum jelly codex | 100 g |
| (c) Nonionic water-in-oil cream | |
| | |
| Compound of Example 5 | 0.100 g |
| Mixture of emulsive lanolin alcohols, waxes and oils ("anhydrous Eucerin" sold by BDF) | 39.900 g |
| Methyl para-hydroxybenzoate | 0.075 g |
| Propyl para-hydroxybenzoate | 0.075 g |
| Sterile demineralized water qs | 100 g |
| (d) Lotion | |
| | |
| Compound of Example 6 | 0.100 g |
| Polyethylene glycol (PEG 400) | 69.900 g |
| 95% ethanol | 30.000 g |
| (e) Hydrophobic ointment | |
| | |
| Compound of Example 9 | 0.200 g |
| Compound of Example 13 | 0.100 g |
| Isopropyl myristate | 36.400 g |
| Silicone oil ("Rhodorsil 47 V 300" sold by Rhône-Poulenc) | 36.400 g |
| Beeswax | 13.600 g |
| Silicone oil ("Abil 300 000 cSt" sold by Goldschmidt) | 100 g |
| (f) Nonionic oil-in-water cream | |
| | |
| Compound of Example 11 | 0.500 g |
| Cetyl alcohol | 4.000 g |
| Glyceryl monostearate | 2.500 g |
| PEG 50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | 100 g |

3) Intralesional Route
 (a) The following composition is prepared:

| | |
|---|---|
| Compound of Example 6 | 0.002 g |
| Ethyl oleate qs | 10 g |

In the treatment of malignant melanoma, the composition is injected into an adult person at a frequency of 1 to 7 times a week for 1 to 12 months.
 (b) The following composition is prepared:

| | |
|---|---|
| Compound of Example 10 | 0.050 g |
| Olive oil qs | 2 g |

In the treatment of basocellular carcinoma, the composition is injected into an adult person at a frequency of 1 to 7 times a week for 1 to 12 months.
 (c) The following composition is prepared:

| | |
|---|---|
| Compound of Example 12 | 0.1 mg |
| Sesame oil qs | 2 g |

In the treatment of spinocellular carcinoma, the composition is injected into an adult person at a frequency of 1 to 7 times a week for 1 to 12 months.
 (d) The following composition is prepared:

| | |
|---|---|
| Compound of Example 2 | 0.001 mg |
| Methyl benzoate qs | 10 g |

In the treatment of colon carcinoma, the composition is injected into an adult person at a frequency of 1 to 7 times a week for 1 to 12 months.
4) Intravenous Route
 (a) The following injectable composition is prepared:

| | |
|---|---|
| Compound of Example 2 | 0.001% |
| 1.4% sodium bicarbonate solution | 2% |
| Ethanol | 1% |
| 0.9% NaCl solution qs | 100 |

Example 13

Example of a Test to Evaluate the Biological Activity of the Compounds of the Invention a) Measurement of the Inhibition of Human MetAP-2

Recombinant MetAP-2 is obtained and purified according to the method described by Li and Chang (Li, X.; Chang, Y-H. *Biochem. Biophys. Res. Comm.* 1996, 227, 152).

The tests are carried out in buffer A (Hepes buffer, 10 mM, pH 7.4, 0.5 mM $CoCl_2$ containing 10% glycerol) using the peptide Met-Ala-Ser as substrate (Km=0.7 mM).

a. The enzymatic activity is measured as follows: the substrate solution is added to a suitable amount of enzyme such that the final concentration is 1 mM, and the mixture is incubated at 37° C. for 10–30 minutes. The reaction is quenched by adding 100 mM EDTA solution or by heating in a boiling water bath for two minutes.

b. The N-terminal methionine released is quantified by measuring the absorbance at 450 nm ($A_{450}$) by incubating for 30–60 minutes at 37° C. with the following coloured reagent: buffer B (Hepes buffer, 10 mM, pH 7.4) (Ben-Bassat A.; Bauer K.: Chang S. Y. et al., *J. Bacteriol.* 1987, 169, 751–757), containing 70 µg/mL of amino acid oxidase, 10 µg/mL of horseradish peroxidase and 1 mM of o-dianisidine. The activities are expressed as mmol of methionine produced, using the conversion factor of 1 mmol of methionine/mL=$8.6 A_{450}$ Determination of the $IC_{50}$ The $IC_{50}$ values are determined by incubating the enzyme and its substrate (using the experimental conditions described above) with increasing concentrations of inhibitor.

The control is 5-methoxy-4-[2-methyl-3-(3-methylbut-2-enyl)oxiranyl]-1-oxaspiro[2.5]octan-6-yl 4-methoxycinnamate described in the publication by Han et al., *Bioorganic & Medicinal Chemistry Letters*, 2000, 10, 39–43.

| Compound | $IC_{50}$ (nM) | Standard deviation (nM) |
|---|---|---|
| Fumagillin | 10 | 5 |
| Control | 35 | 10 |
| Example 2 | 15 | 1 |

These results show that the compounds according to the invention have strong inhibitory activity on the enzyme MetAP-2, comparable with that of fumagillin and significantly superior to that of the control compound of the prior art. These results demonstrate good anti-angiogenic activity for the compounds according to the invention.

b) Measurement of the Inhibition of the Proliferation in Endothelial Cells Isolated from the Vein of Umbilical Cords (Prepared at the Laboratory) by DNA Synthesis Reinitiation The cells are seeded in complemented SFM medium (Gibco). When the cells reach the confluence, the growth is stopped by 2 washes in serum free medium and handing-over in serum free medium for 24 h. After trypsination, they are seeded in 48 wells plates: 50.000 cells per well in 500 µl.

The reinitiation of DNA synthesis is performed 6 hours after, in presence of 50 µg/ml b-Fgf by well with increasing amounts of inhibitor to be tested in the serum free medium and containing the tritiated thymidine (b-Fgf is prepared at the laboratory).

The cells are incubated 24 h at 37° C. and the radioactivity is measured with a Wallac counter. Each test is performed in duplicate and the result is the average of the counted number of cpms. The curve showing measured radioactivity function to increasing amount of inhibitors allows to determine graphically the value of IC50.

| Compound | $IC_{50}$ (nM) |
|---|---|
| Control (5-methoxy-4-[2-methyl-3-(3-methylbut-2-enyl)oxiranyl]-1-oxaspiro[2.5]octan-6-yl 4-methoxycinnamate) | 10 |
| Example 2 | 1 |

What is claimed is:

1. A compound represented by formula (I):

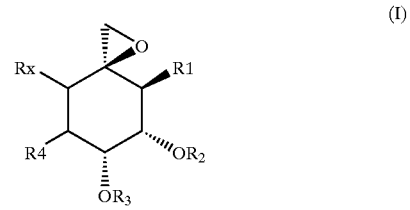

wherein:

Rx represents H, a linear or branched alkyl radical of 1 to 5 carbon atoms or a linear or branched 1-hydroxyalkyl radical of 1 to 5 carbon atoms;

$R_1$ represents a linear or branched alkyl radical of 1 to 5 carbon atoms, or an alkenyl radical having the formula (a) or the corresponding epoxide represented by formula (b),

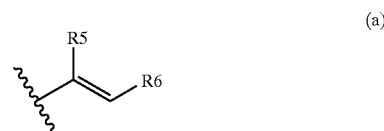

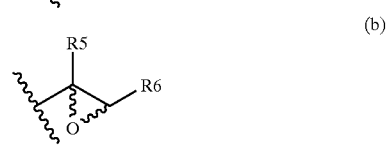

$R_5$ and $R_6$ having the meanings given below, $R_2$ is H or a linear alkyl radical of 1 to 5 carbon atoms, $R_3$ is H or a radical represented by formula (c) or (d),

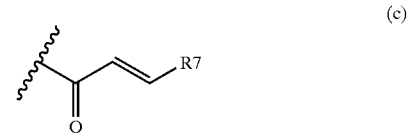

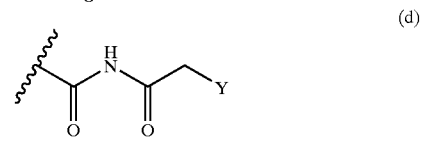

$R_7$ and Y having the meanings given below, $R_4$ is H, a linear or branched alkyl radical of 1 to 5 carbon atoms, or a radical $XR_{11}$, X and $R_{11}$ having the meanings given below, $R_5$ is H or a methyl radical, $R_6$ is H or a linear or branched alkyl radical of 1 to 5 carbon atoms, the radicals $R_5$ and $R_6$, taken together, form a saturated or unsaturated carbocycle of 3 to 10 carbon atoms, $R_7$ is a polyunsaturated chain containing from 5 to 7 carbon atoms and a terminal carboxyl function or an aromatic nucleus represented by to the general formula (e),

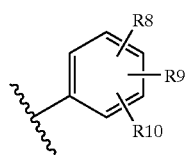

$R_8$, $R_9$ and $R_{10}$ are, independently, H or $OCH_3$, $R_{11}$ is H, an alkyl radical of 1 to 5 carbon atoms or an aromatic nucleus, X represents O or S.

Y represents a halogen atom chosen from chlorine, bromine, iodine and fluorine, given that, when $R_2$ represents an alkyl of 1 to 5 carbon atoms and $R_4$ represents H, then $R_1$ represents an alkyl of 1 to 5 carbon atoms or an alkenyl having the formula (a) and when R1 represents the radical (b), then Rx and $R_4$ cannot simultaneously represent H and the optical and geometrical isomers, the salts and also mixtures of compounds of formula (I).

2. The compound according to claim 1, wherein said compound is in the form of a salt of selected from the group consisting of sodium salts, potassium salts, ammonium salts, and salts derived from lysine or from ethanolamine.

3. The compound according to claim 1, wherein the alkyl radicals of 1 to 5 carbon atoms are selected from the group consisting of methyl, ethyl, isopropyl, tert-butyl and isopentyl radicals.

4. The compound according to claim 1, wherein $R_{11}$ is an aromatic nucleus radical selected from the group consisting of thiophene, pyrrole, naphthalene, benzene and furan radicals.

5. The compound according to claim 1, wherein the radicals $R_5$ and $R_6$ together form a carbocycle is a cyclohexene radical.

6. The compound according to claim 1, wherein said compound has at least one of the following characteristics:

$R_1$ represents the radicals of formula (a) or (b), $R_2$ represents a methyl radical, $R_3$ represents the radical of formula (c), or $R_7$ represents an aromatic nucleus of formula (e).

7. The compound according to claim 1, wherein $R_4$ is a methyl or ethyl radical.

8. The compound according to claim 1, alone or as a mixture, wherein said compound is selected from the group consisting of:

(3R,4S,5S,6R)-5-methoxy-4-methyl-1-oxaspiro[2,5]oct-6-yl 4-methoxycinnamate;

(3R,4S,5S,6R)-5-methoxy-4-[(E)-1,5-dimethylhexyl]-1-oxaspiro[2,5]oct-6-yl 4-methoxycinnamate;

(3R,4S,5S,6R,7R)-6-hydroxy-5-methoxy-7-methyl-4-[(E)-1,5-dimethylhexyl]-1-oxaspiro[2,5]octane;

(3R,4S,5S,6R,7R)-6-hydroxy-5-methoxy-7-methyl-4-[(1R,2R)-1,2-epoxy-1,5-dimethylhexyl]-1-oxaspiro[2,5]octane;

(3R,4S,5S,6R,7R)-5-methoxy-7-methyl-4-[(1R,2R)-1,2-epoxy-1,5-dimethylhexyl]-1-oxaspiro[2,5]oct-6-yl 4-methoxycinnamate;

(3R,4S,5S,6R,7R)-7-ethyl-6-hydroxy-5-methoxy-4-[(1R,2R)-1,2-epoxy-1,5-dimethylhexyl]-1-oxaspiro[2,5]octane;

(3R,4S,5S,6R,7R)-7-ethyl-5-methoxy-4-[(1S,2S)-1,2epoxy-1,5-dimethylhexyl]-1-oxaspiro[2,5]oct-6-yl 4-methoxycinnamate;

(3R,4S,5S,6R)-4cyclohex-1-enyl)-5-methoxy-1-oxaspiro[2,5]oct-6-yl 4-methoxycinnamate;

(3R,4S,5S,6R,7S)-4-(1,5-dimethylhex-1-enyl)-5-methoxy-7-methyl-1-oxaspiro[2,5]oct-6-yl 4-methoxycinnamate;

(3R,4S,5S,6R,7S)-4-(1,5-dimethylhex-1-enyl)-7-hydroxy-5-methoxy-1-oxaspiro[2,5]oct-6-yl 4-methoxycinnamate;

(3R,4S,5S,6R,8R)-4-(1,5-dimethylhex-1-enyl)-5-methoxy-8-methyl-1-oxaspiro[2,5]oct-6-yl 4-methoxycinnamate;

(3R,4S,5S,6R,7R)-5-methoxy-4-[(1R,2R)-1,2-epoxy-1,5-dimethylhexyl]-7-pentyl-1-oxaspiro[2,5]oct-6-yl 4-methoxycinnamate;

(3R,4S,5S,6R)-5-methoxy-4-methyl-1-oxaspiro[2,5]oct-yl 3,4,5-methoxycinnamate;

(3R,4S,5S,6R,7R)-5-methoxy-7-methyl-4-[(1R,2R)-1,2-epoxy-1,5-dimethylhexyl]-1-oxaspiro[2,5]oct-6-yl 3,4,5-methoxycinnamate;

(3R,4S,5S,6R,7R)-7-ethyl-5-methoxy-4-[(1R,2R)-1,2-epoxy-1,5-dimethylhexyl]-1-oxaspiro[2,5]oct-yl 3,4,5-methoxycinnamate;

(3R,4S,5S,6R,7R)-5-methoxy-4-(1R,2R)-1,2-epoxy-1,5-dimethylhexyl]-7-pentyl-1-oxaspiro[2,5]oct-6-yl 3,4,5-methoxycinnamate;

(3R,4S,5S,6R)-4-(cyclohex-1-enyl)-1-oxaspiro[2,5]oct-6-yl 3,4,5-methoxycinnamate;

deca-2,4,6,8-tetraenedioic acid mono{(3R,4S,5S,6R)-5-methoxy-4-methyl-1-oxaspiro[2,5]oct6-yl} ester;

deca-2,4,6,8-tetraenedioic acid mono{(3R,4S,5S,6R,7R)-5-methoxy-7-methyl-4-[(1R,2R)-1,2-epoxy-1,5-dimethylhexyl]-1-oxaspiro[2,5]oct-6-yl} ester;

deca-2,4,6,8-tetraenedioic acid mono{(3R,4S,5S,6R,7R)-7-ethyl-5-methoxy-4-[(1R,2R)-1,2-epoxy-1,5-dimethylhexyl]-1-oxaspiro[2,5]oct-6-yl} ester;

deca-2,4,6,8-tetraenedioic acid mono{(3R,4S,5S,6R,7R)-5-methoxy-4-[(1R,2R)-1,2-epoxy-1,5-dimethylhexyl]-7-pentyl-1-oxaspiro[2,5]oct-6-yl} ester;

deca-2,4,6,8-tetraenedioic acid mono{(3R,4S,5S,6R)-4-(cyclohex-1-enyl)-1-oxaspiro[2,5]oct-6-yl} ester;

chloroacetylcarbamic acid mono{(3R,4S,5S,6R)-5-methoxy-4-methyl-1-oxaspiro[2,5]oct-6-yl} ester;

chloroacetylcarbamic acid mono{(3R,4S,5S,6R)-5-methoxy-4-[(1S,2S)-1,2-epoxy-1,5-dimethylhexyl]-1-oxaspiro[2,5]oct-6-yl} ester;

chloroacetylcarbamic acid mono{(3R,4S,5S,6R,7R)-5-methoxy-7-methyl-4-[(1R,2R)-1,2-epoxy-1,5-dimethylhexyl]-1-oxaspiro[2,5]oct-6-yl} ester;

chloroacetylcarbamic acid mono{(3R,4S,5S,6R,7R)-7-ethyl-5-methoxy-4-[(1R,2R)-1,2epoxy-1,5-dimethylhexyl]-1-oxaspiro[2,5]oct-6-yl} ester;

chloroacetylcarbamic acid mono{(3R,4S,5S,6R,7R)-5-methoxy-4-[(1R,2R)-1,2-epoxy-1,5-dimethylhexyl]-7-pentyl-1-oxaspiro[2,5]oct-6-yl} ester; and acetylcarbamic acid mono{(3R,4S,5S,6R)-4-(cyclohex-1-enyl)-1-oxaspiro[2,5]oct-6-yl} ester.

9. A pharmaceutical composition, comprising a pharmaceutically acceptable carrier and at least one compound as defined in claim 1.

10. The pharmaceutical composition according to claim 9, wherein the concentration of said at least one compound is between 0.0001% and 20% by weight relative to the total weight of the composition.

11. A method for treating an angiogenesis disorder or cell proliferation disorder, with or without an inflammatory nature comprising administering a pharmaceutical composition of claim 9 to a subject in need thereof.

12. A cosmetic composition, comprising a cosmetically acceptable carrier and at least one compound as defined in claim 1.

13. The cosmetic composition according to claim 12, wherein the concentration of said at least one compound is between 0.0001% and 3% by weight relative to the total weight of the composition.

14. A method of body or hair hygiene, comprising applying a cosmetic composition of claim 12 to the body or hair of a subject.

15. A method for treating acne-prone skin, for the regrowth of hair, to prevent hair loss, to combat the greasy appearance of the skin or the hair, to protect against the harmful effects of sunlight, to treat physiologically dry skin, or to combat light-induced ageing, comprising applying the cosmetic composition of claim 12 to the skin or hair of a subject in need thereof.

16. The method according to claim 11, wherein the angiogenesis disorder or cell proliferation disorder is a skin disorder selected from the group consisting of haemangiomas, benign or malignant tumours, cancers, melanomas, basal cell carcinomas, pyogenic granuloma, angiofibromas, scleroderma, psoriasis, Kaposi's sarcoma, angiosarcoma, lupus, rosacea, and cicatrization disorders.

17. The method according to claim 16, wherein the cicatrization disorder is a cheloid or hypertrophic scar.

* * * * *